US012298305B2

(12) United States Patent
Buranda et al.

(10) Patent No.: US 12,298,305 B2
(45) Date of Patent: *May 13, 2025

(54) ACTIVATED GTPase-BASED ASSAYS AND KITS FOR THE DIAGNOSIS OF SEPSIS AND OTHER INFECTIONS

(71) Applicant: UNM RAINFOREST INNOVATIONS, Albuquerque, NM (US)

(72) Inventors: Tione Buranda, Albuquerque, NM (US); Jacob Ongudi Agola, Albuquerque, NM (US); Soumik BasuRay, Dallas, TX (US); Scarlett Swanson, Albuquerque, NM (US); Angela Wandinger-Ness, Albuquerque, NM (US); Peter C. Simons, Albuquerque, NM (US); Virginie Bondu, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 1087 days.

This patent is subject to a terminal disclaimer.

(21) Appl. No.: 17/182,859

(22) Filed: Feb. 23, 2021

(65) Prior Publication Data

US 2021/0325392 A1    Oct. 21, 2021

Related U.S. Application Data

(62) Division of application No. 16/270,306, filed on Feb. 7, 2019, now Pat. No. 10,962,541, which is a division
(Continued)

(51) Int. Cl.
*G01N 33/573* (2006.01)
*G01N 33/86* (2006.01)

(52) U.S. Cl.
CPC .......... *G01N 33/573* (2013.01); *G01N 33/86* (2013.01); *G01N 2333/914* (2013.01); *G01N 2800/224* (2013.01); *G01N 2800/26* (2013.01)

(58) Field of Classification Search
CPC ................ G01N 33/573; G01N 33/86; G01N 2333/914; G01N 2800/224; G01N 2800/26
See application file for complete search history.

(56) References Cited

U.S. PATENT DOCUMENTS 5,474,796 A    12/1995    Brennan
5,545,806 A    8/1996    Lonberg et al.
(Continued)

FOREIGN PATENT DOCUMENTS

WO    9511262 A1    4/1995
WO    9535505 A1    12/1995

OTHER PUBLICATIONS

Jelle B, Anderson B, Torrez-Martinez N, Song W, Gannon WL, Yates TL. Prevalence and geographic genetic variation of hantaviruses of New World harvest mice (Reithrodontomys): identification of a divergent genotype from a Costa Rican Reithrodontomys mexicanus. Virology. 1995; 207: 452-59.
(Continued)

*Primary Examiner* — Gailene Gabel
(74) *Attorney, Agent, or Firm* — Henry D. Coleman; R. Neil Sudol

(57) ABSTRACT

In one embodiment, the invention provides a method of diagnosing sepsis or a virus-related infection (often a viral hemorrhagic fever infection) in a subject by detecting and measuring the level of a set of sepsis and virus infection-associated-GTPase biomarkers in a sample obtained from the subject using multiplexed flow cytometry. Related kits are also provided. In a preferred embodiment, the invention provides point of care diagnostic methods for determining
(Continued)

an early stage sepsis or the severity of a virus infection, especially in a hospital or other setting.

5 Claims, 14 Drawing Sheets

Related U.S. Application Data of application No. 14/626,536, filed on Feb. 19, 2015, now Pat. No. 10,261,084.

(60) Provisional application No. 61/941,604, filed on Feb. 19, 2014.

(56) References Cited

U.S. PATENT DOCUMENTS

| | | | |
|---|---|---|---|
| 5,565,332 A | 10/1996 | Hoogenboom et al. | |
| 5,569,825 A | 10/1996 | Onberg et al. | |
| 5,585,089 A | 12/1996 | Queen et al. | |
| 5,605,662 A | 2/1997 | Heller et al. | |
| 5,693,762 A | 12/1997 | Queen et al. | |
| 7,381,535 B2 | 6/2008 | Perez et al. | |
| 7,393,656 B2 | 7/2008 | Perez et al. | |
| 10,261,084 B1 * | 4/2019 | Buranda | G01N 33/573 |
| 2013/0109050 A1 | 5/2013 | Purvis, Jr. | |
| 2014/0162978 A1 | 6/2014 | Nicolaes et al. | |
| 2014/0206008 A1 | 7/2014 | Hu et al. | |

OTHER PUBLICATIONS

Jelle B, Chavez-Giles F, Torrez-Martinez N, et al. Genetic identification of a novel hantavirus of the harvest mouse Reithrodontomys megalotis. J.Virol. 1994; 68: 6751-54.
Surviladze, et al. High-Throughput Flow Cytometry Bead-Based Multiplex Assay for Identification of Rho GTPase Inhibitors. Rho GTPases: Methods and Protocols. Methods in Molecular Biology, 2012;827:253-570.
Jonsson CB, Schmaljohn CS. Replication of hantaviruses. Curr.Top. Microbiol.Immunol. 2001; 256: 15-32.
Brodbeck WG, Kuttner-Kondo L, Mold C, Medof ME. Structure/function studies of human decay-accelerating factor. Immunology. 2000; 101: 104-11.
Coyne CB, Bergelson JM. Virus-induced Abl and Fyn kinase signals permit coxsackievirus entry through epithelial tight junctions. Cell. 2006; 124: 119-31.
Rougeaux C, Berger CN, Servin AL. hCEACAM1-4L downregulates hDAF-associated signalling after being recognized by the Dr adhesin of diffusely adhering *Escherichia coli*. Cellular microbiology. 2008; 10: 632-54.
Shenoy-Scaria AM, Gauen LK, Kwong J, Shaw AS, Lublin DM. Palmitylation of an amino-terminal cysteine motif of protein tyrosine kinases p56lck and p59fyn mediates interaction with glycosylphosphatidylinositol-anchored proteins. Molecular and cellular biology. 1993; 13: 6385-92.
Shenoy-Scaria AM, Kwong J, Fujita T, Olszowy MW, Shaw AS, Lublin DM. Signal transduction through decay-accelerating factor. Interaction of glycosyl-phosphatidylinositol anchor and protein tyrosine kinases p56lck and p59fyn 1. J Immunol. 1992; 149: 3535-41.
Stefanova I, Horejsi V, Ansotegui IJ, Knapp W, Stockinger H. GPI-anchored cell-surface molecules complexed to protein tyrosine kinases. Science (New York, N.Y. 1991; 254: 1016-9.
Schlessinger J. Cell signaling by receptor tyrosine kinases. Cell. 2000; 103: 211-25.
Bar-Sagi D, Hall A. Ras and Rho GTPases: a family reunion. Cell. 2000; 103: 227-38.
Ridley AJ, Hall A. The small GTP-binding protein rho regulates the assembly of focal adhesions and actin stress fibers in response to growth factors. Cell. 1992; 70: 389-99.

Machacek M, Hodgson L, Welch C, et al. Coordination of Rho GTPase activities during cell protrusion. Nature. 2009; 461: 99-103.
Del Pozo MA, Alderson NB, Kiosses WB, Chiang HH, Anderson RG, Schwartz MA. Integrins regulate Rac targeting by internalization of membrane domains. Science (New York, N.Y. 2004; 303: 839-42.
Parsons JT, Horwitz AR, Schwartz MA. Cell adhesion: integrating cytoskeletal dynamics and cellular tension. Nat Rev Mol Cell Biol. 2010; 11: 633-43.
Wittchen ES, van Buul JD, Burridge K, Worthylake RA. Trading spaces: Rap, Rac, and Rho as architects of transendothelial migration. Current opinion in hematology. 2005; 12: 14-21.
Wittchen ES, Burridge K. Analysis of low molecular weight GTPase activity in endothelial cell cultures. Methods in enzymology. 2008; 443: 285-98.
Lad Y, McHugh B, Hodkinson PS, et al. Phospholipase C epsilon suppresses integrin activation. The Journal of biological chemistry. 2006; 281: 29501-12.
Kinbara K, Goldfinger LE, Hansen M, Chou FL, Ginsberg MH. Ras GTPases: integrins' friends or foes? Nat Rev Mol Cell Biol. 2003; 4: 767-76.
Hughes PE, Oertli B, Hansen M, Chou FL, Willumsen BM, Ginsberg MH. Suppression of integrin activation by activated Ras or Raf does not correlate with bulk activation of ERK MAP kinase. Molecular biology of the cell. 2002; 13: 2256-65.
Zwartkruis FJ, Bos JL. Ras and Rap1: two highly related small GTPases with distinct function. Experimental cell research. 1999; 253: 157-65.
Feng Y, Press B, Chen W, Zimmerman J, Wandinger-Ness A. Expression and properties of Rab7 in endosome function. Methods in enzymology. 2001; 329: 175-87.
Feng Y, Press B, Wandinger-Ness A. Rab 7: an important regulator of late endocytic membrane traffic. The Journal of cell biology. 1995; 131: 1435-52.
Agola J, Jim P, Ward H, Basuray S, Wandinger-Ness A. Rab GTPases as regulators of endocytosis, targets of disease and therapeutic opportunities. Clinical genetics. 2012.
Lozach PY, Huotari J, Helenius A. Late-penetrating viruses. Current opinion in virology; 1: 35-43, (2005).
Lozach PY, Mancini R, Bitto D, et al. Entry of bunyaviruses into mammalian cells. Cell host & microbe; 7: 488-99, (2005).
Mitin N, Rossman KL, Der CJ. Signaling interplay in Ras superfamily function. Curr Biol. 2005; 15: R563-74.
Surviladze Z, Young SM, Sklar LA. High-throughput flow cytometry bead-based multiplex assay for identification of Rho GTPase inhibitors. Methods in molecular biology (Clifton, N.J. 2012; 827: 253-70.
Bharadwaj M, Lyons CR, Wortman IA, Hjelle B. Intramuscular inoculation of Sin Nombre hantavirus cDNAs induces cellular and humoral immune responses in BALB/c mice. Vaccine. 1999; 17: 2836-43.
Buranda T, Wu Y, Perez D, et al. Recognition of DAF and avb3 by inactivated Hantaviruses, towards the development of HTS flow cytometry assays. Anal. Biochem. 2010; 402: 151-60.
Tessema M, Simons PC, Cimino DF, et al. Glutathione-S-transferase-green fluorescent protein fusion protein reveals slow dissociation from high site density beads and measures free GSH. Cytometry A. 2006; 69: 326-34.
Schwartz SL, Tessema M, Buranda T, et al. Flow cytometry for real-time measurement of guanine nucleotide binding and exchange by Ras-like GTPases. Analytical biochemistry. 2008; 381: 258-66.
Chigaev A, Buranda T, Dwyer DC, Prossnitz ER, Sklar LA. FRET detection of cellular alpha 4-integrin conformational activation. Biophysical Journal. 2003; 85: 3951-62.
Sandvig K, Olsnes S, Petersen OW, van Deurs B. Inhibition of endocytosis from coated pits by acidification of the cytosol. Journal of cellular biochemistry. 1988; 36: 73-81.
Sandvig K, Olsnes S, Petersen OW, van Deurs B. Acidification of the cytosol inhibits endocytosis from coated pits. The Journal of cell biology. 1987; 105: 679-89.
Somsel Rodman J, Wandinger-Ness A. Rab GTPases coordinate endocytosis. Journal of cell science. 2000; 113 Pt 2: 183-92.

(56) References Cited

OTHER PUBLICATIONS

Rink J, Ghigo E, Kalaidzidis Y, Zerial M. Rab conversion as a mechanism of progression from early to late endosomes. Cell. 2005; 122: 735-49.
Parton RG, Schrotz P, Bucci C, Gruenberg J. Plasticity of early endosomes. Journal of cell science. 1992; 103 ( Pt 2): 335-48.
Vonderheit A, Helenius A. Rab7 associates with early endosomes to mediate sorting and transport of Semliki forest virus to late endosomes. PLoS biolo, 3 (7): e233 pp. 1225-1238 (Jul. 2005).
McAdow, M. et al. Preventing *Staphylococcus aureus* Sepsis through the Inhibition of Its Agglutination in Blood. PLoS pathogens 7 (2011).
Sun, H.M. The interaction between pathogens and the host coagulation system. Physiology 21, 281-288 (2006).
Van der Poll, T. & Herwald, H. The coagulation system and its function in early immune defense. Thrombosis and haemostasis 112 (2014).
Wang, H.J. et al. Identification of four novel serum protein biomarkers in sepsis patients encoded by target genes of sepsis-related miRNAs. Clin Sci 126, 857-867 (2014).
Sankar, V. & Webster, N.R. Clinical application of sepsis biomarkers. J Anesth 27, 269-283 (2013).
Pierrakos, C. & Vincent, J.L. Sepsis biomarkers: a review. Critical care 14 (2010).
Faix, J.D. Established and novel biomarkers of sepsis. Biomark Med 5, 117-130 (2011).
Charles, P.E. & Gibot, S. Predicting outcome in patients with sepsis: new biomarkers for old expectations. Critical care 18 (2014).
Reinhart, K., Bauer, M., Riedemann, N.C. & Hartog, C.S. New Approaches to Sepsis: Molecular Diagnostics and Biomarkers. Clin Microbiol Rev 25, 609-634 (2012).
Vitiello, M. et al. Pathophysiological changes of gram-negative bacterial infection can be reproduced by a synthetic peptide mimicking loop L7 sequence of Haemophilus influenzae porin. Microbes and infection / Institut Pasteur 10, 657-663 (2008).
Lahteenmaki, K., Kuusela, P. & Korhonen, T.K. Bacterial plasminogen activators and receptors. FEMS microbiology reviews 25, 531-552 (2001).
Bhattacharya, S., Ploplis, V.A. & Castellino, F.J. Bacterial plasminogen receptors utilize host plasminogen system for effective invasion and dissemination. Journal of biomedicine & biotechnology 2012, 482096 (2012).
Rivera, J., Vannakambadi, G., Hook, M. & Speziale, P. Fibrinogen-binding proteins of Gram-positive bacteria. Thrombosis and haemostasis 98, 503-511 (2007).
Aktories, K. & Barbieri, J.T. Bacterial cytotoxins: targeting eukaryotic switches. Nature reviews. Microbiology 3, 397-410 (2005).
Aktories, K. & Just, I. Clostridial Rho-inhibiting protein toxins. Current topics in microbiology and immunology 291, 113-145 (2005).
Aktories, K. & Schmidt, G. A new turn in Rho GTPase activation by *Escherichia coli* cytotoxic necrotizing factors. Trends in microbiology 11, 152-155 (2003).
Bokoch, G.M. Regulation of innate immunity by Rho GTPases. Trends Cell Biol 15, 163-171 (2005).
Boquet, P. & Lemichez, E. Bacterial virulence factors targeting Rho GTPases: parasitism or symbiosis? Trends Cell Biol 13, 238-246 (2003).
Cherfils, J. & Zeghouf, M. Regulation of small GTPases by GEFs, GAPs, and GDIs. Physiological reviews 93, 269-309 (2013).
Lemichez, E. & Aktories, K. Hijacking of Rho GTPases during bacterial infection. Experimental cell research 319, 2329-2336 (2013).
Tapper, H. & Herwald, H. Modulation of hemostatic mechanisms in bacterial infectious diseases. Blood 96, 2329-2337 (2000).
Stearns-Kurosawa, D.J., Osuchowski, M.F., Valentine, C., Kurosawa, S. & Remick, D.G. The Pathogenesis of Sepsis. Annu Rev Pathol-Mech 6, 19-48 (2011).
Skibsted, S. et al. Biomarkers of endothelial cell activation in early sepsis. Shock 39, 427-432 (2013).
Kim, W.S. & Lee, H.J. Management of sepsis. J Korean Med Assoc 56, 819-826 (2013), Abstract only.
Hernandez, G., Bruhn, A. & Ince, C. Microcirculation in Sepsis: New Perspectives. Current vascular pharmacology 11, 161-169 (2013).
Rittirsch, D., Flierl, M.A. & Ward, P.A. Harmful molecular mechanisms in sepsis. Nat Rev Immunol 8, 776-787 (2008).
Levi, M., Keller, T.T., van Gorp, E. & ten Cate, H. Infection and inflammation and the coagulation system. Cardiovascular research 60, 26-39 (2003).
Kumar, P. et al. Molecular mechanisms of endothelial hyperpermeability: implications in inflammation. Expert Rev Mol Med 11 (2009).
Escolar, G., Bozzo, J. & Maragall, S. Argatroban: A direct thrombin inhibitor with reliable and predictable anticoagulant actions. Drugs Today 42, 223-236 (2006).
Carbajal, J.M., Gratrix, M.L., Yu, C.H. & Schaeffer, R.C., Jr. ROCK mediates thrombin's endothelial barrier dysfunction. American journal of physiology. Cell physiology 279, C195-204 (2000).
Anwar, K.N., Fazal, F., Malik, A.B. & Rahman, A. RhoA/Rho-associated kinase pathway selectively regulates thrombin-induced intercellular adhesion molecule-1 expression in endothelial cells via activation of I kappa B kinase beta and phosphorylation of RelA/p65. J Immunol 173, 6965-6972 (2004).
Sosothikul, D., Seksam, P., Pongsewalak, S., Thisyakorn, U. & Lusher, J. Activation of endothelial cells, coagulation and fibrinolysis in children with Dengue virus infection. Thrombosis and haemostasis 97, 627-634 (2007).
Aine, O. et al. Enhanced thrombin formation and fibrinolysis during acute Puumala hantavirus infection. Thrombosis research 126, 154-158 (2010).
Dubis, J. & Witkiewicz, W. The Role of Thrombin-Activatable Fibrinolysis Inhibitor in the Pathophysiology of Hemostasis. Adv Clin Exp Med 19, 379-387 (2010).
Bondu-Hawkins, V. et al. Elevated Plasma Cytokine, Thrombin, and PAI-1 Levels in Patients with Severe Hantavirus Cardiopulmonary Syndrome Due to Sin Nombre Virus Viruses in press (2014).
Buranda, T. et al. Rapid parallel flow cytometry assays of active GTPases using effector beads. Analytical biochemistry 144, 149-157 (2013).
Buranda, T. et al. Equilibrium and Kinetics of Sin Nombre Hantavirus Binding at DAF/CD55 Functionalized Bead Surfaces. Viruses-Basel 6, 1091-1111 (2014).
Osuchowski, M.F., Welch, K., Siddiqui, J. & Remick, D.G. Circulating cytokine/inhibitor profiles reshape the understanding of the SIRS/CARS continuum in sepsis and predict mortality. J Immunol 177, 1967-1974 (2006).
Lvovschi, V. et al. Cytokine profiles in sepsis have limited relevance for stratifying patients in the emergency department: a prospective observational study. PloS one 6, e28870 (2011).
Van Nieuw Amerongen, G.P., van Delft, S., Vermeer, M.A., Collard, J.G. & van Hinsbergh, V.W. Activation of RhoA by thrombin in endothelial hyperpermeability: role of Rho kinase and protein tyrosine kinases. Circulation research 87, 335-340 (2000).
Van Nieuw Amerongen, G.P., Musters, R.J., Eringa, E.C., Sipkema, P. & van Hinsbergh, V.W. Thrombin-induced endothelial barrier disruption in intact microvessels: role of RhoA/Rho kinase-myosin phosphatase axis. American journal of physiology. Cell physiology 294, C1234-1241 (2008).
Stefansson, S., Lawrence, D.A. & Argraves, W.S. Plasminogen activator inhibitor-1 and vitronectin promote the cellular clearance of thrombin by low density lipoprotein receptor-related proteins 1 and 2. The Journal of biological chemistry 271, 8215-8220 (1996).
Rosenfeldt, H., Castellone, M.D., Randazzo, P.A. & Gutkind, J.S. Rac inhibits thrombin-induced Rho activation: evidence of a Pak-dependent GTPase crosstalk. Journal of molecular signaling 1, 8 (2006).
Gavard, J. & Gutkind, J.S. Protein kinase C-related kinase and ROCK are required for thrombin-induced endothelial cell permeability downstream from Galpha12/13 and Galpha11/q. The Journal of biological chemistry 283, 29888-29896 (2008).

(56) References Cited

OTHER PUBLICATIONS

Vogel, S.M. et al. Abrogation of thrombin-induced increase in pulmonary microvascular permeability in PAR-1 knockout mice. Physiol Genomics 4, 137-145 (2000).

Boling, B. & Moore, K. Tranexamic acid (TXA) use in trauma. Journal of emergency nursing: JEN : official publication of the Emergency Department Nurses Association 38, 496-497 (2012).

Kawkitinarong, K., Linz-McGillem, L., Birukov, K.G. & Garcia, J.G. Differential regulation of human lung epithelial and endothelial barrier function by thrombin. American journal of respiratory cell and molecular biology 31, 517-527 (2004).

Standage, S.W. & Wong, H.R. Biomarkers for pediatric sepsis and septic shock. Expert Rev Anti-Infe 9, 71-79 (2011).

Hong, T.H. et al. Biomarkers of early sepsis may be correlated with outcome. J Transl Med 12 (2014).

Gavard, J. et al. A role for a CXCR2/phosphatidylinositol 3-kinase gamma signaling axis in acute and chronic vascular permeability. Molecular and cellular biology 29, 2469-2480 (2009).

Duboscq, C. et al. Plasminogen: An important hemostatic parameter in septic patients. Thrombosis and haemostasis 77, 1090-1095 (1997).

Vaughan, D.E. PAI-1 and atherothrombosis. Journal of Thrombosis and Haemostasis 3, 1879-1883 (2005).

Nykjaer, A. et al. Both pro-uPA and uPA: PAI-1 complex bind to the alpha 2-macroglobulin receptor/LDL receptor-related protein. Evidence for multiple independent contacts between the ligands and receptor. Annals of the New York Academy of Sciences 737, 483-485 (1994).

Degryse, B., Sier, C.F., Resnati, M., Conese, M. & Blasi, F. PAI-1 inhibits urokinase-induced chemotaxis by internalizing the urokinase receptor. FEBS letters 505, 249-254 (2001).

Cheung, A.L., Bayer, A.S., Zhang, G., Gresham, H. & Xiong, Y.Q. Regulation of virulence determinants in vitro and in vivo in *Staphylococcus aureus*. FEMS immunology and medical microbiology 40, 1-9 (2004).

Jaffe, A.B. & Hall, A. Rho GTPases: biochemistry and biology. Annual review of cell and developmental biology 21, 247-269 (2005).

Arthur, W.T. & Burridge, K. RhoA inactivation by p190RhoGAP regulates cell spreading and migration by promoting membrane protrusion and polarity. Molecular biology of the cell 12, 2711-2720 (2001).

Benjamini, Y. & Hochberg, Y. Controlling the False Discovery Rate—a Practical and Powerful Approach to Multiple Testing. J Roy Stat Soc B Met 57, 289-300 (1995).

Benjamini, Y., Drai, D., Elmer, G., Kafkafi, N. & Golani, I. Controlling the false discovery rate in behavior genetics research. Behavioural brain research 125, 279-284 (2001).

Koch, A. et al. Circulating soluble urokinase plasminogen activator receptor is stably elevated during the first week of treatment in the intensive care unit and predicts mortality in critically ill patients. Critical care 15, R63 (2011).

Rymer, J.C. et al. A new approach for clinical biological assay comparison and standardization: Application of principal component analysis to a multicenter study of twenty-one carcinoembryonic antigen immunoassay kits. Clinical Chemistry ; 45, 869-881 (1999).

Webb-Robertson, B.J. et al. Sequential projection pursuit principal component analysis-dealing with missing data associated with new-omics technologies. BioTechniques 54, 165-168 (2013).

Pooladi, M. et al. Cluster and Principal Component Analysis of Human Glioblastoma Multiforme (GBM) Tumor Proteome. Iranian journal of cancer prevention 7, 87-95 (2014).

Marengo, E. et al. Study of proteomic changes associated with healthy and tumoral murine samples in neuroblastoma by principal component analysis and classification methods. Clinica chimica acta; international journal of clinical chemistry 345, 55-67 (2004).

Alonso-Gutierrez, J. et al. Principal component analysis of proteomics (PCAP) as a tool to direct metabolic engineering. Metabolic engineering (2014).

Dennis, G., Jr. et al. DAVID: Database for Annotation, Visualization, and Integrated Discovery. Genome biology 4, P3 (2003).

Ward, J.H. Hierarchical Grouping to Optimize an Objective Function. J Am Stat Assoc 58, 236-& (1963).

Leitner, G. et al. Effects of intra-mammary bacterial infection with coagulase negative staphylococci and stage of lactation on shedding of epithelial cells and infiltration of leukocytes into milk: Comparison among cows, goats and sheep. Vet Immunol Immunop 147, 202-210 (2012).

Chang, D.W. et al. Proteomic and computational analysis of bronchoalveolar proteins during the course of the acute respiratory distress syndrome. Am J Resp Crit Care 178, 701-709 (2008).

Guilluy C, Garcia-Mata R, Burridge K. Rho protein crosstalk: another social network? Trends Cell Biol. 2011.

Cherfils J, Zeghouf M. Regulation of small GTPases by GEFs, GAPs, and GDIs. Physiol Rev. 2013;93:269-309.

Schiller MR. Coupling receptor tyrosine kinases to Rho GTPases—GEFs what's the link. Cell Signal.2006;18:1834-43.

Moon SY, Zheng Y. Rho GTPase-activating proteins in cell regulation. Trends Cell Biol. 2003;13:13-22.

Hong L, Kenney SR, Phillips GK, Simpson D, Schroeder CE, Noth J, Romero E, Swanson S, Waller A, Strouse JJ, Carter M, Chigaev A, Ursu O, Oprea T, Hjelle B, Golden JE, Aube J, Hudson LG, Buranda T, Sklar LA, Wandinger-Ness A. Characterization of a cdc42 protein inhibitor and its use as a molecular probe. J Biol Chem.2013;288:8531-43.

Agola JO, Hong L, Surviladze Z, Ursu O, Waller A, Strouse JJ, Simpson DS, Schroeder CE, Oprea TI, Golden JE, Aube J, Buranda T, Sklar LA, Wandinger-Ness A. A competitive nucleotide binding inhibitor: in vitro characterization of Rab7 GTPase inhibition. ACS Chem Biol. 2012;7:1095-108.

Friesland A, Zhao Y, Chen YH, Wang L, Zhou H, Lu Q. Small molecule targeting Cdc42-intersectin interaction disrupts Golgi organization and suppresses cell motility. Proc Natl Acad Sci U S A. 2013;110:1261-6.

Safronetz D, Ebihara H, Feldmann H, Hooper JW. The Syrian hamster model of hantavirus pulmonary syndrome. Antiviral Res. 2012;95:282-92.

Grove J, Marsh M. Host-pathogen interactions: The cell biology of receptor-mediated virus entry. J Cell Biol.2011;195:1071-82.

Buranda, et al. Recognition of decay accelerating factor and alpa(v)beta(3) by inactivated hantaviruses: Toward the development of high-throughput screening flow cytometry assays. Analytical Biochemistry, 2010;402:151-160.

Colucci AM, Spinosa MR, Bucci C. Expression, assay, and functional properties of RILP. Methods Enzymol. 2005;403:664-75.

Tessema M, Simons PC, Cimino DF, Sanchez L, Waller A, Posner RG, Wandinger-Ness A, Prossnitz ER, Sklar LA. Glutathione-S-transferase-green fluorescent protein fusion protein reveals slow dissociation from high site density beads and measures free GSH. Cytometry A.2006;69:326-34.

Curpan RF, Simons PC, Zhai D, Young SM, Carter MB, Bologa CG, Oprea TI, Satterthwait AC, Reed JC, Edwards BS, Sklar LA. High-throughput screen for the chemical inhibitors of antiapoptotic bcl-2 family proteins by multiplex flow cytometry. Assay Drug Dev Technol.2011;9:465-74.

Klasse PJ, Moore JP. Quantitative model of antibody- and soluble CD4-mediated neutralization of primary isolates and T-cell line-adapted strains of human immunodeficiency virus type 1. J Virol. 1996;70:3668-77.

Simons PC, Young SM, Carter MB, Waller A, Zhai D, Reed JC, Edwards BS, Sklar LA. Simultaneous in vitro molecular screening of protein-peptide interactions by flow cytometry, using six Bcl-2 family proteins as examples. Nat Protoc. 2011;6:943-52.

Krautkramer E, Zeier M. Hantavirus causing hemorrhagic fever with renal syndrome enters from the apical surface and requires decay-accelerating factor (DAF/CD55) J Virol. 2008;82:4257-64.

Mold C, Walter EI, Medof ME. The influence of membrane components on regulation of alternative pathway activation by decay-accelerating factor. J Immunol. 1990;145:3836-41.

Reeder MK, Serebriiskii IG, Golemis EA, Chernoff J. Analysis of small GTPase signaling pathways using p21-activated kinase mutants that selectively couple to Cdc42.J Biol Chem. 2001;276:40606-13.

(56) References Cited

OTHER PUBLICATIONS

Reid T, Furuyashiki T, Ishizaki T, Watanabe G, Watanabe N, Fujisawa K, Morii N, Madaule P, Narumiya S. Rhotekin, a new putative target for Rho bearing homology to a serine/threonine kinase, PKN, and rhophilin in the rho-binding domain. J Biol Chem. 1996;271:13556-60.
Burridge K, Wennerberg K. Rho and Rac take center stage. Cell. 2004;116:167-79.
Ridley AJ, Schwartz MA, Burridge K, Firtel RA, Ginsberg MH, Borisy G, Parsons JT, Horwitz AR. Cell migration: integrating signals from front to back. Science.2003;302:1704-9.
Ridley AJ. Rho family proteins: coordinating cell responses. Trends Cell Biol. 2001;11:471-7.
Medley QG, Serra-Pages C, Iannotti E, Seipel K, Tang M, O'Brien SP, Streuli M. The trio guanine nucleotide exchange factor is a RhoA target. Binding of RhoA to the trio immunoglobulin-like domain. J Biol Chem.2000;275:36116-23.
Bellanger JM, Astier C, Sardet C, Ohta Y, Stossel TP, Debant A. The Rac1- and RhoG-specific GEF domain of Trio targets filamin to remodel cytoskeletal actin. Nat Cell Biol. 2000;2:888-92.
Schoenwaelder SM, Petch LA, Williamson D, Shen R, Feng GS, Burridge K. The protein tyrosine phosphatase Shp-2 regulates RhoA activity. Curr Biol. 2000;10:1523-6.
Burridge K, Doughman R. Front and back by Rho and Rac. Nat Cell Biol. 2006;8:781-2.
Kurokawa K, Itoh RE, Yoshizaki H, Nakamura YO, Matsuda M. Coactivation of Rac1 and Cdc42 at lamellipodia and membrane ruffles induced by epidermal growth factor. Mol Biol Cell. 2004;15:1003-10.
Mochizuki N, Yamashita S, Kurokawa K, Ohba Y, Nagai T, Miyawaki A, Matsuda M. Spatio-temporal images of growth-factor-induced activation of Ras and Rap1. Nature. 2001;411:1065-8.
Honda S, Tomiyama Y, Pelletier AJ, Annis D, Honda Y, Orchekowski R, Ruggeri Z, Kunicki TJ. Topography of ligand-induced binding sites, including a novel cation-sensitive epitope (AP5) at the amino terminus, of the human integrin beta 3 subunit. J Biol Chem. 1995;270:11947-54.
Wojciak-Stothard B, Ridley AJ. Rho GTPases and the regulation of endothelial permeability. Vascul Pharmacol.2002;39:187-99.
Remans PH, Gringhuis SI, van Laar JM, Sanders ME, Papendrecht-van der Voort EA, Zwartkruis FJ, Levarht EW, Rosas M, Coffer PJ, Breedveld FC, Bos JL, Tak PP, Verweij CL, Reedquist KA. Rap1 signaling is required for suppression of Ras-generated reactive oxygen species and protection against oxidative stress in T lymphocytes. J Immunol. 2004;173:920-31.
Bucci C, Parton RG, Mather IH, Stunnenberg H, Simons K, Hoflack B, Zerial M. The small GTPase rab5 functions as a regulatory factor in the early endocytic pathway. Cell. 1992;70:715-28.
Lozach PY, Mancini R, Bitto D, Meier R, Oestereich L, Overby AK, Pettersson RF, Helenius A. Entry of bunyaviruses into mammalian cells. Cell Host Microbe.2010;7:488-99.
Vega, F.M.; Ridley, A.J. Rho gtpases in cancer cell biology. FEBS letters 2008, 582, 2093-2101.
Iden, S.; Collard, J.G. Crosstalk between small gtpases and polarity proteins in cell polarization. Nature reviews. Molecular cell biology 2008, 9, 846-859.
Simons, et al. Simultaneous in vitro screening of protein-peptide interactions by flow cytometry using six Bcl-2 family proteins as examples. Nature Protocols, 2011;6(7):943-952.
Anne Ridley. Rho family proteins: coordinating responses. Trends in Cell Biology, 2001;11(12):471-479.
Lemichez, et al. Hijacking of Rho GTPases during bacterial infection. Experimental Cell Research, 2013;319:2329-2336.
Szulcek, et al. Localized RhoA GTPase activity regulated dynamics of endothelial monolayer integrity. Cardiocascular Research, 2013;99:471-482.
Ridley AJ, Hall LL. The small GTP-binding protein rho regulates the assembly of focal adhesions and actin stress fibers in response to growth factors. Cell, 1992;70:389-399.
Hjelle B, et al. Hantaviruses: Clinical, Microbiolgic, and Epidemiologic Aspects. Critical Reviews in Clinical Laboratory Sciences, 1995;32(5):469-508.
Simons, et al. Simultaneous in vitro molecular screening of protein-peptide interactions by flow cytometry using six Bcl-2 family proteins as examples. Nature Protocols, 2011;6(7):943-9952.
Szulcek, et al. Localized RhoA GTPase activity regulates dynamics of endothelial monolayer integrity. Cardiovascular Research, 2013;471:482.

\* cited by examiner

ACTIVATED GTPase-BASED ASSAYS AND KITS FOR THE DIAGNOSIS OF SEPSIS AND OTHER INFECTIONS

CROSS-REFERENCE TO RELATED APPLICATIONS

This application is a divisional application of U.S. patent application Ser. No. 14/626,536 filed on Feb. 19, 2015, which claims priority from U.S. Provisional Patent Application Ser. No. 61/941,604, entitled "Rapid, Effector-Based, Flow-Cytometry Assay for Activated GTPases", and filed 19 Feb. 2014. The complete contents of these two priority patent application are hereby incorporated by reference in their entirety.

STATEMENT REGARDING FEDERAL FUNDING

This invention was made with government support under Grant No. 1R21NS066435 awarded by the National Institute of Neurological Disorders and Stroke (NINDS); Grant Nos. R03A1082130, R03AI092130, R21NS066429 and 1P50GM085273 awarded by the National Institute of Health (NIH); and Grant No. MCB0956027 awarded by the National Science Foundation (NSF). Consequently, the government has certain rights in the invention.

FIELD OF THE INVENTION

In one embodiment, the invention provides a method of diagnosing a bacterial infection (sepsis) in a subject by using multiplexed flow cytometry to detect and measure the level of active GTPase enrichment caused by bacterial infection. Related kits are also provided.

In a preferred embodiment, the invention provides point of care activated GTPase-based diagnostic methods and related kits for determining an early stage sepsis, especially in a hospital setting.

More specifically, certain embodiments provide a rapid assay for measuring the cellular activity of small GTPases in response to a specific stimulus. Effector functionalized beads are used to quantify in parallel multiple, GTPbound GTPases in the same cell lysate by flow cytometry. In particular biologically relevant examples, different Ras (HRas, Rap1), Rho (Rac1, Cdc41, RhoA) and Rab (Rab 5) family GTPases are shown for the first time to be involved in a concerted signaling cascade downstream of receptor ligation by Sin Nombre hantavirus. In another setting, the preclinical onset of sepsis was manifested by the enrichment of active GTPases (Rho, Rap1 or Rac1) measured in serial plasma samples taken from trauma patients who were clinically diagnosed with bacterial infection.

BACKGROUND OF THE INVENTION

The Ras superfamily of small GTPases is comprised of five major groups: Ras, Rho, Rab, Arf and Ran that regulate many aspects of cell behavior. The Ras (e.g. H-Ras, K-Ras, R-Ras and Rap 1) and Rho subfamily (e.g. Cdc42, Rac1 and RhoA) of GTPases synergistically regulate signaling pathways that originate from extracellular stimuli, to yield overlapping sets of cellular phenotypes, such as proliferation, differentiation, and remodeling of the cytoskeleton. The GTPases function by cycling between active GTP-bound and inactive GDP-bound states. Guanine nucleotide-exchange factors (GEFs), GTPase-activating proteins (GAPs) and guanine nucleotide-dissociation inhibitors (GDIs) (Guilluy et al., 2011; Jaffe and Hall, 2005) control the activity of the GTPases. GEFs activate Rho proteins by catalyzing the exchange of GDP for GTP, while GAPs inactivate the proteins by stimulating intrinsic GTPase activity. GDI inhibits the activation of Rho GTPases by sequestering them in the cytosol away from membranes. Activated GTPases interact with specific downstream-effector proteins to yield definite physiological responses in response to the upstream stimuli. Ras and Rho family GTPases function as components of a broader signaling network and are interconnected across overlapping signaling pathways that involve positive and negative feedback loops.

The superfamily of GTPases has numerous cellular effects that are dysregulated in disease. Ras (35 members) primarily involved in signaling and cancer. Rho (23 members) GTPases are primarily involved in cell motility, infection and cancer among others. Rab (70 members) GTPases are primarily involved in intracellular transport, cancer, infectious disease, genetic disease and downstream growth factor signaling Ran (1 member) nuclear import, cellular differentiation, Arf (30 members) intracellular transport, infectious disease, human ciliopathies and retinopathies. The dysregulation of these systems can be measured as an increase in the enrichment of active GTPases caused by factors in patient samples. Active GTPases preferentially bind to specific cognate effector molecules that are immobilized on beads, thus providing evidence as to the dysregulation of the systems involved.

The interactions of viruses and host cells is known to elicit the activation of multiple GTPases to promote the cytoskeletal remodeling required for breaching inter- and intracellular cellular barriers to infection as well as intracellular trafficking of internalized virions to allow replication. Most studies investigating the role of GTPases in viral interactions with host cells use traditional methods of active GTPase pull-down and detection by Western blot, which are slow, labor intensive and require large amounts of starting material. Newer, commercially available plate-based effector binding assays for detecting activated GTPases known as GLISA (Cytoskeleton, Inc.) require less material than western blot based assays, yet are still labor intensive; requiring freezing of aliquots, protein assays to ensure linearity and numerous binding and washing steps. Accordingly, most studies tend to focus on a limited subset of GTPases, which presents significant limitations when one wants to examine the broader spectrum of cell signaling space impinged upon by viral activity. Based on these considerations, we have developed a rapid, and quantitative flow cytometry-compatible, bead-based effector binding assay to analyze, in parallel, multiple GTPases that are activated in a single virus-infected cell sample.

Sepsis is a disease that now affects more than 900,000 patients with an estimated mortality rate of 30% in the US.[22-25A] Annual costs are estimated to exceed $20 billion.[26A] Severe trauma patients who survive the initial injury are at risk of developing sepsis syndrome and multiple organ failure.[24A, 25A, 27A] Systemic microvascular leakage, most likely due to the release of inflammatory, coagulation and fibrinolysis factors, is a signature of sepsis in trauma patients.[22A] An improved understanding of the clinical mechanisms of sepsis, including the roles of pathogens, sites of injury and patient heterogeneity, is urgently needed to enable better prevention, diagnosis, and treatment.[22A] The goal of this project is to address the need for timely and accurate differential diagnosis of sepsis and SIRS due to sterile inflammation. The pathophysiology of sepsis involves nearly all cell types, tissues, and organ systems, and has so far been associated with about 180 distinct potential biological markers.[4-8,A] These markers are organized as follows: vasoactive amines, vasoactive peptides, fragments of complement components, lipid mediators, cytokines, chemokines, and proteolytic enzymes involved in the coagulation and fibrinolytic system.[9,A] This level of heterogeneity continues to confound efforts to discover universally applicable models.

A heterogeneous patient population and a diverse ensemble of pathogenic bacteria highlight a cardinal problem in defining the pathogenesis of sepsis.[1-3,A] So far, about 180 potential biological markers of sepsis are known.[4-8,A] Their broad-spectrum applicability to sepsis and other pathologies has limited their early diagnostic utility.[9,A] New approaches accounting for the complexity of the inflammatory response and changes that occur during the course of sepsis are needed.

Small GTPases and their regulators, as they actuate and fine-tune pivotal molecular pathways, constitute vulnerable nodes of the cell. Their activities are associated with a a diverse range of biological functionality in health and disease, such as cancer[1-3], cardiovascular diseases or developmental diseases [6], and infections [4,5]. In disease, GTPAse signaling pathways are diverted during the onset or progression of the disease, and disorders in which the expression, regulation, or function of regulators is directly impaired by mutations. These include congenital diseases in which GTPase regulators carry missense mutations that impair their biochemical properties, and infections in which pathogens have created new regulators of their own to take command of host pathways. For some of these diseases, understanding the biochemical basis may help in discovering pharmaceuticals to correct these defects. Through evolution, bacterial pathogens have evolved a battery of toxins and virulence factors that target small GTPases that attenuate GTPases functions, in order to faciliatate host entry and dissemination.

1 Vega, F. M.; Ridley, A. J. Rho gtpases in cancer cell biology. *FEBS letters* 2008, 582, 2093-2101.
2. Iden, S.; Collard, J. G. Crosstalk between small gtpases and polarity proteins in cell polarization. *Nature reviews. Molecular cell biology* 2008, 9, 846-859.
3. Agola, J.; Jim, P.; Ward, H.; Basuray, S.; Wandinger-Ness, A. Rab gtpases as regulators of endocytosis, targets of disease and therapeutic opportunities. *Clinical genetics* 2012.
4. Lemichez, E.; Aktories, K. Hijacking of rho gtpases during bacterial infection. *Experimental cell research* 2013, 319, 2329-2336.
5. Aktories, K.; Schmidt, G. A new turn in rho gtpase activation by *Escherichia coli* cytotoxic necrotizing factors. *Trends in microbiology* 2003, 11, 152-155.
6. Cherfils, J.; Zeghouf, M. Regulation of small gtpases by gefs, gaps, and gdis. *Physiological reviews* 2013, 93, 269-309.

SUMMARY OF THE INVENTION

Early diagnosis of bacterial infection is critical for effective intervention in sepsis. We have employed active real time surveillance of factors that are enriched in the blood of trauma patients in proteomic and computational network analyses that link temporal changes in protein expression and hemostasis to identify novel clusters of potential targets for effective treatments, based on early detection and the development of new molecular-based therapies.

More specifically, we have determined the preclinical onset of infection by sensing bacteria-initiated hemostatic impairment[3,A, 10-13,A] and activation of RhoGTPases.[14-20,A] Hemostasis is a critical process that acts to seal breaches in the vascular system (clotting) either to prevent bleeding, and/or to block access for pathogens to the vascular system. Some bacteria are able to promote their dissemination by initiating fibrinolysis.[3,A, 10-13,A, 21,A] Thrombin is a versatile serine protease that is generated at sites of vascular injury and converts fibrinogen into fibrin monomers. [1:7] Endogenous fibrinolysis is a protective mechanism against lasting arterial and venous thrombotic occlusion, caused by fibrin clots. [8] Many gram-positive and gram-negative bacterial species can shift the fibrinolytic balance by inducing an increase in the concentration of plasmin in septic patients. [9-12] Fibrinolysis allows bacteria to disseminate beyond fibrin clot barriers that are meant to limit bacterial spread. [11-15] In addition, bacteria use virulence factors to modulate GTPase activity of host cells. [16-22] Therefore, our goal is to identify the onset of sepsis by analyzing, in parallel, the impairment of hemostasis and modulation of small molecule GTPases in serial blood samples collected from trauma patients with clinically confirmed sepsis. Our approach is to combine interdisciplinary expertise and tools to meet the goal of enabling better prevention, diagnosis, and treatment of sepsis. We have developed the necessary tools for measuring hemostatic impairment and activity of multiple RhoGTPases. [23-25] The Gtrap multiplex system developed is a unique tool that enables rapid measurement of the activity of GTP binding Rho proteins. [24].

1. Levi, M.; Keller, T. T.; van Gorp, E.; ten Cate, H. Infection and inflammation and the coagulation system. *Cardiovascular research* 2003, 60, 26-39.
2. Kumar, P.; Shen, Q.; Pivetti, C. D.; Lee, E. S.; Wu, M. H.; Yuan, S. Y. Molecular mechanisms of endothelial hyperpermeability: Implications in inflammation. *Expert Rev Mol Med* 2009, 11.
3. Escolar, G.; Bozzo, J.; Maragall, S. Argatroban: A direct thrombin inhibitor with reliable and predictable anticoagulant actions. *Drugs Today* 2006, 42, 223-236.
4. Carbajal, J. M.; Gratrix, M. L.; Yu, C. H.; Schaeffer, R. C., Jr. Rock mediates thrombin's endothelial barrier dysfunction. *American journal of physiology. Cell physiology* 2000, 279, C195-204.
5. Anwar, K. N.; Fazal, F.; Malik, A. B.; Rahman, A. Rhoa/rho-associated kinase pathway selectively regulates thrombin-induced intercellular adhesion molecule-1 expression in endothelial cells via activation of i kappa b kinase beta and phosphorylation of rela/p65. *J Immunol* 2004, 173, 6965-6972.
6. Sosothikul, D.; Seksarn, P.; Pongsewalak, S.; Thisyakorn, U.; Lusher, J. Activation of endothelial cells, coagulation and fibrinolysis in children with dengue virus infection. *Thrombosis and haemostasis* 2007, 97, 627-634.
7. Laine, O.; Makela, S.; Mustonen, J.; Huhtala, H.; Szanto, T.; Vaheri, A.; Lassila, R.; Joutsi-Korhonen, L. Enhanced thrombin formation and fibrinolysis during acute puumala hantavirus infection. *Thrombosis research* 2010, 126, 154-158.
8. Dubis, J.; Witkiewicz, W. The role of thrombin-activatable fibrinolysis inhibitor in the pathophysiology of bemostasis. *Adv Clin Exp Med* 2010, 19, 379-387.
9. McAdow, M.; Kim, H. K.; DeDent, A. C.; Hendrickx, A. P. A.; Schneewind, O.; Missiakas, D. M. Preventing *Staphylococcus Aureus* Sepsis Through the Inhibition of its Agglutination in Blood. *PLoS pathogens* 2011, 7.

10. Stearns-Kurosawa, D. J.; Osuchowski, M. F.; Valentine, C.; Kurosawa, S.; Remick, D. G. The pathogenesis of sepsis. *Annu Rev Pathol-Mech* 2011, 6, 19-48.
11. Rivera, J.; Vannakambadi, G.; Hook, M.; Speziale, P. Fibrinogen-binding proteins of gram-positive bacteria. *Thrombosis and haemostasis* 2007, 98, 503-511.
12. Bhattacharya, S.; Ploplis, V. A.; Castellino, F. J. Bacterial plasminogen receptors utilize host plasminogen system for effective invasion and dissemination. *Journal of biomedicine & biotechnology* 2012, 2012, 482096.
13. Vitiello, M.; Galdiero, S.; D'Isanto, M.; D'Amico, M.; Di Filippo, C.; Cantisani, M.; Galdiero, M.; Pedone, C. Pathophysiological changes of gram-negative bacterial infection can be reproduced by a synthetic peptide mimicking loop 17 sequence of *Haemophilus influenzae* porin. *Microbes and infection/Institut Pasteur* 2008, 10, 657-663.
14. Lahteenmaki, K.; Kuusela, P.; Korhonen, T. K. Bacterial plasminogen activators and receptors. *FEMS microbiology reviews* 2001, 25, 531-552.
15. van der Poll, T.; Herwald, H. The coagulation system and its function in early immune defense. *Thrombosis and haemostasis* 2014, 112.
16. Aktories, K.; Barbieri, J. T. Bacterial cytotoxins: Targeting eukaryotic switches. *Nature reviews. Microbiology* 2005, 3, 397-410.
17. Aktories, K.; Just, I. Clostridial rho-inhibiting protein toxins. *Current topics in microbiology and immunology* 2005, 291, 113-145.
18. Aktories, K.; Schmidt, G. A new turn in rho gtpase activation by *Escherichia coli* cytotoxic necrotizing factors. *Trends in microbiology* 2003, 11, 152-155.
19. Bokoch, G. M. Regulation of innate immunity by rho gtpases. *Trends Cell Biol* 2005, 15, 163-171.
20. Boquet, P.; Lemichez, E. Bacterial virulence factors targeting rho gtpases: Parasitism or symbiosis? *Trends Cell Biol* 2003, 13, 238-246.
21. Cherfils, J.; Zeghouf, M. Regulation of small gtpases by gefs, gaps, and gdis. *Physiological reviews* 2013, 93, 269-309.
22. Lemichez, E.; Aktories, K. Hijacking of rho gtpases during bacterial infection. *Experimental cell research* 2013, 319, 2329-2336.
23. Bondu-Hawkins, V.; Schrader, R.; Gawinowicz, M. A.; Mcguire, P.; Lawrence, D.; Hjelle, B.; Buranda, T. Elevated plasma cytokine, thrombin, and pai-1 levels in patients with severe hantavirus cardiopulmonary syndrome due to sin nombre virus *Viruses* 2014, in press.
24. Buranda, T.; Basuray, S.; Swanson, S.; Bondu-Hawkins, V.; Agola, J.; Wandinger-Ness, A. Rapid parallel flow cytometry assays of active gtpases using effector beads. *Analytical biochemistry* 2013, 144, 149-157.
25. Buranda, T.; Swanson, S.; Bondu, V.; Schaefer, L.; Maclean, J.; Mo, Z. Z.; Wycoff, K.; Belle, A.; Hjelle, B. Equilibrium and kinetics of sin nombre hantavirus binding at daf/cd55 functionalized bead surfaces. *Viruses-Basel* 2014, 6, 1091-1111.
26. Osuchowski, M. F.; Welch, K.; Siddiqui, J.; Remick, D. G. Circulating cytokine/inhibitor profiles reshape the understanding of the sirs/cars continuum in sepsis and predict mortality. *J Immunol* 2006, 177, 1967-1974.
27. Lvovschi, V.; Arnaud, L.; Parizot, C.; Freund, Y.; Juillien, G.; Ghillani-Dalbin, P.; Bouberima, M.; Larsen, M.; Riou, B.; Gorochov, G.; Hausfater, P. Cytokine profiles in sepsis have limited relevance for stratifying patients in the emergency department: A prospective observational study. *PloS one* 2011, 6, €28870.

In one embodiment, our invention provides a method of diagnosing sepsis or the prognosis of the severity of viral hemorrhagic fever ("VHF", e.g. hanviruses (hantavirus), ebola, Marburg, Lassa, and Crimean-Congo haemorrhagic fever, etc) infection in a subject, the method comprising the steps of:

(a) detecting the onset of sepsis and the severity of VHF infection-associated-GTPase biomarkers in a sample (preferably a plasma sample) obtained from the subject, wherein detecting comprises contacting the sample with a set of reagents (in preferred aspects, antibodies) which specifically bind to the sepsis associated-GTPase biomarkers;

(b) determining the presence and levels of at least one of the set of sepsis associated-GTPase biomarkers using flow cytometry or an immunoassay selected from the group consisting of ELISA, RIA, Western blot, luminescent immunoassay and fluorescent immunoassay; and (c) using the determined presence and levels of sepsis associated-GTPase biomarkers to diagnose sepsis or the severity of VHF infection in the individual.

In one embodiment, the level of at least one of the set of sepsis and VHF infection-associated-GTPase biomarkers is determined using a flow cytometry assay, the sample consists of cell lysates derived from the subject's plasma, and the flow cytometry assay comprises incubating GTPase effector coated beads with the cell lysates to detect those cell lysates that contain active, GTP-bound Ras, Rho, Ran, Arf and Rab GTPases, the GTPases being selectively recruited to beads that bear their cognate effector and being detected directly using fluorophore conjugated monoclonal antibodies specific for each GTPase or indirectly using secondary antibodies with fluorophore tags.

In certain embodiments, the flow cytometry assay is a multiplex flow cytometry assay in which distinct effectors are immobilized on beads of graded fluorescence intensities of a fluorophore with a fixed color (wavelength) and an extra set of effector free beads is used as a control for nonspecific binding.

In certain embodiments of the invention, multiplexed flow cytometry detects the presence and levels of sepsis and virus (e.g., hemorrhagic fever virus such as hanviruses (hantavirus), ebola, Marburg, Lassa and Crimean-Congo haemorrhagic fever, etc.) infection-associated-GTPase biomarkers using:

(a) a population of beads which have two or more sizes, which are labeled with a first fluorophore having a single wavelength (color) and a plurality of intensity levels and which are coupled to a plurality of effector proteins which bind to a plurality of cognate, infection-associated-GTPases;

(b) GTPase-specific antibodies which bind to effector protein-infection-associated-GTPase conjugates formed on the beads; and (c) detector antibodies which are specific to the GTPase-specific antibodies and which are labeled with a second fluorophore having a wavelength (color) which is different from that of the first fluorophore.

In certain embodiments of the invention:

(a) the effector proteins are selected from the group consisting of PAK-1 RBD (a Rac1 and Cdc42 effector), Raf-1 RBD, RalGDS, Rgl, Rgr Rlf, $\alpha,\beta,\gamma$ PI (3) kinases, AF6_RA1, AF6_RA2, Nore1 (Ras effector), Rhotekin-RBD (a Rho effector), RalGDS-RBD (a RAP1 effector protein), RILP-RBD (a Rab-7 effector protein), RAIN, RalGEF, RASSF1, RIN1, RIN2, PDZGEF, Tiam1, Epac1, Repac1, PLCε, scCYR1, spByr2 and Krit1; and (b) the first flurophore is a Rhodamine dye (preferably a red flurophore, e.g. Rhodamine Red-X) and the second fluorophore is a green flurophore (e.g. Alexa® 488).

In another preferred embodiment, the invention provides a method of using a multiplexed flow cytometric assay to diagnose sepsis or a virus infection in a subject, the method comprising:

(a) incubating a sample obtained from the subject with a population of beads which have two or more sizes, which are labeled with a first fluorophore having a single wavelength (color) and a plurality of intensity levels and which are coupled to a plurality of effector proteins which bind to a plurality of cognate, infection-associated-GTPases;

(b) incubating the beads with primary GTPase-specific antibodies;

(c) mixing the incubated fluorescent beads of step (b) with secondary antibodies which are specific to primary GTPase-specific antibodies and which are labeled with a second fluorophore having a wavelength (color) which is different from that of the first fluorophore; and (d) measuring the fluorescence intensity of the mixed beads of step (c) using flow cytometry to determine the presence and level of infection-associated-GTPase in the sample.

In certain embodiments, multiplexed assays used in methods of the invention can be conducted at speed of about 40 wells per minute and the assay can process at least 96 or 384 well-plates in a time period of between about 2 to about 15 minutes, more preferably in about 3 to about 12 minutes.

In certain embodiments, a subject's sepsis or virus infection diagnosis includes the additional steps of:

(a) analyzing the impairment of hemostasis and/or bacterial infection-related increase in thrombogenesis and fibrinolysis by measuring thrombin and/or plasmin levels in a blood sample obtained from the subject; and (b) comparing measured thrombin and/or plasmin levels to control thrombin and/or plasmin levels determined in a healthy control subject;

wherein measured thrombin and/or plasmin levels which exceed corresponding control levels are indicative of the onset or progression of sepsis or virus infection.

Analyses of hemostasic and/or bacterial infection-related increase in thrombogenesis and fibrinolysis can be conducted in parallel with multiplexed flow cytometry assays described herein. An electric cell-substrate impedance sensing (ECIS) cell-based assay can be used to ascertain thrombin and/or plasmin-associated disruption of cellular function in cells exposed to a sample of the subject's plasma. See, for example, Bondu, et al., *Viruses,* 7, 559-589 (2015), relevant portions of which are incorporated by reference herein. Preferably, ECIS cells are plated at confluence in electrode-containing dishes, cellular impedance is measured continuously at a single frequency, increasing cell barrier function is confirmed by increasing resistance, cells are exposed to a sample of the subject's plasma and any decrease in cell monolayer resistance is correlated to sepsis-associated thrombin and/or plasmin-associated disruption of cellular function.

One or more steps of the novel diagnostic methods described herein can be conducted in a high-throughput fashion and/or can be done in silico.

One embodiment of the invention diagnoses the degree of severity of VHF infection.

The active GTPase effector trap flow cytometry assay (G-trap) described and claimed herein has significant advantages over standard pulldown techniques, including: (1) the fact that G-trap enables rapid measurement, sensitivity and analysis with results within four hours, compared to days required for other assays; (2) G-trap uses small samples e.g. <100,000 cells grown in a 48 well plate, well below the requisite minimum of $2 \times 10^6$ cells for single ELISA based measures; (3) G-trap can measure multiple GTPases from a single lysate using a multiplex approach (FIG. 11A), whereas conventional assays require the entire lysate for measurement of a single GTPase, and (4) G-trap facilitates replicate measures on scarce cell samples.

Thus, diagnostic methods of the invention improve clinical care by identifying a manageable basis set of response factors in the patient's blood that can be monitored in real time in order to enable clinical intervention during a limited window of effective therapy. The diagnostic methods of the invention are also useful to monitor therapeutic effect of intervention and prognosis for survival.

These and other aspects of the invention are described further in the Detailed Description of the Invention.

DETAILED DESCRIPTION OF THE INVENTION

Figure 1:
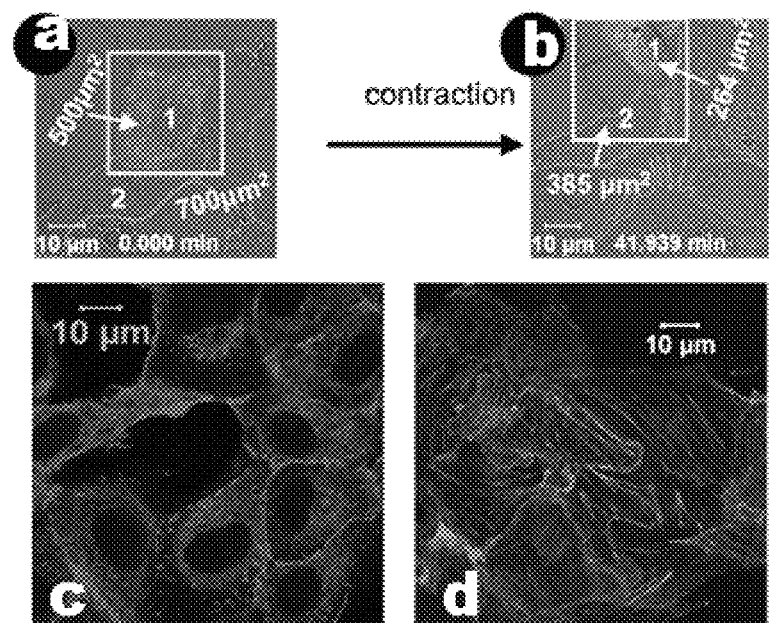
FIG. 1: a, b, c, d, e, f shows that UV-killed $SNV^{R18}$ induces vigorous remodeling of the actin cytoskeleton of Vero E6 cells, causing loss of cell adhesion. a. Confocal microscopy images of resting Vero E6 cells monolayers transiently transfected with the cell adhesion marker, paxillin GFP. Individual cells are delineated with lines. Cells designated 1 and 2 are also defined by their surface area. The white square was included as size reference for cell 1. b. Time lapse frame taken 42 min after cells were exposed to 10,000 $SNV^{R18}$ particles/cell. $SNV^{R18}$ induces remodeling of the actin cytoskeleton of Vero E6 cells. Cells designated 1 and 2 and surrounding cells shrank in size and experience loss of cell adhesion to each other and the coverslip. c. Resting Vero E6 cells stained showing actin stained with Alexa Fluor 488® phalloidin. d. RhoA induced F-actin stress fibers are shown 15 min after SNV exposure. e. EFCB assay for virus induced GTP Rac1 and GTP RhoAGTP. Vero E6 cells were serum starved for 24 hours and activated with 10,000 $SNV^{R18}$/cell. Rac1 and RhoA were measured on PAK1 and Rhotekin beads at 3 and 20 min after virus exposure. The errors represent standard deviations of 3 separate measurements. f. Vero E6 cells were stimulated with: calpeptin (calpptn) to activate RhoA, EGF to activate Rac1 and RhoA, NSC23766 (NSC) to suppress Rac1 activity. Control samples (rest) were mock-treated with 0.1% DMSO to account for compound solvent. The errors represent standard deviation of 3 independent experiments measured in duplicate at a time.
Figure 1:
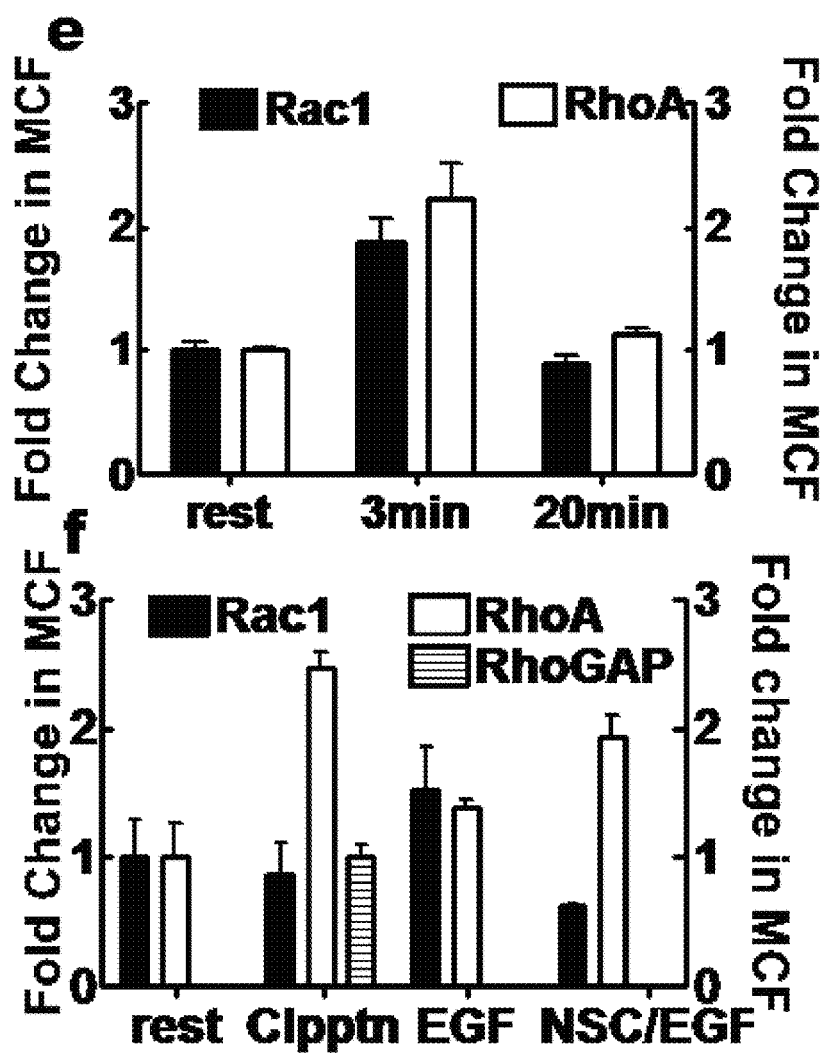
Figure 2:
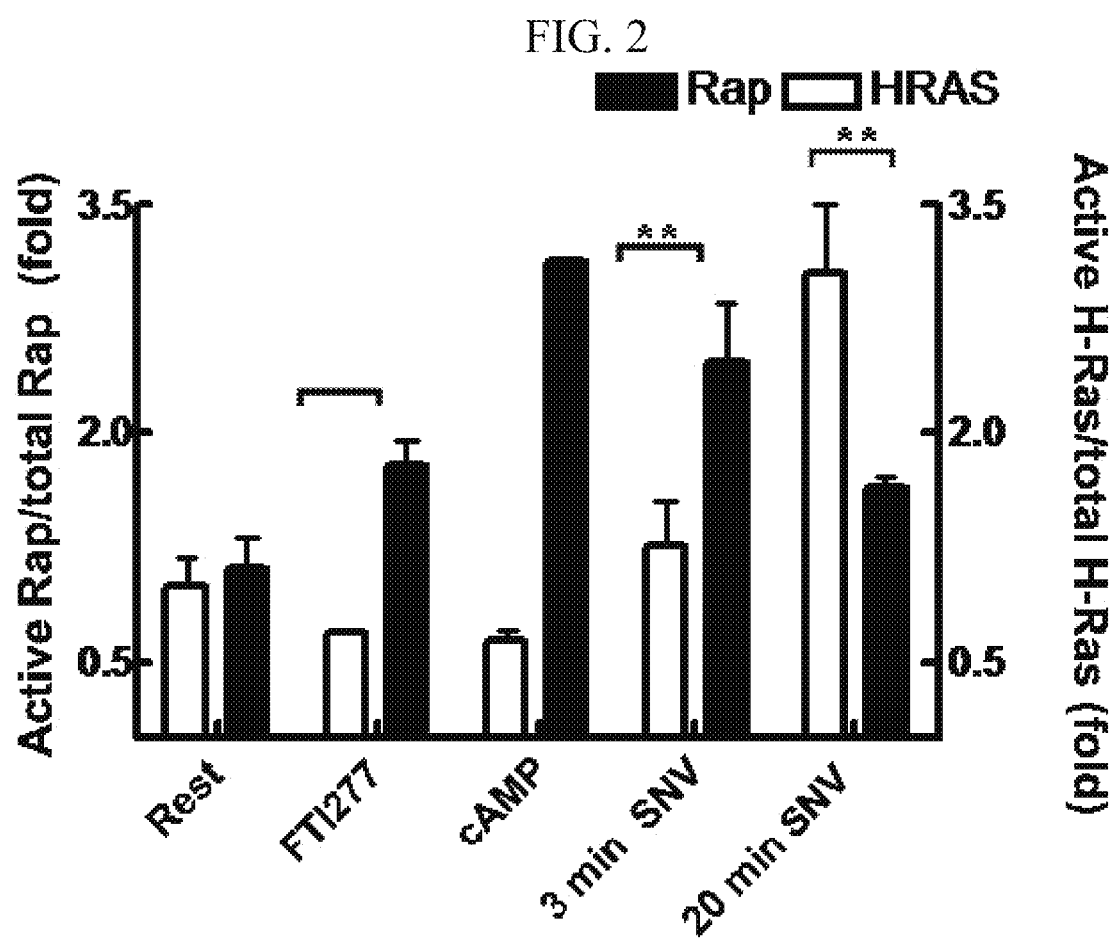
FIG. 2 shows that Rap1 and H-Ras are sequentially activated by $SNV^{R18}$ in Vero E6 cells. Vero E6 cells were serum starved for 24 hours and activated with 10,000 $SNV^{R18}$/cell. Rap1 and H-Ras were measured on Ra1 and Raf-functionalized beads at 3 and 20 min after virus exposure. Cells were treated with FTI277 a specific inhibitor of H-Ras and 8-Cpt-2m-cAMP (CAMP) an activator of Rap1. Inhibition of H-Ras induced a near 2-fold increase active Rap1, while activation of Rap1 decreased basal levels of H-Ras. In virus-activated cells, Rap1 and H-Ras were activated sequentially. Rap 1 was activated within the first 3 min and subsequently deactivated at 20 mins and H-Ras was fully active at 20 min. Error bars represent standard deviations 3 separate measurements.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

"Sepsis and/or viral hemorrhagic fever-associated GTPases" include but are not limited to RhoA, Rac1, and Cdc42 and the isoforms thereof.

"Sepsis-associated" and "Viral hemorrhagic fever associated" GTPase biomarkers" are described hereinafter. Non-limiting examples of sepsis and Viral hemorrhagic fever-associated GTPase biomarkers include PAK-1 RBD-Rac1 conjugates and PAK-1 RBD-Cdc42 conjugates, Raf-1 RBD-Ras conjugates, Rhotekin-RBD-Rho conjugates, RalGDS-RBD-RAP1 conjugates and RILP-RBD-Rab-7 conjugates, among others.

"GTPase effectors" are molecules which bind to GTPases and effect their function. GTPase effectors for use in the present invention include PAK-1 RBD (a Rac1 and Cdc42 effector), Raf-1 RBD, RalGDS, Rgl, Rgr Rlf, $\alpha,\beta,\gamma$ PI (3) kinases, AF6_RA1, AF6_RA2, Nore1 (Ras effector), Rhotekin-RBD (a Rho effector), RalGDS-RBD (a RAP1 effector protein), RILP-RBD (a Rab-7 effector protein), RAIN, RalGEF, RASSF1, RIN1, RIN2, PDZGEF, Tiam1, Epac1, Repac1, PLC$\epsilon$, scCYR1, spByr2 and Krit1, among numerous others.

The GTPase RhoA effectors include:
Cit, Cnksr1, Diaph1, Diaph2, DgkQ, FinA, KcnA2, Ktn1, Rtkn1, Rtkn2, Rhpn1, Rhpn2, Itprl1, PlcG1, PI-5-p5K, Pld1, Pkn1, Pkn2, Rock1, Rock2, PrkcA and Ppp1r12A.

The GTPase Rac1 effectors include Sra1, IRSp53, PAK1, PAK2 and PAK3.

The GTPase Cdc42 effectors include Wiskott-Aldrich syndrome protein, N-WASP, IRSp53, Dia2, Dia3, ROCK1 and ROCK2.

In a preferred embodiment, effector proteins are selected from the group consisting of PAK-1 RBD (a Rac1 and Cdc42 effector), Raf-1 RBD, (a Ras effector), Rhotekin-RBD (a Rho effector), RalGDS-RBD (a RAP1 effector protein) and RILP-RBD (a Rab-7 effector protein).

Glutathione (GSH), a ubiquitous tripeptide, is an important cellular constituent, and measurement of reduced and oxidized glutathione is a measure of the redox state of cells. Glutathione-S-transferase (GST) fusion proteins bind naturally to beads derivatized with glutathione, and elution of such bead-bound fusion proteins with buffer containing millimolar glutathione is a commonly used method of protein purification. Many protein-protein interactions have been established by using GST fusion proteins and measuring binding of fusion protein binding partners by GST pulldown assays. Tessema, et al., "Glutathione-S-transferase-green fluorescent protein fusion protein reveals slow dissociation from high site density beads and measures free GSH", *Cytometry,* 69A: 326-334. doi: 10.1002/cyto.a.20259.

As explained in Example 3 hereinafter, to simplify bacterial expression and purification of effector proteins, it is preferable to use only the GTPase binding domains (RBD) of cognate effectors. In preferred embodiments, effector coated beads are incubated with cell lysates that contain active, GTP-bound Ras, Rho and Rab GTPases. The GTPases are selectively recruited to beads that bear the cognate effector and are detected directly using fluorophore conjugated monoclonal antibodies specific for each GTPase or indirectly using secondary antibodies with fluorophore tags. In a non-limiting flow cytometry example explained further hereinafter (see e.g. Example 3), glutathione beads can functionalized with effectors for Rap1 (GST RalGDS-RBD) and H-Ras (Raf-1 RBD) to simultaneously assay activated Rap1 and H-Ras GTPases from cell lysates. As illustrated in Example 1, GST (Glutathione S-Transferase) conjugates of various GTPase-effector proteins can be bound to suspensions of GSH beads to in order to form molecular assemblies necessary for capturing GTP-bound GTPases from cell lysates. The characteristic kinetic and equilibrium binding constants of glutathione-S-transferase (GST) fused to Green fluorescent protein (GFP), can be used to establish optimal stoichiometric mixtures of GSH beads and specific GST effector fusion proteins for desired site occupancies of the GST effector proteins used in the flow cytometry assays.

"Reagents which specifically bind to the sepsis (or Viral hemorrhagic fever) associated-GTPase biomarkers" include GTPase biomarker protein purification reagents, antibodies to GTPase biomarker polypeptides or peptides thereof, nucleic acid primers specific for genes which express GTPase biomarkers, arrays of GTPase biomarker-related nucleic acid probes, signal producing system reagents, etc. Useful reagents include arrays that comprise probes, e.g. arrays of antibodies or arrays of oligonucleotides; or other reagents that may be used to detect the expression of GTPase biomarkers. Those of ordinary skill in the art know how to identify and make the aforementioned reagents. See e.g. Spiegel, et al., Direct Targeting of Rab-GTPase-Effector Interactions, *Angewandte Chemie* International Edition Volume 53, Issue 9, pages 2498-2503 Feb. 24, 2014; Kahn, et al., "Structural Biology of Arf and Rab GTPases' Effector Recruitment and Specificity", *Structure* 21, Aug. 6, 2013.

The basics of flow cytometry and multiplexed flow cytometry are well-known to those of ordinary skill in the art. See e.g. the technical description and supporting references cited at: http://www.einstein.yu.edu/research/facilities/facs/page.aspx?id=22632. A useful summary of certain types of multiplexed flow cytometry assays is provided in U.S. Patent Application Document No. 20140206008 as follows. "Luminex MultiAnalyte Profiling (xMAP) technology, previously known as FlowMetrix and LabMAP (Elshal and McCoy, 2006), is a multiplex bead-based flow cytometric assay that is gaining recognition as a method for analyte quantitation. This technology utilizes 5.6-micron polystyrene beads that are internally dyed with different intensities of red and infrared fluorophores. Currently there are 100 beads, each with a unique spectral make up which allows the mixing of several bead sets and, in theory, enabling the detection of up to 100 different analytes per assay (Vignali, D. A. A., J Immunol Methods, 243:243-255 (2000)). The beads can be bound by various capture reagents such as antibodies, oligonucleotides, and peptides, therefore facilitating the quantification of various proteins, ligands, DNA and RNA (Fulton, R. J. et al., Clin Chem, 43:1749-1756 (1997); Kingsmore, S. F., Nat Rev Drug Discov, 5:310-321 (2006); Nolan, J. P. and Mandy, F., Cytometry Part A, 69A: 318-325 (2006)). The assays are run on a 96-well plate format, followed by detection on a Luminex 100 instrument. As the beads run through the instrument, the internal dyes are excited by a laser which results in the classification of each bead. Another laser excites the reporter dye which is directly proportional to the amount of analyte bound to each bead (Vignali, D. A. A., J Immunol Methods, 243:243-255 (2000); Ray, C. A. et al., J Pharma Biomed Anal, 36:1037-1044 (2005)). The resulting fluorescence is recorded by the instrument which then provides the median fluorescence unit obtained from measuring 100 beads. Luminex xMAP technology has many applications including protein expression profiling, gene expression profiling, genotyping, immunodiagnostics, and genetic disease diagnostics. Although single-plex bead-based assays have been available for a long time; technological developments have enhanced the development of multiplex bead-based assays enabling the utilization of this method for quantitation of a panel of protein markers simultaneously (Linkov, F. et al., Cancer Epidemiol Biomarkers Prev, 16:102-107 (2007); Prabhakar, U. et al., J Immunol Methods, 260:207-218 (2002)). The advantage of Luminex xMAP technology lies in its high sensitivity, throughput and efficiency (Vignali, D. A. A., J Immunol Methods, 243:243-255 (2000); DuPont, N. C. et al., J Reprod Immunol, 66:175-191 (2005)). Significant reduction in time and costs results from multiplexing when compared to ELISA. ELISA is more expensive and time-consuming to perform when many proteins are to be measured using many single-plex protein specific assays (de Jager, W. and Rijkers, G. T., Methods, 38:294-303 (2006)). On the contrary, many protein analytes can be measured by the multiplexed bead-based assay with a single plate. This is extremely important for clinical studies where sample volumes are limited (Liu, M. Y. et al., Clin Chem, 51:1102-1109 (2005)). Bead-based assay is more accurate because the median fluorescence is obtained from the readout of at least 50 to 100 beads. Thus each bead is functioning as a duplicate, making this assay more reliable (Vignali, D. A. A., J Immunol Methods, 243:243-255 (2000); Kettman, J. R. et al., Cytometry, 33:234-243 (1998))."

Multiplexed flow cytometric assays of the invention can use, e.g. 2, 4, 8, 16, 32, 64, 128, 256, or 12, 24, 36, 48 or 60 distinct sets of fluorescent spheres (beads) or microspheres and a standard benchtop flow cytometer interfaced with a personal computer containing a digital signal processing board and programmed with a variety of operating software. Individual sets of beads or microspheres (microbeads) can be modified with reactive components such as antigens, antibodies, or oligonucleotides, and then mixed to form a multiplexed assay set. The digital signal-processing hardware and software control the flow cytometer and perform real-time data processing, allowing multiple independent reactions to be analyzed simultaneously in qualitative and quantitative immunoassays for multiple serum proteins in both capture and competitive inhibition assay formats.

Multiplexed beads can be assigned to two or more groups which perform distinct assays and are distinguished by characteristics that enable distinct detection of assay group results. Bead size can be a distinguisher; beads are defined by distinct sub-sizes and are grouped into distinct sub-ranges, e.g. 2, 4, 8, 16, 32, 64, 128 sub-ranges, each of which conducts a unique assay. Particle size sub-ranges and mean diameter spacing of adjacent sub-ranges permit differentiation of the sub-ranges. Preferred sub-ranges can vary by about +/−5% CV or less of the mean diameter, where CV is the coefficient of variation and is defined as the standard deviation of the particle diameter divided by the mean particle diameter times 100 percent. Minimum spacing between mean diameters among the various sub-ranges can depend on bead size distribution and flow cytometry sensitivity. Fluorescence differentiation is achieved by using various fluorescent materials in the beads having different fluorescent emission spectra. Fluorescence can distinguish sub-groups and serve as an assay detector.

"A gate in cytometry is a set of value limits (boundaries) that serve to isolate a specific group of cytometric events from a large set. Gates can be defined by discrimination analysis, or can simply be drawn around a given set of data points on a print-out and then converted to a computer-useful form. Gates can be implemented with a physical blinder. Gates may be used either to selectively gather data or to segregate data for analysis. Gates are divided mathematically into inclusive gates and exclusive gates. Inclusive gates select data that falls within the limits set, while exclusive gates select data that falls outside the limits. A live gate is a term used for a process that prevents the acquisition by the computer of non-selected data from the flow cytometer. (see, for example, Osborne, G. W. (2000) "Regions and Gates" Flow Cytometry Software Workshop: 2000, page 3)." See U.S. Patent Application Document No. 20120083007.

Other types of assays besides flow cytometric assays (e.g. ELISA, RIA, Western blot, luminescent immunoassay and fluorescent immunoassay) can be used to measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, *Antibodies: A Laboratory Manual*, Cold Spring Harbor Laboratory Press, Cold Spring Harbor, N.Y., 1999 and Edwards R, *Immunodiagnostics: A Practical Approach*, Oxford University Press, Oxford; England, 1999). All these detection techniques may also be employed in the format of microarrays, protein-arrays, antibody microarrays, tissue microarrays, electronic biochip or protein-chip based technologies (see Schena M., *Microarray Biochip Technology*, Eaton Publishing, Natick, Mass., 2000).

Certain diagnostic and screening methods of the present invention utilize an antibody, preferably, a monocolonal antibody, capable of specifically binding to a protein as described herein or active fragments thereof. The method of utilizing an antibody to measure the levels of protein allows for non-invasive diagnosis of the pathological states of sepsis or Viral hemorrhagic fever infections. In a preferred embodiment of the present invention, the antibody is human or is humanized. The preferred antibodies may be used, for example, in standard radioimmunoassays or enzyme-linked immunosorbent assays or other assays which utilize antibodies for measurement of levels of protein in sample. In a particular embodiment, the antibodies of the present invention are used to detect and to measure the levels of protein present in a plasma sample.

Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a disease related protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

Antibodies or antibody fragments employed in such screening tests may be free in solution, affixed to a solid support, borne on a cell surface, or located intracellularly. The blocking or reduction of biological activity or the formation of binding complexes between the disease-related protein and the agent being tested can be measured by methods available in the art.

Other techniques for drug screening which provide for a high throughput screening of compounds having suitable binding affinity to a protein, or to another target polypeptide useful in modulating, regulating, or inhibiting the expression and/or activity of a disease, are known in the art. For example, microarrays carrying test compounds can be prepared, used, and analyzed using methods available in the art. See, e.g., Shalon, D. et al., 1995, International Publication No. WO95/35505, Baldeschweiler et al., 1995, International Publication No. WO95/251116; Brennan et al., 1995, U.S. Pat. No. 5,474,796; Heller et al., 1997, U.S. Pat. No. 5,605,662.

Other screening techniques, which can also serve to determine the presence and levels of sepsis associated-GTPase biomarkers are well-known to those or ordinary skill in the art. See, e.g., Enna et al., eds., 1998, Current Protocols in Pharmacology, John Wiley & Sons, Inc., New York N.Y. Assays will typically provide for detectable signals associated with the binding of the compound to a protein or cellular target. Binding can be detected by, for example, fluorophores, enzyme conjugates, and other detectable labels well known in the art. The results may be qualitative or quantitative.

To determine specific binding, various immunoassays may be employed for detecting, for example, human or primate antibodies bound to the cells. Thus, one may use labeled anti-hIg, e.g., anti-hIgM, hIgG or combinations thereof to detect specifically bound human antibody. Various labels can be used such as radioisotopes, enzymes, fluorescers, chemiluminescers, particles, etc. There are numerous commercially available kits providing labeled anti-hIg, which may be employed in accordance with the manufacturer's protocol.

In one embodiment, a kit can comprise: (a) at least one reagent which is selected from the group consisting of (i) reagents that detect a transcription product of the gene coding for a protein marker as described herein (ii) reagents that detect a translation product of the gene coding for proteins, and/or reagents that detect a fragment or derivative or variant of said transcription or translation product; (b) instructions for diagnosing, or prognosticating a disease, or determining the propensity or predisposition of a subject to develop such a disease or of monitoring the effect of a treatment by determining a level, or an activity, or both said level and said activity, and/or expression of said transcription product and/or said translation product and/or of fragments, derivatives or variants of the foregoing, in a sample obtained from said subject; and comparing said level and/or said activity and/or expression of said transcription product and/or said translation product and/or fragments, derivatives or variants thereof to a reference value representing a known disease status (patient) and/or to a reference value representing a known health status (control) and/or to a reference value; and analyzing whether said level and/or said activity and/or expression is varied compared to a reference value representing a known health status, and/or is similar or equal to a reference value representing a known disease status or a reference value; and diagnosing or prognosticating a disease, or determining the propensity or predisposition of said subject to develop such a disease, wherein a varied or altered level, expression or activity, or both said level and said activity, of said transcription product and/or said translation product and/or said fragments, derivatives or variants thereof compared to a reference value representing a known health status (control) and/or wherein a level, or activity, or both said level and said activity, of said transcription product and/or said translation product and/or said fragments, derivatives or variants thereof is similar or equal to a reference value and/or to a reference value representing a known disease stage, indicates a diagnosis or prognosis of a disease, or an increased propensity or predisposition of developing such a disease, a high risk of developing signs and symptoms of a disease.

Reagents that selectively detect a transcription product and/or a translation product of the gene coding for proteins can be sequences of various length, fragments of sequences, antibodies, aptamers, siRNA, microRNA, and ribozymes. Such reagents may be used also to detect fragments, derivatives or variants thereof.

The term "patient" or "subject" is used throughout the specification within context to describe an animal, generally a mammal, especially including a domesticated animal and preferably a human, to whom a treatment, including prophylactic treatment (prophylaxis) is provided. For treatment of those infections, conditions or disease states which are specific for a specific animal such as a human patient, the term patient refers to that specific animal. In most instances, the patient or subject is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

Sepsis is a clinical syndrome that complicates severe infection. It is characterized by the cardinal signs of inflammation (vasodilation, leukocyte accumulation, increased microvascular permeability) occurring in tissues that are remote from the infection. Systemic inflammatory response syndrome (SIRS) is an identical clinical syndrome that complicates a noninfectious insult (e.g., acute pancreatitis, pulmonary contusion). Current theories about the onset and progression of sepsis and SIRS focus on dysregulation of the inflammatory response, including the possibility that a massive and uncontrolled release of proinflammatory mediators initiates a chain of events that lead to widespread tissue injury. This response can lead to multiple organ dysfunction syndrome (MODS), which is the cause of the high mortality associated with these syndromes.

Sepsis is typically associated with a bacterial infection and is characterized by a whole-body inflammatory state (SIRS) and the presence of a known or suspected infection. The body may develop this inflammatory response by the immune system to bacteria presence in the blood, urine, lungs, skin, or other tissues. Sepsis is also referred to as "blood poisoning" or septicemia. Severe sepsis is the systemic inflammatory response, plus infection, plus the presence of at least one organ dysfunction. Septicemia (also sometimes referred to as bacteremia) refers to the presence of pathogenic organisms in the bloodstream, leading to sepsis.

An *S. aureus* infection can cause septic arthritis. Bacterial arthritis (or septic arthritis) is a rapidly progressive and highly destructive joint disease in humans. Clinical symptoms of septic arthritis include red, swollen, warm, painful and dysfunctional joints. Septic arthritis develops when bacteria spread through the bloodstream to a joint and it may also occur when the joint is directly infected with a microorganism from an injury or during surgery. The most common sites for this type of infection are the knee and hip.

In the United States, sepsis is the second-leading cause of death in non-coronary ICU patients, and the tenth-most-common cause of death overall according to data from the Centers for Disease Control and Prevention (the first being heart disease). Sepsis is common and also more dangerous in elderly, immunocompromised, and critically ill patients. It occurs in 1-2% of all hospitalizations and accounts for as much as 25% of intensive-care unit (ICU) bed utilization. It is a major cause of death in intensive-care units worldwide, with mortality rates that range from 20% for sepsis to 40% for severe sepsis to >60% for septic shock. Septic shock is a medical emergency caused by decreased tissue perfusion and oxygen delivery as a result of severe infection and sepsis, though the microbe may be systemic or localized to a particular site. It can cause multiple organ dysfunction syndrome (formerly known as multiple organ failure) and death. Its most common victims are children, immunocompromised individuals, and the elderly, as their immune systems cannot deal with the infection as effectively as those of healthy adults. Frequently, patients suffering from septic shock are cared for in intensive care units. The mortality rate from septic shock is approximately 25%-50%. See United States Patent Application Document No. 20140162978.

Adequate management of septic patients is often complicated by delay in administering therapy after sepsis has been recognized. Every hour delay in the administration of appropriate antibiotic therapy there is associated with a significant rise in mortality.

"Sepsis" as used herein includes all of the aforementioned septic states, conditions and clinical symptoms, e.g. "sepsis" includes but is not limited to systemic inflammatory response syndrome (SIRS), septicemia, septic arthritis and septic shock.

Hantaviruses belong to the bunyavirus family of viruses. There are five genera within the family: bunyavirus, phlebovirus, nairovirus, tospovirus, and hantavirus. Each is made up of negative-sensed, single-stranded RNA viruses. All these genera include arthropod-borne viruses, with the exception of hantavirus, which is rodent-borne. Like other members of the bunyavirus family, hantaviruses are enveloped viruses with a genome that consists of three single-stranded RNA segments designated S (small), M (medium), and L (large), All hantaviral genes are encoded in the negative (genome complementary) sense. The S RNA encodes the nucleocapsid (N) protein. The M RNA encodes a polyprotein that is cotranslationally cleaved to yield the envelope glycoproteins G1 and G2. The L RNA encodes the L protein, which functions as the viral transcriptase/replicase. Within virions, the genomic RNAs of hantaviruses are thought to complex with the N protein to form helical nucleocapsids, which circularize due to sequence complementarity between 5' and 3' terminal sequences of each genomic segment.

Sin Nombre virus (SNV), a hantavirus, was first isolated from rodents collected on the premises of one of the initial HPS patients in the Four Corners region. Isolation was achieved through blind passage in *Peromyscus maniculatus* and subsequent adaptation to growth in Vero E6 cells. Additional viral strains have also been isolated from *P. maniculatus* associated with a fatal case in California and *P. leucopus* from the vicinity of probable infection of a New York case. Black Creek Canal virus was isolated from *S. hispidus* collected near the residence of a human case in Dade County, Florida.

Several members of the hantavirus genus cause different forms of hemorrhagic fever with renal syndrome (HFRS), an ancient disease first described in Russia in 1913. The four viruses that are associated with HFRS, each named for the region from where they were first isolated, have different primary rodent hosts: *Apodemus agrarius* (the striped field mouse) for Hantaan virus, *Rattus norvegicus* (the Norway rat) and *Rattus rattus* (the black rat) for Seoul virus, *Clethrionomys glareolus* (the bank vole) for Puumala virus, and *Apodemus flavicollis* (the yellow-necked field mouse) for Dobrava virus. Hantaan virus from Korea and Dobrava virus from Slovenia are associated with a severe form of HFRS characterized by renal failure that can precede pulmonary edema and disseminated intravascular coagulation (DIC), with estimated mortality rates of 5% to 15%. A moderate form of HFRS caused by Seoul virus (which, along with its host, is distributed worldwide) is responsible for thousands of Eurasian cases annually. Serologic evidence for infection with Seoul-like hantaviruses has been found in rodents in major cities of the United States, and this virus was recently implicated in human cases of HFRS in Baltimore. One report has also associated Seoul virus with chronic renal disease. A mild form of HFRS, caused by Puumala virus, is responsible for nephropathia epidemica in Scandinavia, with an estimated mortality rate of 1% to 3%.

As used herein, a "hantavirus infection" includes any infection or disorder associated with a hantavirus such as a Sin Nombre virus, including but not limited to hantavirus hemorrhagic fever with renal syndrome (HFRS) (a group of clinically similar illnesses caused by species of hantaviruses from the family Bunyaviridae) or Hantavirus pulmonary syndrome (HPS) (an often fatal pulmonary disease which in the United States is caused by the Sin Nombre virus carried by deer mice).

The term "Hemorrhagic fever virus" refers to a virus which causes hemorrhagic fever from four distinct families: arenaviruses, filoviruses, bunyaviruses and flaviviruses and includes the hantaviruses as described above, ebola virus, Marburg virus, Lassa virus and Crimean-Congo hemorrhagic fever viruses.

The term "compound" is used herein to describe any specific compound or bioactive agent disclosed herein, including any and all stereoisomers (including diasteromers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein.

A "control" as used herein may be a positive or negative control as known in the art and can refer to a control cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. For instance, as can be appreciated by a skilled artisan, a control may comprise data from one or more control subjects that is stored in a reference database. The control may be a subject who is similar to the test subject (for instance, may be of the same gender, same race, same general age and/or same general health) but who is known to not have a fibrotic disease. As can be appreciated by a skilled artisan, the methods of the invention can also be modified to compare a test subject to a control subject who is similar to the test subject (for instance, may be of the same gender, same race, same general age and/or same general health) but who is known to express symptoms of a disease. In this embodiment, a diagnosis of a disease or staging of a disease can be made by determining whether protein or gene expression levels as described herein are statistically similar between the test and control subjects.

Purely by way of example, comparing measured levels of an infection-associated-GTPase in a sample to corresponding control levels, or comparing measured thrombin and/or plasmin levels to control thrombin and/or plasmin levels determined in a healthy control subject, and determining that a subject suffers from sepsis or a hantavirus infection or that a subject's sepsis or hantavirus infection is progressing, can include determinations based on comparative level differences of about between about 5-10%, or about 10-15%, or about 15-20%, or about 20-25%, or about 25-30%, or about 30-35%, or about 35-40%, or about 40-45%, or about 45-50%, or about 50-55%, or about 55-60%, or about 60-65%, or about 65~ 70%, or about 70-75%, or about 75-80%, or about 80-85%, or about 85-90%, or about 90-95%, or about 95-100%, or about 100-110%, or about 110-120%, or about 120-130%, or about 130-140%, or about 140-150%, or about 150-160%, or about 160-170%, or about 170-180%, or about 180-190%, or 190-200%, or 200-210%, or 210-220%, or 220-230%, or 230-240%, or 240-250%, or 250-260%, or about 260-270%, or about 270-280%, or about 280-290%, or about 290-300%, or differences of about between about ±50% to about ±0.5%, or about ±45% to about: ±1%, or about ±40% to about ±1.5%, or about ±35% to about ±2.0%, or about ±30% to about ±2.5%, or about ±25% to about ±3.0%, or about ±20% to about ±3.5%, or about ±15% to about ±4.0%, or about ±10% to about ±5.0%, or about ±9% to about ±1.0%, or about ±8% to about ±2%, or about ±7% to about ±3%, or about ±6% to about ±5%, or about ±5%, or about ±4.5%, or about ±4.0%, or about ±3.5%, or about ±3.0%, or about ±2.5%, or about ±2.0%, or about ±1.5%, or about ±1.0%.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

A "biological sample" can be a tissue sample or a cell sample, and most preferably is a plasma sample.

As used herein, the terms "nucleotide" and "polynucleotide" refer respectively to monomeric or polymeric form of nucleotides of any length, either ribonucleotides or deoxynucleotides, and include both double- and single-stranded DNA and RNA. A nucleotide or polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A nucleotide or polynucleotide can be linear or circular in topology. A nucleotide or polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

A "ligand" can be any natural or synthetic moiety, including but not limited to a small molecule, an antibody, a nucleic acid, an amino acid, a protein (e.g. an enzyme) or a hormone that binds to a cell, preferably at a receptor (binding site) located on the surface of the cell. The term "ligand" therefore includes any targeting active species (compound or moiety, e.g. antigen) which binds to a moiety (preferably a receptor) on, in or associated with a cell. In some embodiments, a ligand is a peptide, a polypeptide including an antibody or antibody fragment, an aptamer, or a carbohydrate, among other species which bind to a targeted cell.

"Binding site" as used herein is not limited to receptor protein surface areas that interact directly with ligands, but also includes any atomic sequence, whether or not on the surface of a receptor, that is implicated (by affecting conformation or otherwise) in ligand binding. A purely illustrative list of binding sites include those targeted by detector antibodies which are specific to the GTPase-specific antibodies, and those targeted by GTPase-specific antibodies, as illustrated by the antibodies described in the Examples herein and as otherwise identifiable by techniques which are well-known to those of ordinary skill in the art.

Diagnostic methods of the present invention utilize an antibody, preferably, a monocolonal antibody, capable of specifically binding to a protein as described herein or active fragments thereof. The method of utilizing an antibody to measure the levels of protein allows for non-invasive diagnosis of the pathological states of sepsis and/or a hantavirus infection. In a preferred embodiment of the present invention, the antibody is human or is humanized. Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a disease related protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

"Fluorophores" small molecule fluors and proteinaceous fluors (e.g. green fluorescent proteins and derivatives thereof). Useful fluorophores include, but are not limited to, 1,1'-diethyl-2,2'-cyanine iodide, 1,2-diphenylacetylene, 1,4-diphenylbutadiene, 1,6-Diphenylhexatriene, 2-Methylbenzoxazole, 2,5-Diphenyloxazole (PPO), 4-(dicyanomethylene)-2-methyl-6-(p-dimethylaminostyryl)-4H-pyran (DCM), 4-Dimethylamino-4'-nitrostilbene, 4',6-Diamidino-2-phenylindole (DAPI), 5-ROX, 7-AAD, 7-Benzylamino-4-nitrobenz-2-oxa-1,3-diazole, 7-Methoxycoumarin-4-acetic acid, 9,10-Bis (phenylethynyl) anthracene, 9,10-Diphenylanthracene, Acridine Orange, Acridine yellow, Adenine, Allophycocyanin (APC), AMCA, AmCyan, Anthracene, Anthraquinone, APC, Auramine O, Azobenzene, Benzene, Benzoquinone, Beta-carotene, Bilirubin, Biphenyl, BO-PRO-1, BOBO-1, BODIPY FL, Calcium Green-1, Cascade Blue™, Cascade Yellow™, Chlorophyll a, Chlorophyll b, Chromomycin, Coumarin, Coumarin 1, Coumarin 30, Coumarin 314, Coumarin 343, Coumarin 6, Cresyl violet perchlorate, Cryptocyanine, Crystal violet, Cy2, Cy3, Cy3.5, Cy5, Cy5.5, Cy7, Cytosine, DA, Dansyl glycine, DAPI, DiI, DiO, DiOCn, Diprotonated-tetraphenylporphyrin, DsRed, EDANS, Eosin, Erythrosin, Ethidium Monoazide, Ethyl p-dimethylaminobenzoate, FAM, Ferrocene, FI, Fluo-3, Fluo-4, Fluorescein, Fluorescein isothiocyanate (FITC), Fura-2, Guanine, HcRed, Hematin, Histidine, Hoechst, Hoechst 33258, Hoechst 33342, IAEDANS, Indo-1, Indocarbocyanine (C3) dye, Indodicarbocyanine (C5) dye, Indotricarbocyanine (C7) dye, LC Red 640, LC Red 705, Lucifer yellow, LysoSensor Yellow/Blue, Magnesium octaethylporphyrin, Magnesium octaethylporphyrin (MgOEP), Magnesium phthalocyanine (MgPc), Magnesium tetramesitylporphyrin (MgTMP), Magnesium tetraphenylporphyrin (MgTPP), Malachite green, Marina Blue®, Merocyanine 540, Methyl-coumarin, MitoTracker Red, N,N'-Difluoroboryl-1,9-dimethyl-5-(4-iodophenyl)-dipyrrin, N,N'-Difluoroboryl-1,9-dimethyl-5-[(4-(2-trimethylsilylethynyl), N,N'-Difluoroboryl-1,9-dimethyl-5-phenydipyrrin, Naphthalene, Nile Blue, Nile Red, Octaethylporphyrin, Oregon green, Oxacarbocyanine (C3) dye, Oxadicarbocyanine (C5) dye, Oxatricarbocyanine (C7) dye, Oxazine 1, Oxazine 170, p-Quaterphenyl, p-Terphenyl, Pacific Blue®, Peridinin chlorophyll protein complex (PerCP), Perylene, Phenol, Phenylalanine, Phthalocyanine (Pc), Pinacyanol iodide, Piroxicam, POPOP, Porphin, Proflavin, Propidium iodide, Pyrene, Pyronin Y, Pyrrole, Quinine sulfate, R-Phycoerythrin (PE), Rhodamine, Rhodamine 123, Rhodamine 6G, Riboflavin, Rose bengal, SNARF®, Squarylium dye III, Stains-all, Stilbene, Sulforhodamine 101, SYTOX Blue, TAMRA, Tetra-t-butylazaporphine, Tetra-t-butylnaphthalocyanine, Tetrakis(2,6-dichlorophenyl) porphyrin, Tetrakis(o-aminophenyl) porphyrin, Tetramesitylporphyrin (TMP), tetramethylrhodamine, Tetraphenylporphyrin (TPP), Texas Red® (TR), Thiacarbocyanine (C3) dye, Thiadicarbocyanine (C5) dye, Thiatricarbocyanine (C7) dye, Thiazole Orange, Thymine, TO-PRO®-3, Toluene, TOTO-3, TR, Tris(2,2'-bipyridyl) ruthenium (II), TRITC, TRP, Tryptophan, Tyrosine, Uracil, Vitamin B12, YO-PRO-1, YOYO-1, Zinc octaethylporphyrin (ZnOEP), Zinc phthalocyanine (ZnPc), Zinc tetramesitylporphyrin (ZnTMP), Zinc tetramesitylporphyrin radical cation, and Zinc tetraphenylporphyrin (ZnTPP). Suitable optical dyes are described in the 1996 Molecular Probes Handbook by Richard P. Haugland, hereby expressly incorporated by reference.

In some embodiments, one of the fluorescent dyes may be an Alexa Fluor® dye, including Alexa Fluor®, Alexa Fluor® 405, Alexa Fluor Alexa Fluor® 430, Alexa Fluor Alexa Fluor® 488, Alexa Fluor®500, Alexa Fluor®514, Alexa Fluor®532, Alexa Fluor®546, Alexa Fluor®555, Alexa Fluor®568, Alexa Fluor®594, Alexa Fluor®610, Alexa Fluor®633, Alexa Fluor® 647, Alexa Fluor®660, Alexa Fluor®680, Alexa Fluor®700, and Alexa Fluor®750 (Life Technologies Corporation Carlsbad, California).

One of the fluorescent dye may be a tandem fluorophore conjugate, including Cy5-PE, Cy5.5-PE, Cy7-PE, Cy5.5-APC, Cy7-APC, Cy5.5-PerCP, Alexa Fluor®610-PE, Alexa Fluor® 700-APC, and Texas Red-PE. Tandem conjugates are less stable than monomeric fluorophores, so comparing a detection reagent labeled with a tandem conjugate to reference solutions may yield MESF calibration constants with less precision than if a monomeric fluorophore had been used.

The flurophores may be a fluorescent protein such as green fluorescent protein (GFP; Chalfie, et al., *Science* 263 (5148): 802-805 (Feb. 11, 1994); and EGFP; Clontech—Genbank Accession Number U55762), blue fluorescent protein (BFP; Quantum Biotechnologies, Inc. Montreal Canada; Stauber, R. H. *Biotechniques* 24 (3): 462-471 (1998); Heim, R. and Tsien, R. Y. *Curr. Biol.* 6:178-182 (1996)), cyan fluorescent protein (CFP), and enhanced yellow fluorescent protein (EYFP; Clontech Laboratories, Inc., Palo Alto, California). In some embodiments, the fluorescent dye is dTomato, FLASH, mBanana, mCherry, mHoneydew, mOrange, mPlum, mStrawberry, mTangerine, ReAsH, Sapphire, mKO, mCitrine, Cerulean, Ypet, tdTomato, Emerald, or T-Sapphire (Shaner et al., *Nature Methods*, 2 (12): 905-9. (2005)).

The flurophores may be a fluorescent dye in the form of a fluorescent semiconductor nanocrystal particle, or quantum dot, including Qdot®525 nanocrystals, Qdot®565 nanocrystals, Qdot®585 nanocrystals, Qdot®605 nanocrystals, Qdot®655 nanocrystals, Qdot®705 nanocrystals, Qdot®800 nanocrystals (Life Technologies Corporation, Carlsbad, California). In some embodiments, the fluorescent dye may be an upconversion nanocrystal, as described in Wang et al., *Chem. Soc. Rev.*, 38:976-989 (2009).

The fluorescent molecules (fluorophores) may be conjugated with antibodies or other detection reagents, and associated with components of a sample that is analyzed by the instrument. Fluorophores can be activated by light from the instrument and re-emit light of a different wavelength. Since antibodies bind to antigens on the cells, the amount of light detected from the fluorophores is related to the number of antigens associated with the cell passing through the beam. In another embodiment of the invention, a fluorescently-labeled DNA oligonucleotide can be associated with the genomic DNA of a cell, and the amount of light detected from the fluorophores is related to the number of copies of the oligonucleotide that have hybridized to complimentary regions in the genome. Any specific set of fluorescently tagged detection reagents in any embodiment can depend on the types of experimental samples to be studied. See United States Patent Application Document No. 20130109050. As further explained in United States Patent Application Document No. 20130109050, "[s]everal fluorescent detection reagents can be used simultaneously, so measurements made as one cell passes through the laser beam consist of scattered light intensities as well as light intensities from each of the fluorophores. Thus, the characterization of a single cell can consist of a set of measured light intensities that may be represented as a coordinate position in a multidimensional space. Considering only the light from the fluorophores, there is one coordinate axis corresponding to each of the fluorescently tagged detection reagents. The number of coordinate axes (the dimension of the space) is the number of fluorophores used. Modern flow cytometers can measure several colors associated with different fluorophores and thousands of cells per second. Thus, the data from one subject can be described by a collection of measurements related to the number of antigens for each of (typically) many thousands of individual cells. See U.S. Pat. Nos. 7,381,535 and 7,393,656 for examples of flow cytometry methods and applications, which are hereby incorporated by reference in their entirety."

Those of ordinary skill in the art know how to select a second fluorophore that has a wavelength (color) which is different from that of the first fluorophore as required in various embodiments of the methods described and claimed herein.

The Rho family of GTPases belongs to the Ras superfamily of low molecular weight (~21 kDa) guanine nucleotide binding proteins. The most extensively studied members are RhoA, Rac1, and Cdc42. Small GTPases are a family of hydrolase enzymes that can bind and hydrolyze guanosine triphosphate (GTP). Small GTPases are a type of G-protein found in the cytosol; a small GTPase can function independently as a hydrolase enzyme to bind to and hydrolyze a guanosine triphosphate (GTP) to form guanosine diphosphate (GDP).

The Rho-family of p21 small GTPases are directly linked to the regulation of actin-based motile machinery and play a key role in the control of cell migration. Aside from the original and most well-characterized canonical Rho GTPases RhoA, Rac1, and Cdc42, numerous isoforms of these key proteins have been identified and shown to have specific roles in regulating various cellular motility processes.

A typical G-protein is active when bound to GTP and inactive when bound to GDP (i.e. when the GTP is hydrolyzed to GDP). The GDP can be then replaced by free GTP. Therefore, a G-protein can be switched on and off. GTP hydrolysis is accelerated by GTPase activating proteins (GAPs), while GTP exchange is catalyzed by Guanine nucleotide exchange factors (GEFs). Activation of a GEF typically activates its cognate G-protein, while activation of a GAP results in inactivation of the cognate G-protein.

Guanosine nucleotide dissociation inhibitors (GDI) maintain small GTP-ases in the inactive state.

The GTPase RhoA effectors include: Cit, Cnksr1, Diaph1, Diaph2, DgkQ, FlnA, KcnA2, Ktn1, Rtkn1, Rtkn2, Rhpn1, Rhpn2, Itprl1, PlcG1, PI-5-p5K, Pld1, Pkn1, Pkn2, Rock1, Rock2, PrkcA and Ppp1r12A.

The GTPase Rac1 effectors include Sra1, IRSp53, PAK1, PAK2 and PAK3.

The GTPase Cdc42 effectors include Wiskott-Aldrich syndrome protein, N-WASP, IRSp53, Dia2, Dia3, ROCK1 and ROCK2.

In a preferred embodiment, effector proteins are selected from the group consisting of PAK-1 RBD (a Rac1 and Cdc42 effector), Raf-1 RBD, (a Ras effector), Rhotekin-RBD (a Rho effector), RalGDS-RBD (a RAP1 effector protein) and RILP-RBD (a Rab-7 effector protein).

The present invention therefore provides rapid, effector-based, flow-cytometry assays to quickly assess sepsis-related GTPase activation status and monitor multiple GTPases in a single sample. In particular, the present invention relates to a novel flow cytometry-compatible, bead-based effector-binding assay for rapidly monitoring the activation status of multiple Ras superfamily GTPases in cell lysates. We have demonstrated proof-of-principle through the use of known agonists and antagonists of individual GTPases.

Additionally, we have applied the assay to acquire new information about the temporal activation of multiple GTPase cascades following SNV exposure and internalization that offer previously unprecedented mechanistic detail about SNV induced activation of cellular signaling. The data show that the interaction of hantaviruses with cognate, cell surface localized receptors responsible for entry results in the activation of signaling cascades that converge in the sequential activation of multiple small GTPases in the Ras, Rho and Rab families. In this way the GTPases act as signaling hubs[29] that further propagate the signals first induced by SNV cell surface receptor binding to promote the requisite changes in cell-cell adhesion, integrin activation and endocytosis that are necessary for virus infection and replication.

The invention is illustrated further in the following non-limiting examples.

Example 1

Effector Flow Cytometry Bead (EFCB) Assay

A novel flow based assay was platformed by monitoring GTPase activation in two different cell types (Vero E6 cells as well as HeLa cells used for-Rab7 experiments), suggesting that the assay is readily generalizable to different cell types. By coating beads with different effectors and multiplex analysis of fluorescent bead sets bearing different effectors[30] the assay can be extended to the simultaneous and high throughput analysis of multiple GTPases from the same cell lysate sample. We therefore anticipate that this approach will enable investigations into the interconnection of signaling networks with GTPase activation in normal cellular functions as compared to viral or bacterial infections or other pathogenic processes.

For productive infection of host cells, viruses typically activate multiple cellular GTPases to promote the cytoskeletal remodeling required for breaching inter- and intracellular cellular barriers to infection as well as intracellular trafficking of internalized virions to allow replication. We are particularly interested in Hantaviruses that cause hemorrhagic fever with renal syndrome (HFRS) and hantavirus cardiopulmonary syndrome (HCPS).[14] While the mechanism of hantavirus entry into host cells and the subsequent pathogenesis are poorly understood, avbs integrin and attachment factor, decay-accelerating factor (DAF/CD55) are known mediators of cell entry. DAF is a glycosylphosphatidylinostol (GPI)-anchored surface protein that protects cells from lysis by autologous complement and is highly expressed in many cells types.[5] When localized in lipid rafts,[6] DAF can form complexes with Src family tyrosine kinases[7-10] that signal upstream of the Ras superfamily of small GTPases which regulate many cell functions, such as cell proliferation, cytoskeletal alterations, trafficking, differentiation, survival, and migration. The ability to form close association with these signaling proteins capable of altering cell barrier function has made DAF an important receptor for pathogens. Thus DAF ligation on the cell surface might induce a signaling cascade involving a coordinate network of small GTPases.[11] [12] Parallel measurements of active GTPases downstream of receptor engagement will therefore be important for understanding how these signals are regulated and when and how their consolidation is related to both physiological and pathological contexts.

As described herein, we have provided a new flow cytometry approach for quantitatively measuring the activation status of Ras superfamily GTPases in activated cells based on specific effector binding. The advantages of the effector flow cytometry bead (EFCB) assay over conventional western blot and ELISA based methods (commercially available through Cytoskeleton, Inc.) are: 1) EFCB enables rapid measurement and analysis with results within 4 h, compared to days; 2) it offers quantitation and increased sensitivity measuring activated GTPases in cell lysates from <250,000 cells grown in a 48 well plate, well below the requisite minimum of $2 \times 10^6$ cells for ELISA, and 3) it can measure multiple GTPases from a single lysate either sequentially or using multiplex approach with differentially labeled beads, which can not be achieved with conventional assays that require the entire lysate for measurement of a single GTPase assay. For EFCB we functionalized glutathione beads with GST tagged Ras binding domains (RBD) of the effectors for Rac1 & Cdc42, H-Ras & R-Ras, Rap1, RhoA and Rab7: namely, PAK1, Raf1, Ral, RhoTekin, and RILP respectively. In this way unique effector-bearing beads were used as bait to extract active GTPases required for cytoskeletal remodelling (Rac1 and RhoA), regulation of adhesion (Rap1 and Ras) and trafficking (Rab1) from the same cell-lysate sample. The bead-bound effector-GTPase complexes were then incubated with fluorescently labeled antibodies directed against each activated GTPase and analyzed on a flow cytometer.

Exposing Vero E6 cells to known titers of UV killed and fluorescently labeled Sin Nombre hantavirus particles caused cells to first form filopodia and lamellipodia then contract and lose adhesion (FIG. 1a-d.).[13] These morphological changes are associated with Cdc42 (filopodia) Rac1 (lamellipodia), and RhoA activity manifested as stress fiber formation and cellular contraction. Using Pak1 and Rhotekin beads were used to record ≥2-fold increases in active Rac 1 and RhoA above resting levels in virus treated cells at 3 min and then returned to basal levels at twenty minutes. Similar measurements were recapitulated in cell lysates treated with known activation and inhibition standards of the GTPases. For brevity and clarity we will focus RhoA treatment. Calpeptin and EGF where used to activate RhoA while RhoGAP was used to hydrolyze active RhoA. In addition, owing to the known mutual antagonism between RhoA and Rac1, NSC23766 a specific inhibitor of the Rac1

GEF, Tiam1, was used to assess the effect of Rac1 suppression on the expression of active RhoA in EGF activated cells. Using the EFCB assay, a >2fold increase in active RhoA was measured in calpeptin treated cells. Active RhoA was hydrolyzed to baseline levels with RhoGAP. In EGF treated cells, NSC23766 suppressed active Rac1 to a degree below the GTPase's basal activity. From the same lysates, parallel measurements of RhoA-GTP showed a 2-fold increase above basal levels and 1.3 above EGF stimulation alone. The data are consistent with the mutual antagonism of Rac1 and RhoA wherein the inhibition of Rac1 is sensed and results in a higher RhoA activation.[14]

We also used a plate based GLISA assay to measure Rho family GTPase activation as a function of virus stimulation in normal cells and cells where surface-expressed DAF was first cleaved through PI-PLC treatment.[15] Virus exposure resulted in a significant time-dependent activation of RhoA and Rac1 GTPases peaking between 7 and 15 min after exposure (FIG. 4A). Rac1 GTPase activation was abolished in DAF-cleared cells demonstrating that the engagement of a GPI anchored receptor such as DAF was required upstream of Rac1. The overlapping temporal response in Rac1 and RhoA activation is consistent with cellular response elicited by Group B Coxsackieviruses, which are also ligands of DAF.[6] At longer times after virus exposure, the levels of active, GTP-bound Rac1 and RhoA fell below the baseline levels of active GTPases in uninfected controls. The diminution of GTPase activity, might be due to loss of cell adhesion, due to integrin anchorage regulatory role of Rac1-GTP.[16][17] Collectively, the controls and the GLISA assay data demonstrate applicability of our EFCB assay the measurement of active GTPases.

The loss of cell-cell adhesion in virus-activated cells led us to examine the relationship between loss of adhesion and changes in integrin affinity states across the ventral surface of virus activated cells. With this in mind we used our EFCB assay to examine the activity of Rap1 and H-Ras, which are known to play antagonistic roles in integrin affinity regulation.[18-22] Glutathione beads functionalized with effectors for Rap1 (GST Ral-GDS) and and H-Ras (Raf-1 RBD) were used to simultaneously assay activated Rap1, and H-Ras GTPases from virus activated cell lysates. Concurrently, we used FTI277 a specific inhibitor of H-Ras and 8-Cpt-2m-cAMP, and activator of Rap1 as a validation controls, which also exhibit antagonism between H-Ras and Rap1 with Rap1 interfering with the Raf effector function of H-Ras.[23] Thus inhibition of H-Ras induced a near 2-fold increase active Rap1, while activation of Rap1 decreased basal levels of H-Ras. Consistent with these observations, the activity of Rap1 and H-Ras in virus-activated cell lysates at 3 min and 20 min post-exposure showed that the pair was activated sequentially, where active Rap 1 peaked within the first 3 min and subsequently deactivated at 20 mins while H-Ras remained low while Rap1 was at its zenith, eventually peaking at 20 min as Rap1 was in decline. The staggered activity of Rap1 and H-Ras appears to follow the morphological trend established for the RhoGTPase assay in FIG. 1, where the loss of cell adhesion observed towards the end of the measurement is consistant with H-Ras upregulation, which is upstream of the down regulation of integrin affinity.

Figure 3:
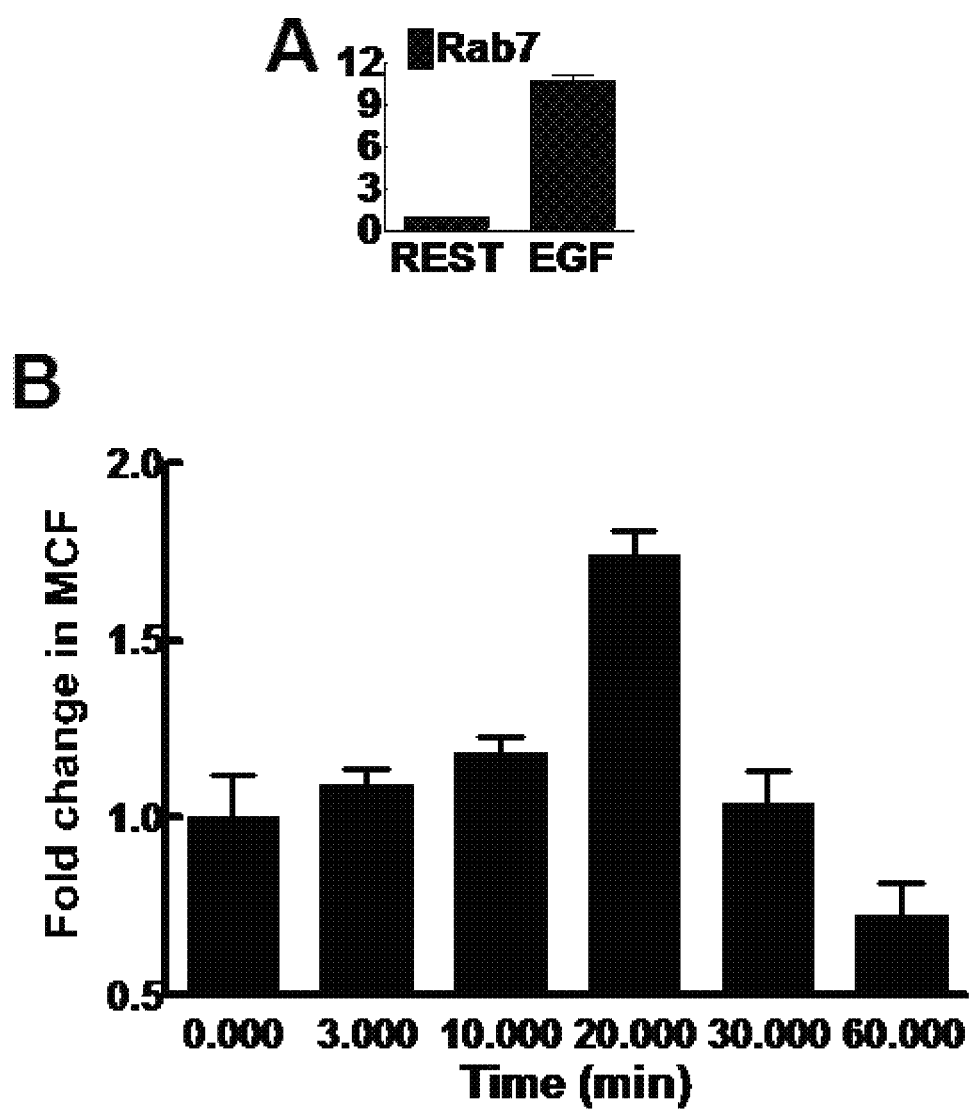
FIG. 3 shows that Rab7 mediate trafficking of SNV$^{R18}$ from early to late endosomes in Vero E6 cells. 3A shows that EGF was used to demonstrate the tractability of monitoring cellular Rab7 activation using beads functionalized with RILP-RBD. 3B shows that the highest Rab7-GTP levels were realized at 20 min after virus exposure.
Figure 5:
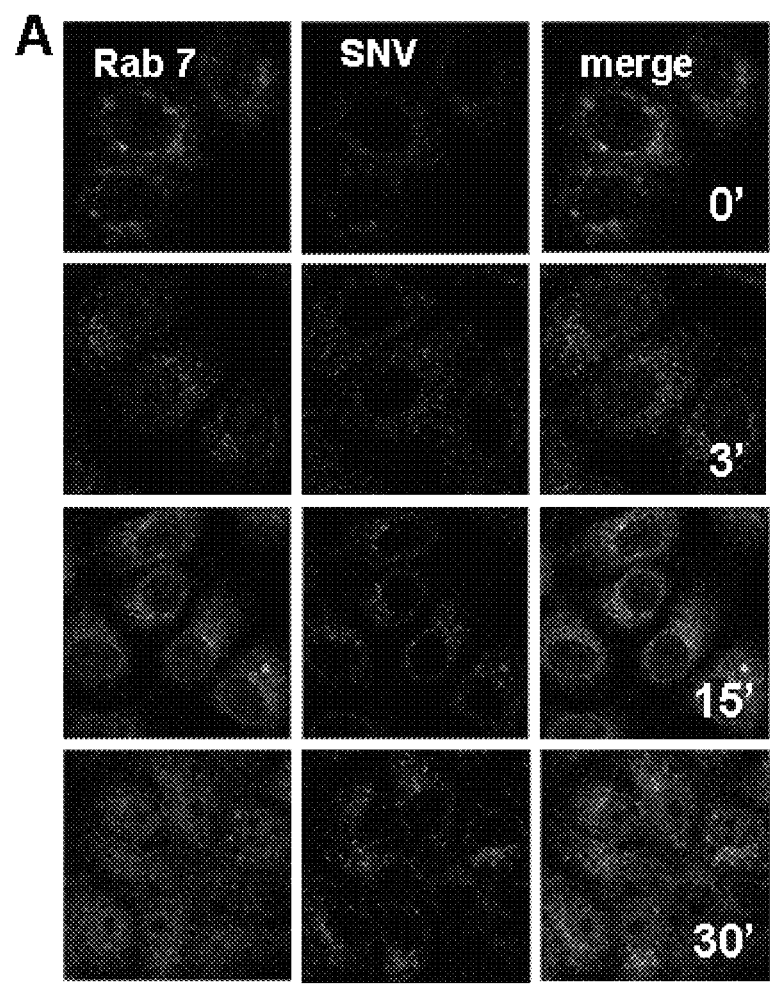
Figure 5:
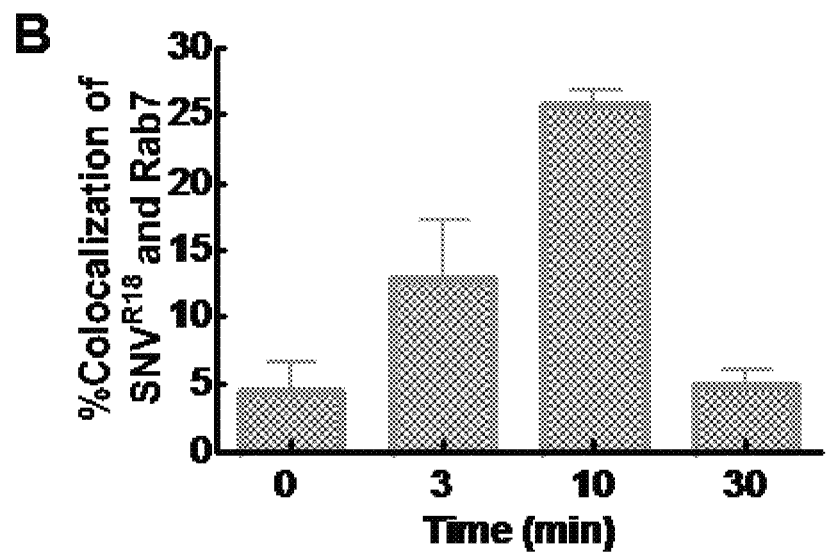
Figure 6:
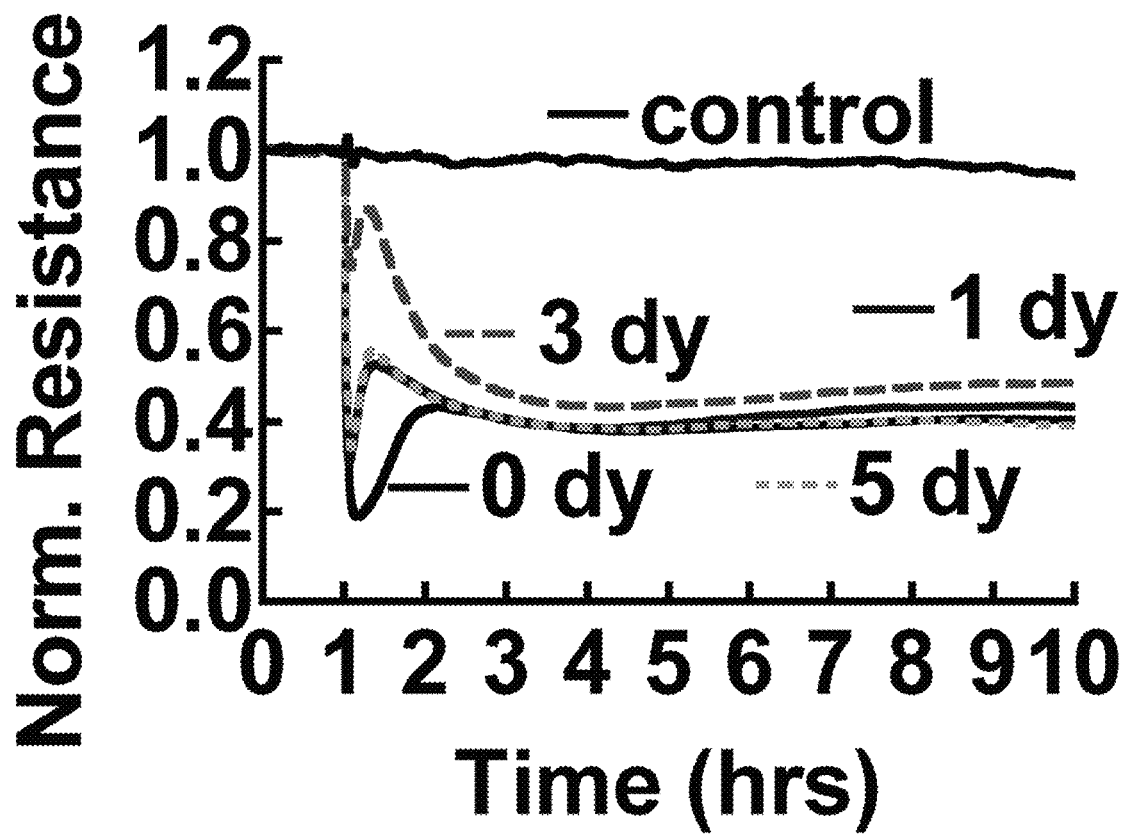
Figure 7:
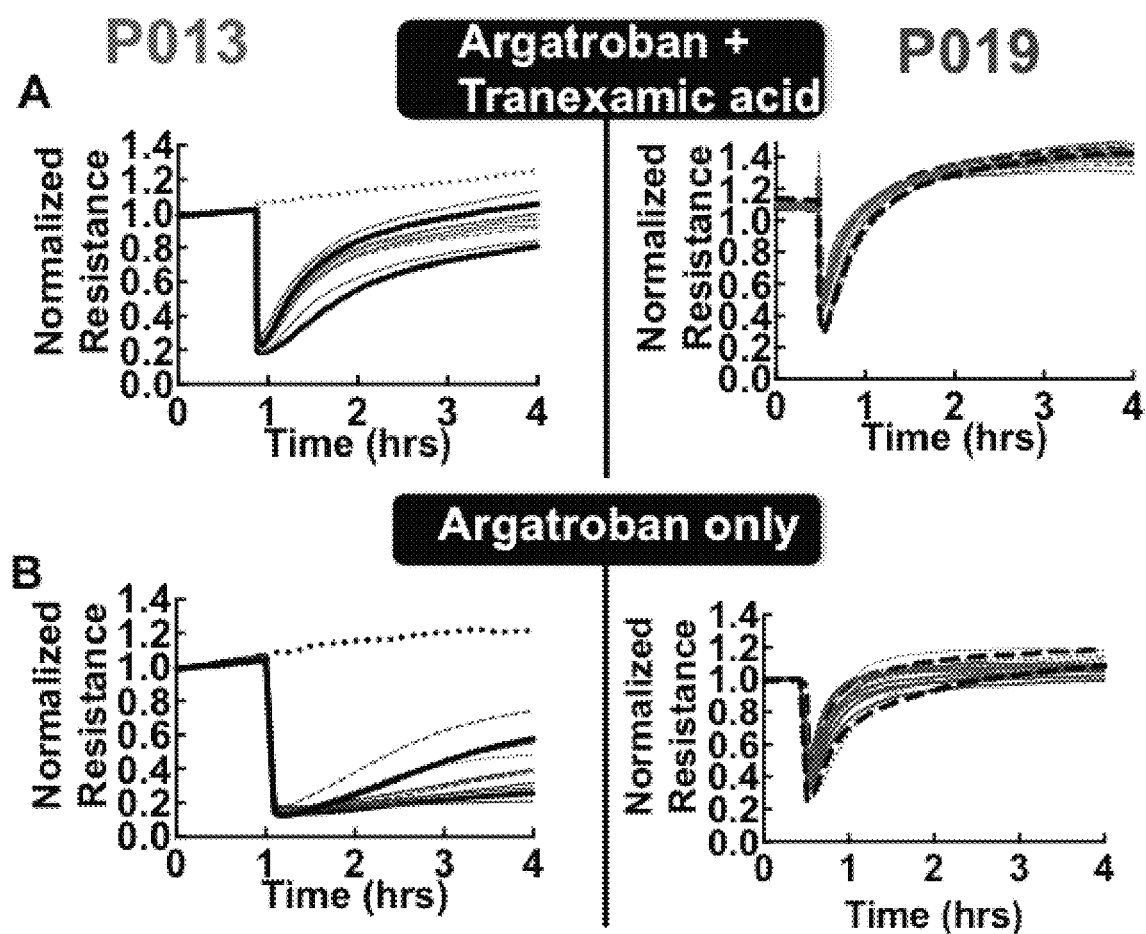

We next tested the applicability of the EFCB assay to monitor the intracellular trafficking of viruses by examining the activation of Rab7 in cells exposed to SNV. Rab7 and its downstream effector, Rab7 interacting lysosomal protein (RILP) are involved in the regulation of endocytic transport at several stages, post-internalization.[24,25] First, EGF was used to demonstrate the tractability of monitoring cellular Rab7 activation using beads functionalized with RILP-RBD (FIG. 3a). Within 15 min following EGF stimulation in HeLa cells, Rab7 activity was nearly 10 fold higher than in resting cells, consistent with the time course required for EGF-EGFR complex to reach late endosomes.[26] Next the Rab7-GTP levels were assessed in Vero E6 cell lysates following exposure to virus particles for various time intervals between 0 and 60 min. The highest Rab7-GTP levels were realized at 20 min after virus exposure (FIG. 3b). The timing of Rab7 activity is consistent with the endocytic delivery of large viral cargo to Rab7-positive late endosomes, which occurs in the 10-20 min time frame.[27,28] Immunofluorescence images of Rab7-positive endosomes after the synchronized entry of fluorescently labeled SNV (FIG. 5), shows that endosomes are redistributed from perinuclear space to the cell periphery and colocalize with cargo in the same time range.

In sum, we have devised a novel flow cytometry-compatible, bead-based effector-binding assay for rapidly monitoring the activation status of multiple Ras superfamily GTPases in cell lysates. We have demonstrated proof-of-principle through the use of known agonists and antagonists of individual GTPases. Additionally, we have applied the assay to acquire new information about the temporal activation of multiple GTPase cascades following SNV exposure and internalization that offer previously unprecedented mechanistic detail about SNV induced activation of cellular signaling. The data show that the interaction of hantaviruses with cognate, cell surface localized receptors responsible for entry results in the activation of signaling cascades that converge in the sequential activation of multiple small GTPases in the Ras, Rho and Rab families. In this way the GTPases act as signaling hubs[29] that further propagate the signals first induced by SNV cell surface receptor binding to promote the requisite changes in cell-cell adhesion, integrin activation and endocytosis that are necessary for virus infection and replication.

Our novel flow based assay was platformed here by monitoring GTPase activation in two different cell types (Vero E6 cells as well as HeLa cells used for-Rab7 experiments), suggesting that the assay is readily generalizable to different cell types. By coating beads with different effectors and multiplex analysis of fluorescent bead sets bearing different effectors 30 the assay can be extended to the simultaneous and high throughput analysis of multiple GTPases from the same cell lysate sample. We therefore anticipate that this approach will enable investigations into the interconnection of signaling networks with GTPase activation in normal cellular functions as compared to viral or bacterial infections or other pathogenic processes.

Materials and Methods

Antibodies. Monoclonal rabbit anti-RAP1 was obtained from Santa Cruz Biotechnology, Inc (Santa Cruz, CA). Monoclonal mouse antibodies: anti-Rho (A,B,C) clone 55, anti-Rac1, anti-Rab7 including the secondary antibody goat anti-mouse IgG (H+L) conjugated to Alexa Fluor 488 were were obtained from Millipore (Temecula, CA). Monoclonal mouse Anti-RRAS antibody was obtained from Abcam (Cambridge, MA). AntiRab 7 antibody (Sigma) Activators and Inhibitors. Rap1 Activator 8-Cpt-2me-cAMP (50 µM) obtained from R & D Systems (Minneapolis, MN). Rac1 Inhibitor (100 µM NSC23766 from Calbiochem). FTI-277 trifluoroacetate salt (an inhibitor of Farnesyl Transferase of H-Ras and K-Ras; 50 nM), and Rap1 inhibitor GGTI 298 trifluoroacetate salt hydrate, was obtained from Sigma- Aldrich (St. Louis, MO). Calpeptin (0.3 µM Rho activator) was from Calbiochem, Inc. 20 µg RhoGAP from Cytskeleton and Recombinant EGF was from Invitrogen.

Buffers: RIPA buffer: 74 mM $CaCl_2$), 50 mM Tris-HCl pH 7.4, 1% NP-40, 0.5% deoxycholic acid, 0.1% SDS, 1 mM sodium orthovanadate, and protease inhibitors. HHB buffer: 7.98 g/L HEPES (Na salt), 6.43 g/L NaCl, 0.75 g/L KCl, 0.095 g/L MgCl and 1.802 g/L glucose. Cell Culture: HeLa and Vero E6 cells from ATCC are plated at $4 \times 10^5$ cells per T75 flask, then allowed to grow for ~48 hours to medium/low confluence in Dulbecco's Modified Eagle Medium (DMEM) supplemented with 10% FBS, pen/strep, and L-glutamine in a 37 degree C. incubator with 5% $CO_2$. Cells were serum-starved in DMEM overnight before the GST pull-down.

Production of Sin Nombre Virus. SNV was propagated and titered in Vero E6 cells under strict standard operating procedures using biosafety level 3 (BSL3) facilities and practices (CDC registration number C20041018-0267) as previously described [31]. For preparation of UV-inactivated SNV, we placed 100 µL of virus stock (typically $1.5-2 \times 10^6$ focus forming units/ml) in each well of a 96-well plate and subjected the virus to UV irradiation at 254 nm for various time intervals (~5 $mW/cm^2$) as described elsewhere [32]. We verified efficiency of virus inactivation by focus assay before removing from the BSL-3 facility.

Fluorescent Labeling of SNV. The envelope membrane of hantavirus particles was stained with the lipophilic lipid probe octadecylrhodamine (R18) and purified as previously described[32]. The typical yield of viral preparation was $1 \pm 0.5 \times 10^8$ particles/µl in 300 µl tagged with ~10,000 R18 probes/particle or 2.7 mole % R18 probes in the envelope membrane of each particle of 192 nm diameter average size. Samples were aliquoted and stored in 0.1% HSA HHB buffer, and used within two days of preparation and storage at 4° C. For long-term storage, small aliquots suitable for single use were stored at −80° C.

Effector Proteins. GST-effector chimeras used for the studies were as follows. PAK-1 PBD, a Rac1 effector and Raf-1 RBD, a RAS effector protein were obtained from Millipore (Temecula, CA). Rhotekin-RBD, a Rho effector protein was purchased from Cytoskeleton, Inc. (Denver, CO). Ral-GDS, a RAP1 effector protein was obtained from Thermo Scientific (Fair Lawn, NJ). RhoGEF was obtained from Santa Cruz Biotechnology, Inc. (Santa Cruz, CA).

Expression and purification of GST-RILP. Plasmid encoding GST-RILP was expressed in competent *E. coli* BL21 cells. Cultures were grown at 37° C. to an absorbance of 0.5 O.D. measured at 595 nm and protein expression induced by transfer to room temperature and addition of 0.2 mM isopropyl-beta-D-1-thiogalactopyranoside (IPTG) for 16-18 h to maximize yield of properly folded active fusion protein. Purification of GST-RILP were performed according to standard procedures as previously described.[33][34] The harvested bacterial cell pellet was resuspended in cold native binding buffer. Cells were lysed using lysozyme and microtip sonicator (Misonix Inc., Newtown, CT, U.S.A.). The cell lysates were mixed with 10% TritonX-100 and mix over end for 30 min at 4° C. Cells were then centrifuged at 8,000×g for 10 minutes to pellet the cellular debris. The supernatant was mixed with freshly prepared Glutathione Spharose 4B slurry and bound at 4° C. for 2 h using gentle agitation to keep the resin suspended in the lysate solution. Glutathione beads with bound protein was settled using low speed centrifugation (500×g) followed by multiple washes before eluting the glutathione sepharose bound GST-tagged protein with 10 mM Glutathione in 50 mM Tris-HCl elution buffer. Eluted protein was concentrated by passing through Millipore Amplicon Ultra Tubes (MWCO 30,000). The purified protein was quantified using the BCA protein estimation kit (Pierce), Single use aliquots stored at −80° C. were used in the experiments.

Assembly of GST Effector proteins on GSH beads and GST pull-down assay. 13 µm Superdex peptide beads were derivatized with glutathione (γ-glu-cys-gly or GSH) as previously described.[33] GST conjugates of various GTPase-effector proteins were bound to suspensions of GSH beads to in order to form molecular assemblies necessary for capturing GTP-bound GTPases from cell lysates. The characteristic kinetic and equilibrium binding constants of glutathione-S-transferase (GST) fused to Green fluorescent protein (GFP), were used to establish optimal stoichiometric mixtures of GSH beads and specific GST effector fusion proteins for desired site occupancies of the GST effector proteins used in the flow cytometry assays.[33] Briefly, the binding assay of GST GFP to GSH beads was used to establish the following parameters. The saturable site occupancy values were used to determine the concentration of bead-borne GSH, while the $K_d$~80 nM was used to establish the optimal concentration ($10 \times K_d$) of GST effector proteins required to saturate GSH sites on the beads. GSH beads were mixed with the desired effector protein, incubated with shaking for 2 h at 4° C., recollected by centrifugation, and resuspended in RIPA buffer to 10,000 beads/µL. Beads were prepared fresh for each experiment and kept on ice while cell lysates were prepared.

TABLE 1

SNV Assay Results

| GTPase | Effector | Activator; final concentration; time | Inhibitor; final concentration; time | SNV titer; time |
|---|---|---|---|---|
| RhoA | Rhotekin-RBD, | Calpeptin; 1 µM; 30 min | | 10,000/cell; 3, 10, 20, 30, 60 |
| Rac1 | PAK-1 RBD | EGF; 10 nM; 15 min | NSC23766, 100 µM, 30 min | |
| Rap1 | Ral-GDS | 8-Cpt-2me-cAMP; 50 µM; 30 min | GGTI 298 | |
| R-Ras | Raf-1 RBD | | | |
| H-Ras | Raf-1 RBD | | FTI-277; 100 nM; 30 min | |
| Rab-7 | RILP-RBD | EGF; 10 nM; 15 min | | |

Stimulation and cell lysis. Vero E6 or HeLa cells were plated in 48 well plates or T 75 flasks and incubated overnight at 37° C. with 5% $CO_2$ and 90% humidity. Cells were starved for overnight in serum free medium followed by stimulation with activator or inhibitor at concentrations and times shown in Table 1. Stimulation with virus was typically performed with titers 10,000 particles/cell co-administered with an inhibitor as necessary and incubated for times ranging from 3 to 60 min as necessary. After incubating cells with various inhibitors, activators, and/or $SNV^{R18}$ for desired times, cells were lysed with 300 µL ice-cold RIPA buffer. The flasks are scraped, and the lysate collected. For the purposes of standardization, a fraction of the supernatant was collected, quantified using BCA protein estimation kit (Pierce). Lysates were kept ice cold at all times to limit hydrolysis of active GTPases. In our hands Rap1 was especially susceptible to hydrolysis whereas most of the other GTPases were robust. Lysates were sonicated briefly, and then centrifuged at 14,000 rpm for 10 minutes to clear the lysate of any unlysed materials and DNA. 10,000 beads for each effector assay was used and added to a lysate. If probing for more than one protein, divide the lysate was devided into desired tubes and probe individually. The beads and lysate were allowed to incubate for 1 hour at 4° C. After incubation, the beads were pelleted in a cold centrifuge. The residual lysate was collected and re-assayed for a different GTPase using different effector beads. The lysates could be saved for further pull down reactions by flash freezing in liquid nitrogen, then storing at −20 degrees C. for no longer than a week. The bead pellets were resuspended in RIPA buffer and incubated with a primary monoclonal antibody for the target GTPase, with gentle shaking for 1 hour. The beads were than centrifuged and Pellet resuspended in HHB buffer with an Alexa 488 secondary antibody at a 1:200 dilution for 1 hour with shaking at 4 degrees. Finally the beads were centrifuged once and resuspended in 100 μL RIPA buffer for reading on the flow cytometer.

Confocal Microscopy. Confocal laser scanning microscopy was performed with Zeiss META or LSM 510 systems using 63× 1.4 oil immersion objectives as previously described[35]. For live cell imaging, Vero E6 cells were plated in 8-well Lab-Tek chambers (Nunc) and temperature was maintained at 30° C. with an objective heater (Bioscience Tools) in appropriate buffer containing the desired cations, $Ca^{2+}$ or $Mn^{2+}$, which respectively confer low and high affinity states of $a_\nu b_3$[35]. In situ addition of $SNV^{R18}$ was performed by micropipeting an aliquot (100 μL) of ≈1×10$^9$ virion particles per well containing ~1.5×10$^5$ cells (this is nominally the stoichiometric equivalent of a multiplicity of infection (m.o.i.) of 1 if the virions from our stocks had not been inactivated with UV light) in 200 μl in HBSS and mixing well by trituration with the pipet. Images were collected using 2× line averaging at 3-10 s intervals, depending on imaging time, where longer intervals were necessary to minimize photobleaching.

REFERENCES

1 Hjelle B, Anderson B, Torrez-Martinez N, Song W, Gannon W L, Yates T L. Prevalence and geographic genetic variation of hantaviruses of New World harvest mice (*Reithrodontomys*): identification of a divergent genotype from a Costa Rican *Reithrodontomys mexicanus*. *Virology*. 1995; 207:452-59.

2 Hjelle B, Chavez-Giles F, Torrez-Martinez N, et al. Genetic identification of a novel hantavirus of the harvest mouse *Reithrodontomys megalotis*. *J. Virol.* 1994; 68:6751-54.

3 Hjelle B, Jenison S A, Goade D E, Green W B, Feddersen R M, Scott A A. Hantaviruses: clinical, microbiologic, and epidemiologic aspects. *Crit Rev. Clin Lab Sci.* 1995; 32:469-508.

4 Jonsson C B, Schmaljohn C S. Replication of hantaviruses. *Curr. Top. Microbiol. Immunol.* 2001; 256:15-32.

5 Brodbeck W G, Kuttner-Kondo L, Mold C, Medof M E. Structure/function studies of human decay-accelerating factor. *Immunology*. 2000; 101:104-11.

6 Coyne C B, Bergelson J M. Virus-induced Abl and Fyn kinase signals permit coxsackievirus entry through epithelial tight junctions. *Cell*. 2006; 124:119-31.

7 Rougeaux C, Berger C N, Servin A L. hCEACAM1-4L downregulates hDAF-associated signalling after being recognized by the Dr adbesin of diffusely adhering *Escherichia coli*. *Cellular microbiology*. 2008; 10:632-54.

8 Shenoy-Scaria A M, Gauen L K, Kwong J, Shaw A S, Lublin D M. Palmitylation of an amino-terminal cysteine motif of protein tyrosine kinases p56lck and p59fyn mediates interaction with glycosyl-phosphatidylinositol-anchored proteins. *Molecular and cellular biology*. 1993; 13:6385-92.

9 Shenoy-Scaria A M, Kwong J, Fujita T, Olszowy M W, Shaw A S, Lublin D M. Signal transduction through decay-accelerating factor. Interaction of glycosyl-phosphatidylinositol anchor and protein tyrosine kinases p56lck and p59fyn 1. *J Immunol.* 1992; 149:3535-41.

10 Stefanova I, Horejsi V, Ansotegui I J, Knapp W, Stockinger H. GPI-anchored cell-surface molecules complexed to protein tyrosine kinases. *Science* (New York, N.Y. 1991; 254:1016-9.

11 Schlessinger J. Cell signaling by receptor tyrosine kinases. *Cell*. 2000; 103:211-25.

12 Bar-Sagi D, Hall A. Ras and Rho GTPases: a family reunion. *Cell*. 2000; 103:227-38.

13 Ridley A J, Hall A. The small GTP-binding protein rho regulates the assembly of focal adhesions and actin stress fibers in response to growth factors. *Cell*. 1992; 70:389-99.

14 Machacek M, Hodgson L, Welch C, et al. Coordination of Rho GTPase activities during cell protrusion. *Nature*. 2009; 461:99-103.

15 Krautkramer E, Zeier M. Hantavirus causing hemorrhagic fever with renal syndrome enters from the apical surface and requires decay-accelerating factor (DAF/CD55). *Journal of virology*. 2008; 82:4257-64.

16 del Pozo M A, Alderson N B, Kiosses W B, Chiang H H, Anderson R G, Schwartz M A. Integrins regulate Rac targeting by internalization of membrane domains. *Science* (New York, N.Y. 2004; 303:839-42.

17 Parsons J T, Horwitz A R, Schwartz M A. Cell adhesion: integrating cytoskeletal dynamics and cellular tension. *Nat Rev Mol Cell Biol*. 2010; 11:633-43.

18 Wittchen E S, van Buul J D, Burridge K, Worthylake R A. Trading spaces: Rap, Rac, and Rho as architects of transendothelial migration. *Current opinion in hematology*. 2005; 12:14-21.

19 Wittchen E S, Burridge K. Analysis of low molecular weight GTPase activity in endothelial cell cultures. *Methods in enzymology*. 2008; 443:285-98.

20 Lad Y, McHugh B, Hodkinson P S, et al. Phospholipase C epsilon suppresses integrin activation. *The Journal of biological chemistry*. 2006; 281:29501-12.

21 Kinbara K, Goldfinger L E, Hansen M, Chou F L, Ginsberg M H. Ras GTPases: integrins' friends or foes? *Nat Rev Mol Cell Biol*. 2003; 4:767-76.

22 Hughes P E, Oertli B, Hansen M, Chou F L, Willumsen B M, Ginsberg M H. Suppression of integrin activation by activated Ras or Raf does not correlate with bulk activation of ERK MAP kinase. *Molecular biology of the cell*. 2002; 13:2256-65.

23 Zwartkruis F J, Bos J L. Ras and Rap1: two highly related small GTPases with distinct function. *Experimental cell research*. 1999; 253:157-65.

24 Feng Y, Press B, Chen W, Zimmerman J, Wandinger-Ness A. Expression and properties of Rab7 in endosome function. *Methods in enzymology*. 2001; 329:175-87.

25 Feng Y, Press B, Wandinger-Ness A. Rab 7: an important regulator of late endocytic membrane traffic. *The Journal of cell biology*. 1995; 131:1435-52.

26 Agola J, Jim P, Ward H, Basuray S, Wandinger-Ness A. Rab GTPases as regulators of endocytosis, targets of disease and therapeutic opportunities. *Clinical genetics.* 2012.

27 Lozach P Y, Huotari J, Helenius A. Late-penetrating viruses. *Current opinion in virology;* 1:35-43.

28 Lozach P Y, Mancini R, Bitto D, et al. Entry of bunyaviruses into mammalian cells. *Cell host & microbe;* 7:488-99.

29 Mitin N, Rossman K L, Der C J. Signaling interplay in Ras superfamily function. *Curr Biol.* 2005; 15: R563-74.

30 Surviladze Z, Young S M, Sklar L A. High-throughput flow cytometry bead-based multiplex assay for identification of Rho GTPase inhibitors. *Methods in molecular biology* (Clifton, N.J. 2012; 827:253-70.

31 Bharadwaj M, Lyons C R, Wortman I A, Hjelle B. Intramuscular inoculation of Sin Nombre hantavirus cDNAs induces cellular and humoral immune responses in BALB/c mice. *Vaccine.* 1999; 17:2836-43.
32 Buranda T, Wu Y, Perez D, et al. Recognition of DAF and avb3 by inactivated Hantaviruses, towards the development of HTS flow cytometry assays. *Anal. Biochem.* 2010; 402:151-60.
33 Tessema M, Simons P C, Cimino D F, et al. Glutathione-S-transferase-green fluorescent protein fusion protein reveals slow dissociation from high site density beads and measures free GSH. *Cytometry A.* 2006; 69:326-34.
34 Schwartz S L, Tessema M, Buranda T, et al. Flow cytometry for real-time measurement of guanine nucleotide binding and exchange by Ras-like GTPases. *Analytical biochemistry.* 2008; 381:258-66.
35 Chigaev A, Buranda T, Dwyer D C, Prossnitz E R, Sklar L A. FRET detection of cellular alpha 4-integrin conformational activation. *Biophysical Journal.* 2003; 85:3951-62.
36 Sandvig K, Olsnes S, Petersen O W, van Deurs B. Inhibition of endocytosis from coated pits by acidification of the cytosol. *Journal of cellular biochemistry.* 1988; 36:73-81.
37 Sandvig K, Olsnes S, Petersen O W, van Deurs B. Acidification of the cytosol inhibits endocytosis from coated pits. *The Journal of cell biology.* 1987; 105:679-89.
38 Somsel Rodman J, Wandinger-Ness A. Rab GTPases coordinate endocytosis. *Journal of cell science.* 2000; 113 Pt 2:183-92.
39 Rink J, Ghigo E, Kalaidzidis Y, Zerial M. Rab conversion as a mechanism of progression from early to late endosomes. *Cell.* 2005; 122:735-49.
40 Parton R G, Schrotz P, Bucci C, Gruenberg J. Plasticity of early endosomes. *Journal of cell science.* 1992; 103 (Pt 2): 335-48.
41 Vonderheit A, Helenius A. Rab7 associates with early endosomes to mediate sorting and transport of Semliki forest virus to late endosomes. *PLoS biology.* 2005; 3: e233.

Example 2

Flow Cytometry Assays for the Diagnosis of Sepsis.

Patient Cohort. The UNM Hospital (UNMH) is the only level 1 trauma center in the state of NM. According to the UNMH trauma registry the patients admitted between Jan. 1, 2008 and Dec. 31, 2012 comprised of 13,144 adults. Thus, an average of 500-600 trauma patients are admitted to our ICU annually, with an average of 200-250 complicated trauma patients defined as having a length of stay greater than 5 days with a high injury severity score (ISS)>20. Of the complicated trauma ICU patients, ~100-125 patients per year had sepsis spanning the range: sepsis (Systemic Inflammatory Response (SIRS) with infection), severe sepsis (organ dysfunction, or septic shock (severe sepsis with hypotension). The nature of injuries and associated infection are listed in Table 2 below.

TABLE 2

Association of pathogen with traumatic site of injury and time from presentation

| Site of injury | Pathogen | $t_{dx}$ |
|---|---|---|
| Soft tissue: stab, gunshot, open fractures etc. | Staphylococcal and Streptococcal infection including MRSA | first 5-7 days |
| | Gram-neg. (Enterobacter, E. coli, Pseudomonas, Acinetobacter) | >7 days |
| later infection on same wound | | |
| Deep muscle injury wounds | anaerobes including Bacteroides, Clostridium, and Peptostreptococcus | >5 days |
| Lung based infections. Early: | gram-pos. organisms (Strep, Staph, H. flu) | <5 days |
| Late: | gram-neg. including Pseudomonas, Acintobacter, and Serratia | >5 days |
| Intraabdominal infection (abscess and peritonitis) | gram neg. rod (E. coli, Enterobacter), gram positivie (Enterococcus), gram positive rods (Clostridium, Bacteroides). | >5 days |

With IRB approval, patients were enrolled with the goal of collecting daily blood samples from subjects admitted to UNMH intensive care unit (ICU) in order to investigate host responses to trauma and sepsis. The de-identified patient records contain clinical, and demographic data (gender and ethnicity etc.) Multiple small volume aliquots of coded serial samples, collected for up to 14 days from enrollment. 25 are now stored in a −80° C. freezer, in the PI's lab. We have also enrolled 20 healthy controls with a target of 50 subjects for our study.

Inclusion criteria. Patients admitted under the Trauma Alert Protocol (TAP) to the Emergency Department (ED) at the University of New Mexico Hospital will be screened for inclusion in the study. The TAP system is activated in response to a specific constellation of traumatic injuries, which are known to predict the need for Trauma Surgical consultation. These include: a) High speed mechanism motor vehicle collisions/crashes. b) Falls from great heights. c) Penetrating trauma (stab wounds and gunshot wounds) to the proximal extremities, head, or torso. d) Significant crush injuries. e) Patients hit by motor vehicle. f) High speed bicycle and motorcycle crashes. g) Any other significant trauma as judged by ambulance report.

Initial inclusion criteria include age greater than 18, TAP status during trauma resuscitation, not pregnant, and not currently a prisoner. Patients meeting initial inclusion criteria will have a single blood sample drawn at the time of ED evaluation. They will then undergo screening for final inclusion in the study within 24 hours of arrival. Secondary, or final inclusion criteria include meeting all requirements of initial inclusion, being admitted to an intensive care unit (ICU), and possessing the ability to provide English or Spanish written informed consent either personally or via a surrogate decision maker as determined by the New Mexico Uniform Health Care Decisions Act (NMSA 1978 24-7A-5).

Thrombin and Plasmin Contribute to Loss of Cell Barrier Function in Cell Monolayers as Measured with Electric Cell-Substrate Impedance Sensing (ECIS).

We have recently used an electric cell-substrate impedance sensing (ECIS) based assay,[33A] to measure the differential contributions of thrombin and plasmin to the loss of cell barrier function in patients infected with Sin Nombre virus.[35A] For ECIS measurements, Vero E6 cells developed as a more robust surrogate for endothelial cells in primary screens were plated at confluence in electrode-containing dishes (Applied BioPhysics, Inc., Troy, NY) and then allowed to attach, spread, and organize for at least 24 hours. Cellular impedance was measured continuously at a single frequency of 4,000 Hz. Increase in resistance corresponds to increasing cell barrier function. When cellular impedance reached plateau values 3,000Ω-4,000Ω, 20 µl of plasma were added to 200 μl of media in the well. FIG. 6 shows that exposure of cells to trauma patient plasma caused cell monolayer resistance to drop rapidly and then partially recover to a lower plateau over the course of several hours. In contrast, plasma from healthy controls had no effect. The multiphasic changes in the time-course experiments are caused by several edemagenic factors such as thrombin, plasmin and other inflammatory mediators. Pretreatment of plasma samples with selective inhibitors of thrombin and plasmin can be used as a surrogate for assessing hemostasis balance in trauma patients (FIG. 7).

Plasmin Activity is Upregulated in Some Patients Who Develop Sepsis.

The edemagenic signaling of thrombin and plasmin is mediated by protease-activated receptors (PAR-1, PAR-3 and PAR-4)[27-31A] PAR receptor-signaling causes cytoskeletal remodeling characterized by the activation of the small GTPase, RhoA associated with stress fibers and loss of cell barrier function.[30, 40-45A] We tested the idea that host response to bacterial infection elicits an increase in thrombogenesis, (release of thrombin in circulation) which generates increased fibrinolysis (increase in plasmin in serial samples). We used the following subjects.

Subject P13: White female, 77, was admitted after a fall down stairs sustaining a head injury and rib fractures, intubated on arrival in the emergency department. Clinical Summary: day 2: respiratory distress, possible pneumonia; placed on ventilator; fever; sputum culture collected, and a broad-spectrum antibiotic treatment was initiated on day 4. day 6: MRSA infection confirmed; antibiotic treatment continued for 8 consecutive days. Day 8: Developed an unexplained leukocytosis to ~17000 WBC which resolved on its own. 13 days in ICU dis-enrolled from study after 10 days of sample collection due to family request.

Subject P19: Hispanic white male, 52, was admitted after shotgun wound to abdomen; low grade liver lacerations, high grade right renal injury; traumatic abdominal wall hernia ~3 cm, fracture to three ribs, 7 days in ICU, no frank sepsis during 14 day sample collection.

Serial samples of patients P13 and P19 were each treated with a mixture of thrombin and plasmin inhibitors, (argatroban[29A] and tranexamic acid[46A] respectively) and analyzed by ECIS (FIG. 7). Using the data points taken at 4 hours in the time-course assays (FIG. 7), we then calculated the ratio of the thrombin-inhibited samples and thrombin- and plasmin-inhibited assays (Arg/Arg+TA in FIG. 8) in order to determine the relative expression of thrombin and plasmin in the two patients.

For P19, argatroban alone produces nearly the same result as a mixture of argatroban and tranexamic acid, suggesting that the level of circulating Plasmin in P19 was negligible. For P13, the recovery of cell barrier function was better when the mixture of thrombin and plasmin inhibitors was used, compared to thrombin alone (P13 in FIG. 8). The downward slope of the ratiometric plot suggests that plasmin increased daily up to day 8 when the patient presented with leukocytosis.

GTPAse Activity Screen,

We have developed a multiplex Gtrap assay[36A] that allows us to measure the expression of multiple GTPases that are activated by exposure of cells to patient plasma. For proof of principle we found that P13 samples induced activation of RhoA and Rap 1 whereas P19 was relatively silent. FIG. 8B shows that the activity of RhoA measured in Vero E6 cells, after exposure to plasma (P13 and P19) collected on even days from day 0 to 8. For P13 RhoA activity peaks at day 4 and drops thereafter. We hypothesize that the increase in thrombin generation in P13 was in response to bacterial infection as the decrease of RhoA activity coincided with antibiotic treatment on day 4. The changes in Rap1 mirrored RhoA (not shown) However, treatment of samples with argatroban shows that RhoA GTP activation was primarily due to thrombin[27-31A] rather than direct bacterial activation.[14A, 20A]

Onset of Sepsis in Patients with Measurement of Cell Barrier Function In Vitro.

Rationale and Hypothesis. The clinical presentation of sepsis is often indistinguishable from systematic inflammatory response caused by sterile inflammation in trauma.[9A] This ambiguity may cause delays in the administration of lifesaving standard therapies of appropriate antibiotics and precludes misuse of antimicrobial agents.[9A] During infection, inflammatory mediators of bacteria and/or host can manipulate the procoagulant/anticoagulant equilibrium and cause sepsis as well as engaging the RhoGTPases that regulate the actin cytoskeleton. We have observed that the onset of infection can be manifested by an increase in plasmin as measured by changes in cell monolayer resistance FIG. 2A and increase in RhoA and Rap1 activity (FIG. 8).

Screening Serial Plasma Samples for Preseptic Changes of Cell Barrier Function.

Experimental Approach. A 96 well plate format ECIS (Applied Biophysics, Troy, NY) will be used to screen a collection of over 30-50 different serial plasma samples being collected from patients who go on to develop clinically documented cases of sepsis or sterile systematic inflammatory response (SIRS). For ECIS measurement, Vero E6 cells will be plated at confluence for at least 24 hours in electrode-containing dishes (Applied BioPhysics, Inc., Troy, NY). In our experience,[35A] Vero E6 epithelial cells derived from monkey kidney cells form more robust cell-cell barrier contacts (with typical resistance values in the 3,000-4,000 ohm range) compared to endothelial cells (1,000-1,500 ohms). Compared to endothelial cells,[35A] Vero cells are less sensitive to spurious environmental cues that disrupt cell barrier function. While previous studies have shown that thrombin differentially regulates human lung epithelial and endothelial cells[47A] our results herein suggest that the effects of thrombin on Vero E6 cells is similar to endothelial cells.[35A] They grow to confluence very rapidly compared to endothelial cells and very suitable for high throughput primary screens. Experiments will be performed in triplicate wells during the same run, at any given time. The readout for these experiments will be a measurement of changes in cell monolayer resistance after exposure to plasma samples treated with a mixture of argatroban and tranexamic acid and argatroban alone to block the activation of PAR receptors by thrombin and plasmin as described for FIG. 7. Changes in plasmin expression will be determined from a ratiometric plot a shown in FIG. 8A. Non-parametric Anova will be used to determine statistical significance.

Materials. De-identified samples from trauma patients (>25 current) and healthy control samples (>20); clinical data; ECIS cultureware, Argatroban (thrombin inhibitor) and tranexamic acid (plasmin inhibitor) from Santa Cruz Biotech. Amicon centrifugal filter units for sample fractionation will be purchased from Millipore.

Because many gram-positive and gram-negative bacterial species can increase the concentration of plasmin[14, 13.4, 22.4] in septic patients, we expect to experimentally determine the onset of sepsis with ECIS by a ratiometric plot in the ECIS endpoints of plasma samples treated with argatroban only and those treated with argatroban and tranexamic acid (FIG. 8C). However because not all bacteria are capable of inducing fibrinolysis we expect some negative results. These types of infection will be used as a stratification factor in our proteomic analysis described in Aim 2c. Other confounding factors[55.4] are discussed in Aim IC. Severe trauma injuries and subsequent medical intervention might obscure our ability to accurately measure subsequent changes to the hemostatic balance in such patients at the onset of bacterial infection.

Profile of Plasminogen Activation in Serial Samples from Septic Patients Correlates to ECIS Profiles.

Experimental Approach. It has been shown that plasminogen concentrations in septic patients are significantly decreased due to bacterial interactions that activate tissue plasminogen activator ((PA) or urokinase plasminogen activator (uPA).[21, 51] We will screen trauma patient and healthy controls for changes in active tPA, uPA and anti plasmin in serial samples of septic and aseptic patients, to test whether acute changes in the expression of these factors is associated with onset of sepsis.

Materials: We will purchase: Human plasminogen total antigen assay ELISA kit (HPLGKT-TOT), Active human tPA functional assay ELISA kit (HTPAKT), Active human uPA functional assay ELISA kit (HUPAKT) Human antiplasmin total antigen assay ELISA kit (HA2APKT-TOT), Human Thrombin Antithrombin Complex total antigen assay ELISA kit (HTATKT-COM), Active human PAI-1 functional assay ELISA kit (HPAIKT) from Molecular Innovations (Novi, MI).

We have previously used these kits to measure active and total levels of plasminogen activator inhibitor-1 (PAI-1) in hantavirus patient samples.[35.4] These kits are capable of detecting samples at 5 orders of magnitude below the normal concentration ranges found in healthy human samples. Thus we expect to accurately quantify the concentrations of our target analytes using appropriately diluted samples. The assay for total human plasminogen measures plasminogen, and its proteolytic products plasmin and plasmin antiplasmin complex. Thus this assay will be used to determine the concentration of plasminogen in each patient, in order to normalize the sensitivity of the ECIS measurements to putative plasmin activity in different patient samples. The assays that measure active tPA and uPA are based on formation of covalent complexes between active (PA or uPA and PAI-1 which is immobilized on the plate. Inactive or complexed proteases will not bind to the PAI-1 and will not be detected by the assay. This might confound data from patients expressing high levels of PAI-1. However such samples are expected to present very limited plasmin activity because of PAI-1.[52-54.4] If this where the case, this would likely be apparent in the clinical data, and confirmed by PAI-1 measurement with ELISA as well as mass spectrometry.[35.4]

GTPase Activation Correlates to Onset of Sepsis.

Experimental Approach. Bacteria overcome the host's defences, by hijacking RhoGTPases that regulate the actin cytoskeleton.[20] The bacteria produce various toxins and virulence factors that can activate or inactivate RhoGTPases by different mechanisms, that include: a) post-translational modification of the GTPases, b) by mimicking guanine nucleotide exchange factors (GEFs), GTPase activating proteins (GAPs) or guanine nucleotide dissociation inhibitor (GDIs) regulatory factors, c) modification of upstream regulators of small RhoGTPase.[20.4]

We have developed a rapid multiplex assay for detecting active GTPase targets in cells exposed to patient plasma (FIG. 8).[36.4] We are therefore uniquely positioned to screen multiple samples for evidence of GTPase activity that can be correlated to infection. The Gtrap assay can measure several activated GTPases in lysates, that attach to their cognate effector proteins immobilized on up to 12 red color and fluorescence intensity encoded beads (FIG. 9A). When two different sized beads are used, the assay can measure up to 24-targeted conditions simultaneously. The GST-effector chimeras consisting of the minimal GTPase binding domains (RBD) for the studies are: PAK-1 RBD, (a Rac1 and Cdc42 effector), Raf-1 RBD, (a Ras effector) Rhotekin-RBD, (a Rho effector) RalGDS-RBD, (a RAP1 effector protein).[36.4] 10,000 beads for each target effector are mixed and added to cell lysates, typically generated from small volume assays of 50,000 cells. The beads are incubated in cell lysates for an hr at 4° C., centrifuged and resuspended in 50 µl buffer (1:20 final antibody dilution).

Figure 9:
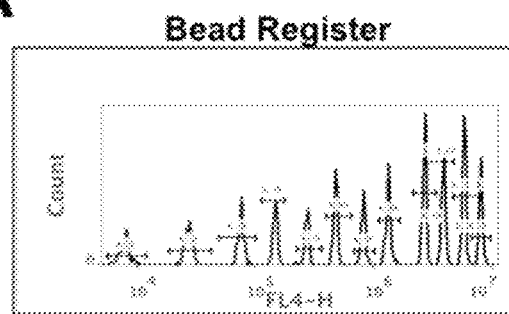
Figure 9:
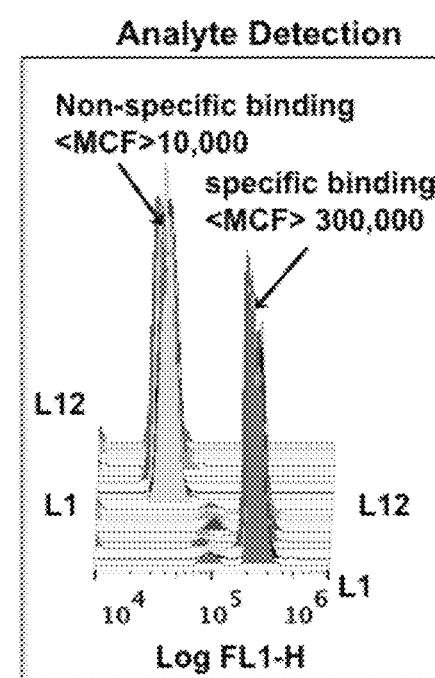

Monoclonal antibodies for each target GTPase are pooled and added to the multiplex bead suspension and incubated for an hour at 4° C. A secondary antibody tagged with Alexa®488 dye, is then used to fluorescently tag bead-associated antibodies. The samples are then analyzed on a flow cytometer where the red fluorescence on the effector bead is used to gate the green fluorescence associated with the target (FIG. 9). A typical assay regardless of the number of GTPase targets takes only 3 hrs. Therefore we are capable of analyzing many sample that are required for this project.

Figure 8:
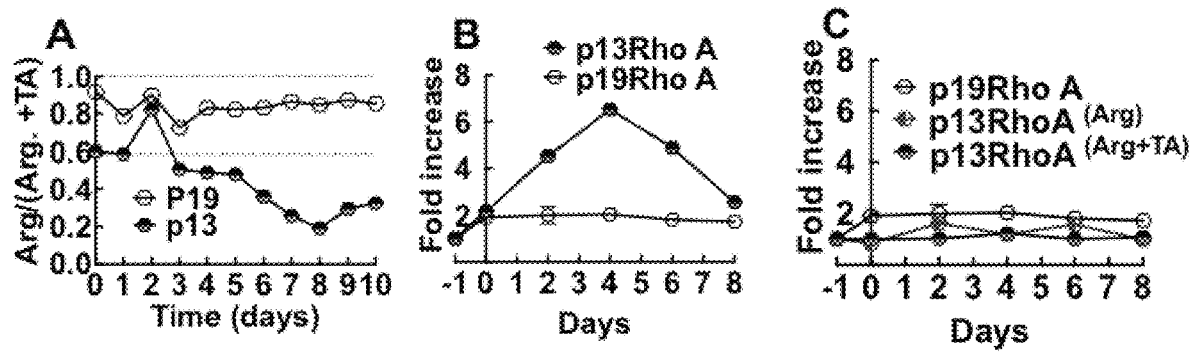
Figure 10:
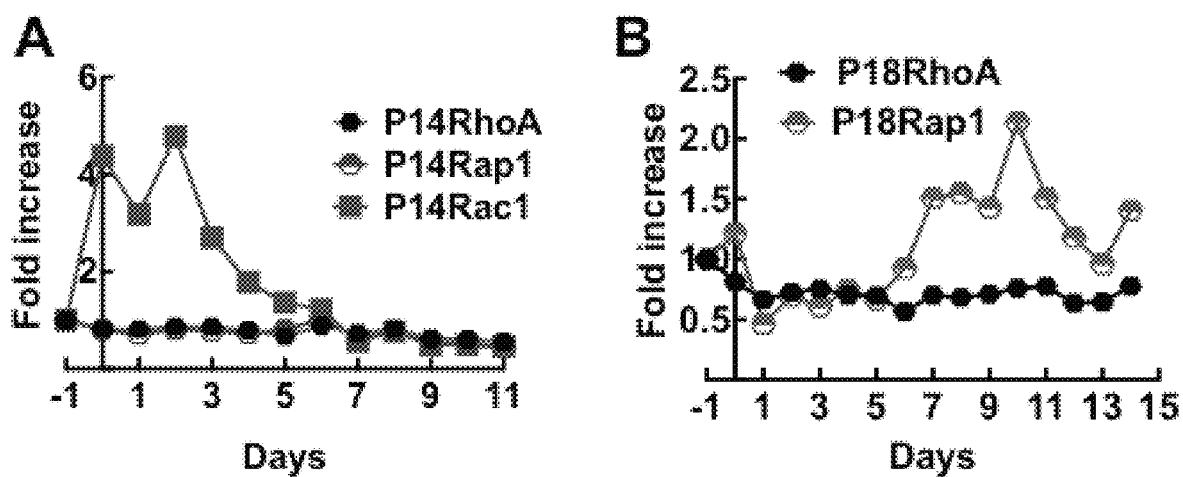

Pathogenic bacteria have evolved to allow the adaptive development of virulence factors that are optimal during different stages of infection. For example it is believed that during initiation of infection, bacterial adhesins favor tissue colonization, whereas at later stages, exotoxins promote bacterial spread and blockage of immune cell responses.[55.4] RhoGTPases are universal regulators of eukaryotic cell function and have been identified as primary targets of virulence factors from diverse bacterial species[14.4, 20.4] Rho GTP binding proteins regulate the actin cytoskeleton, but they also control cell cycle progression, transcriptional activity, intracellular vesicle transport and cell transformation.[56.4] By downregulating RhoGTPases, bacterial pathogens can block crucial immune cell functions such as chemotaxis, phagocytosis and antigen presentation.[14, 20] In our preliminary studies, we have sampled the GTPase activity induced by soluble factors in the plasma of 3 septic patients (FIGS. 8 and 10). The patients appear to present sepsis at different stages of admission, with P14 (Staph. pneumonia) presenting as preexisting, P13 (Staph. aureus (MRSA)) within 2 days of admission and p18 a week after admission. Significantly the upregulation of RhoGTPAses in each case appears to be correlated to the onset of sepsis. A potential pitfall in this approach is the ability to measure/infer GTPases deactivation by bacterial factors relative to normal quiescence. The down regulation of GTPase activity can be measured indirectly. For P18 who suffered severe injuries, it was surprising that RhoA activity was lower than normal controls (compared to P13). To test if soluble bacterial components in P18 plasma, inhibited RhoA activation (most likely by GTP hydrolysis initiated by activation of GAPs$^{57,4})^{14,4}$ day 10 samples from P18 were mixed with RhoA-activating P13 samples (examined in FIG. 8). P19 (FIG. 8) samples and argatroban were used as negative, and positive controls respectively. The results showed that mixing P18 sample with P13 sample inhibited RhoA activation.

REFERENCES

1A. McAdow, M. et al. Preventing *Staphylococcus aureus* Sepsis through the Inhibition of Its Agglutination in Blood. *PLoS pathogens* 7 (2011).

2A Sun, H. M. The interaction between pathogens and the host coagulation system. *Physiology* 21, 281-288 (2006).

3A. van der Poll, T. & Herwald, H. The coagulation system and its function in early immune defense. *Thrombosis and haemostasis* 112 (2014).

4A Wang, H. J. et al. Identification of four novel serum protein biomarkers in sepsis patients encoded by target genes of sepsis-related miRNAs. *Clin Sci* 126, 857-867 (2014).

5A. Sankar, V. & Webster, N. R. Clinical application of sepsis biomarkers. *J Anesth* 27, 269-283 (2013).

6A Pierrakos, C. & Vincent, J. L. Sepsis biomarkers: a review. *Critical care* 14 (2010).

7A. Faix, J. D. Established and novel biomarkers of sepsis. *Biomark Med* 5, 117-130 (2011).

8A Charles, P. E. & Gibot, S. Predicting outcome in patients with sepsis: new biomarkers for old expectations. *Critical care* 18 (2014).

9A Reinhart, K., Bauer, M., Riedemann, N. C. & Hartog, C. S. New Approaches to Sepsis: Molecular Diagnostics and Biomarkers. *Clin Microbiol Rev* 25, 609-634 (2012).

10A. Vitiello, M. et al. Pathophysiological changes of gram-negative bacterial infection can be reproduced by a synthetic peptide mimicking loop L7 sequence of *Haemophilus influenzae* porin. *Microbes and infection/Institut Pasteur* 10, 657-663 (2008), 11A. Lahteenmaki, K., Kuusela, P. & Korhonen, T. K. Bacterial plasminogen activators and receptors. *FEMS microbiology reviews* 25, 531-552 (2001).

12A. Bhattacharya, S., Ploplis, V. A. & Castellino, F. J. Bacterial plasminogen receptors utilize host plasminogen system for effective invasion and dissemination. *Journal of biomedicine & biotechnology* 2012, 482096 (2012).

13A. Rivera, J., Vannakambadi, G., Hook, M. & Speziale, P. Fibrinogen-binding proteins of Gram-positive bacteria. *Thrombosis and haemostasis* 98, 503-511 (2007).

14A. Aktories, K. & Barbieri, J. T. Bacterial cytotoxins: targeting eukaryotic switches. *Nature reviews. Microbiology* 3, 397-410 (2005).

15A. Aktories, K. & Just, I. Clostridial Rho-inhibiting protein toxins. *Current topics in microbiology and immunology* 291, 113-145 (2005).

16A. Aktories, K. & Schmidt, G. A new turn in Rho GTPase activation by *Escherichia coli* cytotoxic necrotizing factors. *Trends in microbiology* 11, 152-155 (2003).

17A. Bokoch, G. M. Regulation of innate immunity by Rho GTPases. *Trends Cell Biol* 15, 163-171 (2005).

18A. Boquet, P. & Lemichez, E. Bacterial virulence factors targeting Rho GTPases: parasitism or symbiosis? *Trends Cell Biol* 13, 238-246 (2003).

19A. Cherfils, J. & Zeghouf, M. Regulation of small GTPases by GEFs, GAPs, and GDIs. *Physiological reviews* 93, 269-309 (2013).

20.A. Lemichez, E. & Aktories, K. Hijacking of Rho GTPases during bacterial infection. *Experimental cell research* 319, 2329-2336 (2013).

21A. Tapper, H. & Herwald, H. Modulation of hemostatic mechanisms in bacterial infectious diseases. *Blood* 96, 2329-2337 (2000).

22A. Steams-Kurosawa, D. J., Osuchowski, M. F., Valentine, C., Kurosawa, S. & Remick, D. G. The Pathogenesis of Sepsis. *Annu Rev Pathol-Mech* 6, 19-48 (2011).

23A. Skibsted, S. et al. Biomarkers of endothelial cell activation in early sepsis. *Shock* 39, 427-432 (2013).

24A. Kim, W. S. & Lee, H. J. Management of sepsis. *J Korean Med Assoc* 56, 819-826 (2013).

25A. Hernandez, G., Bruhn, A. & Ince, C. Microcirculation in Sepsis: New Perspectives. *Current vascular pharmacology* 11, 161-169 (2013).

26A. Rittirsch, D., Flierl, M. A. & Ward, P. A. Harmful molecular mechanisms in sepsis. *Nat Rev Immunol* 8, 776-787 (2008).

27A. Levi, M., Keller, T. T., van Gorp, E. & ten Cate, H. Infection and inflammation and the coagulation system. *Cardiovascular research* 60, 26-39 (2003).

28A. Kumar, P. et al. Molecular mechanisms of endothelial hyperpermeability: implications in inflammation. *Expert Rev Mol Med* 11 (2009).

29A. Escolar, G., Bozzo, J. & Maragall, S. Argatroban: A direct thrombin inhibitor with reliable and predictable anticoagulant actions. *Drugs Today* 42, 223-236 (2006).

30A. Carbajal, J. M., Gratrix, M. L., Yu, C. H. & Schaeffer, R. C., Jr. ROCK mediates thrombin's endothelial barrier dysfunction. *American journal of physiology. Cell physiology* 279, C195-204 (2000).

31A. Anwar, K. N., Fazal, F., Malik, A. B. & Rahman, A. RhoA/Rho-associated kinase pathway selectively regulates thrombin-induced intercellular adhesion molecule-1 expression in endothelial cells via activation of I kappa B kinase beta and phosphorylation of RelA/p65. *J Immunol* 173, 6965-6972 (2004).

32A. Sosothikul, D., Seksam, P., Pongsewalak, S., Thisyakom, U. & Lusher, J. Activation of endothelial cells, coagulation and fibrinolysis in children with Dengue virus infection. *Thrombosis and haemostasis* 97, 627-634 (2007).

33A. Laine, O. et al. Enhanced thrombin formation and fibrinolysis during acute Puumala hantavirus infection. *Thrombosis research* 126, 154-158 (2010).

34.A. Dubis, J. & Witkiewicz, W. The Role of Thrombin-Activatable Fibrinolysis Inhibitor in the Pathophysiology of Hemostasis. *Adv Clin Exp Med* 19, 379-387 (2010).

35A. Bondu-Hawkins, V. et al. Elevated Plasma Cytokine, Thrombin, and PAI-1 Levels in Patients with Severe Hantavirus Cardiopulmonary Syndrome Due to Sin Nombre Virus *Viruses* in press (2014).

36A. Buranda, T. et al. Rapid parallel flow cytometry assays of active GTPases using effector beads. *Analytical biochemistry* 144, 149-157 (2013).

37A. Buranda, T. et al. Equilibrium and Kinetics of Sin Nombre Hantavirus Binding at DAF/CD55 Functionalized Bead Surfaces. *Viruses-Basel* 6, 1091-1111 (2014).

38A. Osuchowski, M. F., Welch, K., Siddiqui, J. & Remick, D. G. Circulating cytokine/inhibitor profiles reshape the understanding of the SIRS/CARS continuum in sepsis and predict mortality. *J Immunol* 177, 1967-1974 (2006).

39. A. Lvovschi, V. et al. Cytokine profiles in sepsis have limited relevance for stratifying patients in the emergency department: a prospective observational study. *PloS one* 6, e28870 (2011).
40. A. van Nieuw Amerongen, G. P., van Delft, S., Vermeer, M. A., Collard, J. G. & van Hinsbergh, V. W. Activation of RhoA by thrombin in endothelial hyperpermeability: role of Rho kinase and protein tyrosine kinases. *Circulation research* 87, 335-340 (2000).
41. A. van Nieuw Amerongen, G. P., Musters, R. J., Eringa, E. C., Sipkema, P. & van Hinsbergh, V. W. Thrombin-induced endothelial barrier disruption in intact microvessels: role of RhoA/Rho kinase-myosin phosphatase axis. *American journal of physiology. Cell physiology* 294, C1234-1241 (2008).
42. A. Stefansson, S., Lawrence, D. A. & Argraves, W. S. Plasminogen activator inhibitor-1 and vitronectin promote the cellular clearance of thrombin by low density lipoprotein receptor-related proteins 1 and 2. *The Journal of biological chemistry* 271, 8215-8220 (1996).
43. A. Rosenfeldt, H., Castellone, M. D., Randazzo, P. A. & Gutkind, J. S. Rac inhibits thrombin-induced Rho activation: evidence of a Pak-dependent GTPase crosstalk. *Journal of molecular signaling* 1, 8 (2006).
44. A. Gavard, J. & Gutkind, J. S. Protein kinase C-related kinase and ROCK are required for thrombin-induced endothelial cell permeability downstream from Galpha12/13 and Galpha11/q. *The Journal of biological chemistry* 283, 29888-29896 (2008), 45. A. Vogel, S. M. et al. Abrogation of thrombin-induced increase in pulmonary microvascular permeability in PAR-1 knockout mice. *Physiol Genomics* 4, 137-145 (2000).
46. A. Boling, B. & Moore, K. Tranexamic acid (TXA) use in trauma. *Journal of emergency nursing: JEN: official publication of the Emergency Department Nurses Association* 38, 496-497 (2012).
47. A. Kawkitinarong, K., Linz-McGillem, L., Birukov, K. G. & Garcia, J. G. Differential regulation of human lung epithelial and endothelial barrier function by thrombin. *American journal of respiratory cell and molecular biology* 31, 517-527 (2004).
48. A. Standage, S. W. & Wong, H. R. Biomarkers for pediatric sepsis and septic shock. *Expert Rev Anti-Infe* 9, 71-79 (2011).
49. A. Hong, T. H. et al. Biomarkers of early sepsis may be correlated with outcome. *J Transl Med* 12 (2014).
50. A. Gavard, J. et al. A role for a CXCR2/phosphatidylinositol 3-kinase gamma signaling axis in acute and chronic vascular permeability. *Molecular and cellular biology* 29, 2469-2480 (2009).
51. A. Duboscq, C. et al. Plasminogen: An important hemostatic parameter in septic patients. *Thrombosis and haemostasis* 77, 1090-1095 (1997).
52. A. Vaughan, D. E. PAI-1 and atherothrombosis. *Journal of Thrombosis and Haemostasis* 3, 1879-1883 (2005).
53. A. Nykjaer, A. et al. Both pro-uPA and uPA: PAI-1 complex bind to the alpha 2-macroglobulin receptor/LDL receptor-related protein. Evidence for multiple independent contacts between the ligands and receptor. *Annals of the New York Academy of Sciences* 737, 483-485 (1994).
54. A. Degryse, B., Sier, C. F., Resnati, M., Conese, M. & Blasi, F. PAI-1 inhibits urokinase-induced chemotaxis by internalizing the urokinase receptor. *FEBS letters* 505, 249-254 (2001).
55. A. Cheung, A. L., Bayer, A. S., Zhang, G., Gresham, H. & Xiong, Y. Q. Regulation of virulence determinants in vitro and in vivo in *Staphylococcus aureus*. *FEMS immunology and medical microbiology* 40, 1-9 (2004).
56. A. Jaffe, A. B. & Hall, A. Rho GTPases: biochemistry and biology. *Annual review of cell and developmental biology* 21, 247-269 (2005).
57. A. Arthur, W. T. & Burridge, K. RhoA inactivation by p190RhoGAP regulates cell spreading and migration by promoting membrane protrusion and polarity. *Molecular biology of the cell* 12, 2711-2720 (2001).
58. A. Benjamini, Y. & Hochberg, Y. Controlling the False Discovery Rate—a Practical and Powerful Approach to Multiple Testing. *J Roy Stat Soc B Met* 57, 289-300 (1995).
59. A. Benjamini, Y., Drai, D., Elmer, G., Kafkafi, N. & Golani, I. Controlling the false discovery rate in behavior genetics research. *Behavioural brain research* 125, 279-284 (2001).
60. A. Koch, A. et al. Circulating soluble urokinase plasminogen activator receptor is stably elevated during the first week of treatment in the intensive care unit and predicts mortality in critically ill patients. *Critical care* 15, R63 (2011).
61. A. Rymer, J. C. et al. A new approach for clinical biological assay comparison and standardization: Application of principal component analysis to a multicenter study of twenty-one carcinoembryonic antigen immunoassay kits. *Clinical Chemistry;* 45, 869-881 (1999).
62. A. Webb-Robertson, B. J. et al. Sequential projection pursuit principal component analysis—dealing with missing data associated with new-omics technologies. *BioTechniques* 54, 165-168 (2013).
63. A. Pooladi, M. et al. Cluster and Principal Component Analysis of Human Glioblastoma Multiforme (GBM) Tumor Proteome. *Iranian journal of cancer prevention* 7, 87-95 (2014).
64. A. Marengo, E. et al. Study of proteomic changes associated with healthy and tumoral murine samples in neuroblastoma by principal component analysis and classification methods. *Clinica chimica acta; international journal of clinical chemistry* 345, 55-67 (2004).
65. A. Alonso-Gutierrez, J. et al. Principal component analysis of proteomics (PCAP) as a tool to direct metabolic engineering. *Metabolic engineering* (2014) 66. A. Dennis, G., Jr. et al. DAVID: Database for Annotation, Visualization, and Integrated Discovery. *Genome biology* 4, P3 (2003).
67. A. Ward, J. H. Hierarchical Grouping to Optimize an Objective Function. *J Am Stat Assoc* 58, 236-& (1963).
68. A. Leitner, G. et al. Effects of intra-mammary bacterial infection with coagulase negative staphylococci and stage of lactation on shedding of epithelial cells and infiltration of leukocytes into milk: Comparison among cows, goats and sheep. *Vet Immunol Immunop* 147, 202-210 (2012).
69. A. Chang, D. W. et al. Proteomic and computational analysis of bronchoalveolar proteins during the course of the acute respiratory distress syndrome. *Am J Resp Crit Care* 178, 701-709 (2008).

Example 3

Rapid Parallel Flow Cytometry Assays of Active GTPases Using Effector Beads.

Here we describe a rapid, bead-based effector-binding assay that can monitor the activation status of multiple GTPases from a single cell lysate derived from <100,000 cells. As proof-of-principle, we demonstrate the utility of the assay in measuring the previously uncharacterized cascade of GTPases that is activated to allow cellular entry of Sin Nombre hantavirus (SNV) in the course of a productive infection.

Hantaviruses, which cause hemorrhagic fever with renal syndrome (HFRS) and hantavirus cardiopulmonary syndrome (HCPS), are of particular interest because their mechanisms of host cell entry and subsequent pathogenesis are poorly understood [9B]. Viruses attach to cell surface receptors, promote the cytoskeletal remodeling required for breaching inter- and intracellular cellular barriers, and enter the cell through endocytic membrane trafficking pathways; all processes that fundamentally depend on the activation of various GTPase cascades [10B]. Parallel measurements of active GTPases downstream of receptor engagement are therefore important for understanding how these signals are regulated and how their consolidation is related to both physiological and pathological contexts.

Materials and Methods

Antibodies

Monoclonal rabbit anti-RAP1 (5G7): sc-47695 and rat monoclonal anti H-Ras (259): sc-35 were obtained from Santa Cruz Biotechnology, Inc (Santa Cruz, CA)

Monoclonal mouse antibodies: anti-Rho (A, B, C) clone 55 (#05-7788), anti-Rac1, clone 23A8, #05-389, the secondary antibody goat anti-mouse IgG (H+L) conjugated to Alexa Fluor 488, Rabbit Polyclonal anti Cdc42 #07-1466 were obtained from Millipore (Temecula, CA). Mouse Monoclonal Anti Rac1 #ARC03 was also purchased from Cytoskelton Inc. (Denver, CO). Mouse monoclonal anti-Rab 7 antibody was from Sigma-Aldrich (St. Louis, MO). Mouse monoclonal AP5 B3 anti LIBS antibody was purchased from the Wisconsin Blood Center, Activators and Inhibitors Rap1 Activator 8-Cpt-2me-cAMP was used at 50 µM and from R & D Systems (Minneapolis, MN). Rac1 Inhibitor, NSC23766 was used at 100 AM and from Calbiochem Inc. (now www.emdmillipore.com). Calpeptin (Rho activator) was used at 0.3 µM and from Calbiochem Inc. The human recombinant form of the catalytic domain of p50RhoGAP from Cytskeleton Inc. (Denver, CO) was used at 2.50 µg/µl. Recombinant EGF was used at 10 nM and was from Life Technologies (Carlsbad, CA). The novel Cdc42 inhibitor CID2950007 was used at 10 µM synthesized and characterized as previously described [6B] and can be purchased commercially as ML141.

Buffers

RIPA buffer: 74 mM $CaCl_2$), 50 mM Tris-HCl pH 7.4, 1% NP-40 (v/v), 0.5% (w/v) deoxycholic acid, 0.1% (w/v) SDS, 1 mM sodium orthovanadate, and protease inhibitors. HHB buffer: 7.98 g/L HEPES (Na salt), 6.43 g/L NaCl, 0.75 g/L KCl, 0.095 g/L $MgCl_2$ and 1.802 g/L glucose.

Cell Culture

HeLa and Vero E6 cells from ATCC were plated at $2 \times 10^4$ cells per well in a 48-well plate, then allowed to grow for ~48 h to medium/low confluence in Dulbecco's Modified Eagle Medium (DMEM) supplemented with 10% FBS, pen/strep, and L-glutamine in a 37° C. incubator with 5% $CO_2$.

Production of Sin Nombre Virus

SNV was propagated and titered in Vero E6 cells under strict standard operating procedures using biosafety level 3 (BSL3) facilities and practices (CDC registration number C20041018-0267) as previously described [11]. For preparation of UV-inactivated SNV, we placed 100 µL of virus stock (typically $1.5-2 \times 10^6$ focus forming units/ml) in each well of a 96-well plate and subjected the virus to UV irradiation at 254 nm for various time intervals (~5 $mW/cm^2$) as described elsewhere [12B]. We verified efficiency of virus inactivation by focus assay before removing from the BSL-3 facility.

Fluorecent Labeling of SNV

The envelope membrane of hantavirus particles was stained with the lipophilic lipid probe octadecylrhodamine (R18) and purified as previously described [12B]. The typical yield of viral preparation was $1 \pm 0.5 \times 10^8$ particles/µl in 300 µl tagged with ~10,000 R18 probes/particle or 2.7 mole % R18 probes in the envelope membrane of each particle of 192 om diameter average size [12B]. Samples were aliquoted and stored in 0.1% HSA HHB buffer, and used within two days of preparation and storage at 4° C. For long-term storage, small aliquots suitable for single use were stored at −80° C.

Effector Proteins

The GST-effector chimeras consisting of the minimal GTPase binding domains (RBD) used for the studies were as follows. PAK-1 RBD, a Rac1 effector and Raf-1 RBD, a RAS effector protein were obtained from Millipore. Rhotekin-RBD, a Rho effector protein was purchased from Cytoskeleton Inc. RalGDS-RBD, a RAP1 effector protein was expressed and purified from a plasmid kindly provided by Dr. Burridge (UNC Chapel Hill) [13B]. GST-RILP RBD was purified as described below.

Expression and Purification of GST-RILP

A plasmid encoding GST-RILP RBD was prepared by Daniel Cimino as previously described [14B]. Protein was expressed in competent *E. coli* BL21 cells. Cultures were grown at 37° C. to an absorbance of 0.5 O.D. measured at 595 nm and protein expression induced by transfer to room temperature and addition of 0.2 mM isopropyl-beta-D-1-thiogalactopyranoside (IPTG) for 16-18 h to maximize the yield of properly folded active fusion protein. Purification of GST-RILP was performed according to standard procedures and as previously described [15B] [16B]. Briefly, the harvested bacterial cell pellet was resuspended in cold PBS. Cells were lysed using lysozyme and a microtip sonicator (Misonix Inc., Newtown, CT, U.S.A.). The cell lysates were mixed with 10% Triton X-100 and mixed end over end for 30 min at 4° C. Lysates were then centrifuged at 8,000×g for 10 min to pellet the cellular debris. The supernatant was mixed with freshly prepared Glutathione Sepharose 4B slurry and bound at 4° C. for 2 h using gentle agitation to keep the resin suspended in the lysate solution. Glutathione beads with bound protein were settled using low speed centrifugation (500×g) followed by multiple washes before eluting the bound GST-tagged protein with 10 mM glutathione in 50 mM Tris-HCl elution buffer. Eluted protein was concentrated by passing through Millipore Amplicon Ultra Tubes (MWCO 30,000). The purified protein was quantified using the BCA protein estimation kit (Pierce, City, State). Single use aliquots stored at −80° C. were used in the experiments.

Preparation of GSH Beads

13 µm Superdex peptide beads were derivatized with glutathione (γ-glu-cys-gly or GSH) as previously described [7; 15; 16]. 5 µm Cyto-Plex™ carboxylated beads (FM5CR0L L=1, 2, 3, . . . 12) dyed with graded levels (L) of red emission were purchased from Thermo Scientific (City, State). The beads were then functionalized with glutathione as previously described [17B]. Briefly, the carboxyl functionalized beads were converted to amine reactive N-hydroxysulfosuccinimide (Sulfo-NHS) esters using 1-ethyl-3-[3-dimethylaminopropyl] carbodiimide hydrochloride (EDC or EDAC) chemistry following protocols provided by the manufacturer (Thermo Scientific). The amino derivatized beads were then reacted with a bifunctional chemical crosslinker succinimidyl 4-[N-malcimidomethyl]-cyclohexane-1-carboxylate (SMCC) in order to enable subsequent attachment of GSH. 5×10 beads were suspended in 400 µl of 50 mM sodium phosphate buffer (pH 7.5) containing 0.01% Tween-20 (w/v) and mixed with 8 µl of 100 mM SMCC in dimethyl sulfoxide (DMSO) and incubated with mild agitation for 30 min. The beads were centrifuged and resuspended in 360 µL of fresh buffer together with 40 µl of 200 mM GSH (pH 7) and 4 µl of 100 mM EDTA (pH 7-8). Nitrogen was bubbled slowly through the suspension for 5 min, the tube was capped to exclude oxygen, and the beads were gently mixed for 30 min. The beads were washed four times and stored in single use aliquots in 30 mM HEPES (pH 7.5), 100 mM KCl, 20 mM NaCl, 1 mM EDTA, and 0.02% $NaN_3$ at 4° C.

Assembly of GST Effector Proteins on GSH Beads and GST Pull-Down Assay

Site occupancy (θ) of GSH sites on beads (limiting reagent) is regulated by the dissociation constant $K_d$ and concentration of free glutathione-S-transferase (GST) fused to effector proteins, according to Equation (1):

$$\theta=([GST]_{free}/K_d)/(1+([GST]_{free}/K_d)) \quad (1)$$

We relied on previous studies wherein the characteristic kinetic and equilibrium binding constants ($K_d$~80 nM) of GST fused to Green fluorescent protein (GFP) were documented [7B; 15B; 16B;17B; 19B], to establish optimal stoichiometric mixtures of GSH beads and specific GST effector fusion proteins for obtaining saturating site occupancies of the GST effector proteins for the present work. Typical site occupancies of the beads at saturation are in the $1-4\times10^6$ ligand sites/bead range. For example, 10,000 beads present an upper limit of $4\times10^{10}$ sites or 3.3 nM in 20 µL. Incubating 800 nM ($10\times K_d$) of GST effector protein with the GSH beads is expected to yield a bead site occupancy, θ, of 0.91 (or 91%). In this way, known quantities of beads were mixed with effector proteins of known concentration at the desired stoichiometry range, incubated with shaking for 2 h at 4° C., centrifuged, and resuspended in RIPA buffer at 10,000 beads/tube. Effector-bearing beads were prepared fresh for each experiment and kept on ice while cell lysates were prepared.

Configurations of the GTPase Effector Trap Flow Cytometry Assay (G-Trap)

Vero B6 or HeLa cells were plated in 48 well plates or T 75 flasks and incubated overnight in culture media. Cells were starved for overnight in serum-free medium followed by stimulation with activator or inhibitor at concentrations and times shown in the Results section. After incubating cells with various inhibitors, activators, and/or $SNV^{R18}$ for desired times, cells were lysed with 100 µL ice-cold RIPA buffer. For the purposes of standardization, a fraction of the supernatant was collected to measure protein concentrations. Lysates were kept ice cold at all times to limit hydrolysis of active GTPases. Lysates were sonicated briefly, and then centrifuged at 14,000 rpm for 10 min to clear the lysate of any unlysed materials and DNA. For each effector assay, 10,000 beads were added to 50 μg of protein in 100 μl of cell lysate in RIPA buffer. The beads and lysate were allowed to incubate for 1 h at 4° C. After incubation, the beads were pelleted in a cold centrifuge. The bead pellets were resuspended in RIPA buffer and incubated with a primary monoclonal antibody for the target GTPase, with gentle shaking for 1 h. Depending on availability, the residual lysates were collected and re-assayed for a different GTPase by adding the appropriate effector beads. Lysates may be saved for future assays by flash freezing in liquid nitrogen, then storing at −20° C. for up to one week. To minimize reporter antibody crosstalk, samples were split into separate fractions after lysate binding to the multiplex bead sets and then individually probed with a reporter antibody specific for a single target GTPase per fraction. The beads were than centrifuged and resuspended in 10% BSA HHB buffer with an Alexa 488 secondary antibody at a 1:200 dilution for 1 h with shaking at 4° C. Finally the beads were centrifuged once more and resuspended in 100 μL RIPA buffer for reading on the flow cytometer.

PI-PLC Treatment

To determine whether cytoskeletal remodeling was caused by the specific interaction of $SNV^{R18}$ with DAF, Vero E6 cells were treated with phosphatidylinositol-specific phospholipase C (PI-PLC), an enzyme known to cleave GPI-anchored proteins from cell surfaces [20B; 21B]. Monolayers of Vero E6 cells plated in 8-well Lab-Tek chambers were washed with HHB and treated with 1.0 unit of PI-PLC from *Bacillus cereus* (Life Technologies, Carlsbad, CA). After incubation at 37° C. for 30 min, cells were washed and resuspended in HHB buffer and analyzed at the microscope.

GLISA

Colorimetric based, commercial kits (Cytoskeleton Inc., Denver, CO) for measuring Rho GTPase activation were used to measure SNV induced activation of Rac1 and RhoA in Vero E6 cells. About 8×$10^4$ Vero E6 cells were plated in a 12-well plate in RPMI 1640 medium. After reaching 50-60% confluency, the media was replaced with starvation media containing 0.5% BSA. Cells were then serum starved for 24 h before treatment with ~$10^9$ SNV particles at different time points, Media conditions included calcium ($Ca^{2+}$), and PI-PLC (as described above). Cells were washed with ice cold PBS and then lysed and prepared for protein assays. Positive controls included purified Rac1-GTP and RhoA-GTP provided in the kit and were used to quantify active GTPase levels in the cell lysates. Negative controls included buffer-only controls, and cell lysates prepared from quiescent control cells after serum starvation. Cell lysates were frozen, and active Rac1 levels were quantified based on a p21-activated protein kinase binding assay [22], whereas active RhoA was quantified based on a Rhotekin binding assay [23]. All assays were performed in 96-well microtiter plates.

Stress Fiber Assay for RhoA Activation

RhoA activation was independently confirmed by monitoring actin stress fiber formation following calpeptin or SNV stimulation (1 μg/ml) for 30 min. Actin filaments in control and stimulated cells were detected following paraformaldehyde (4%) fixation and Triton X-100 (0.5%) permeabilization using Alexa Fluor® 488 phalloidin (1 unit, or 0.17 M) (Life Technologies).

Confocal Microscopy of $SNV^{R18}$

For live cell imaging of virus binding and endocytosis, Vero E6 cells were plated in 8-well Lab-Tek chambers (Nunc) and temperature was maintained at 30° C. with an objective heater (Bioscience Tools) in appropriate buffer containing the desired cations, $Ca^{2+}$ or $Mn^{2+}$ which respectively confer low and high affinity states of $a_v\beta_3$ [24B]. In situ addition of $SNV^{R18}$ was performed by micropipeting an aliquot (100 μL) of ≈1×$10^9$ virus particles per well containing ≈1.5×$10^5$cells in 200 μl in HBSS and mixing well by trituration with the pipet. Confocal laser scanning microscopy was performed with Zeiss META or LSM 510 systems using 63× 1.4 oil immersion objectives as previously described [24B]. Images were collected using 2× line averaging at 3-10 s intervals, depending on imaging time, where longer intervals were necessary to minimize photobleaching.

Results and Discussion

Configuration and General Applicability of G-Trap Assay

Measurements of the activity of several GTPases in receptor-stimulated cells makes use of micron-sized glutathione beads that are individually functionalized with GST-tagged cognate effector protein and specific for individual target small GTPases. To simplify bacterial expression and purification of effector proteins, only the GTPase binding domains (RBD) are used. Effector coated beads are incubated with cell lysates that contain active, GTP-bound Ras, Rho and Rab GTPases. The GTPases are selectively recruited to beads that bear the cognate effector and are detected directly using fluorophore conjugated monoclonal antibodies specific for each GTPase or indirectly using secondary antibodies with fluorophore tags. It is important to note that the optimal signal-ratio between site occupancy of effector beads exposed to resting and activated cell lysates is achieved by not using large excesses of cell lysate proteins. This is because the effector beads are nominally used as limiting reagents, and therefore can approach saturation even in the resting cell lysate. This would obscure the accurate detection of increased activity status of GTPases in stimulated cell lysates. Impirically, we found that 10,000 beads and 50 µg protein in 100 µl were optimal for each effector assay (see methods).

Figure 11:
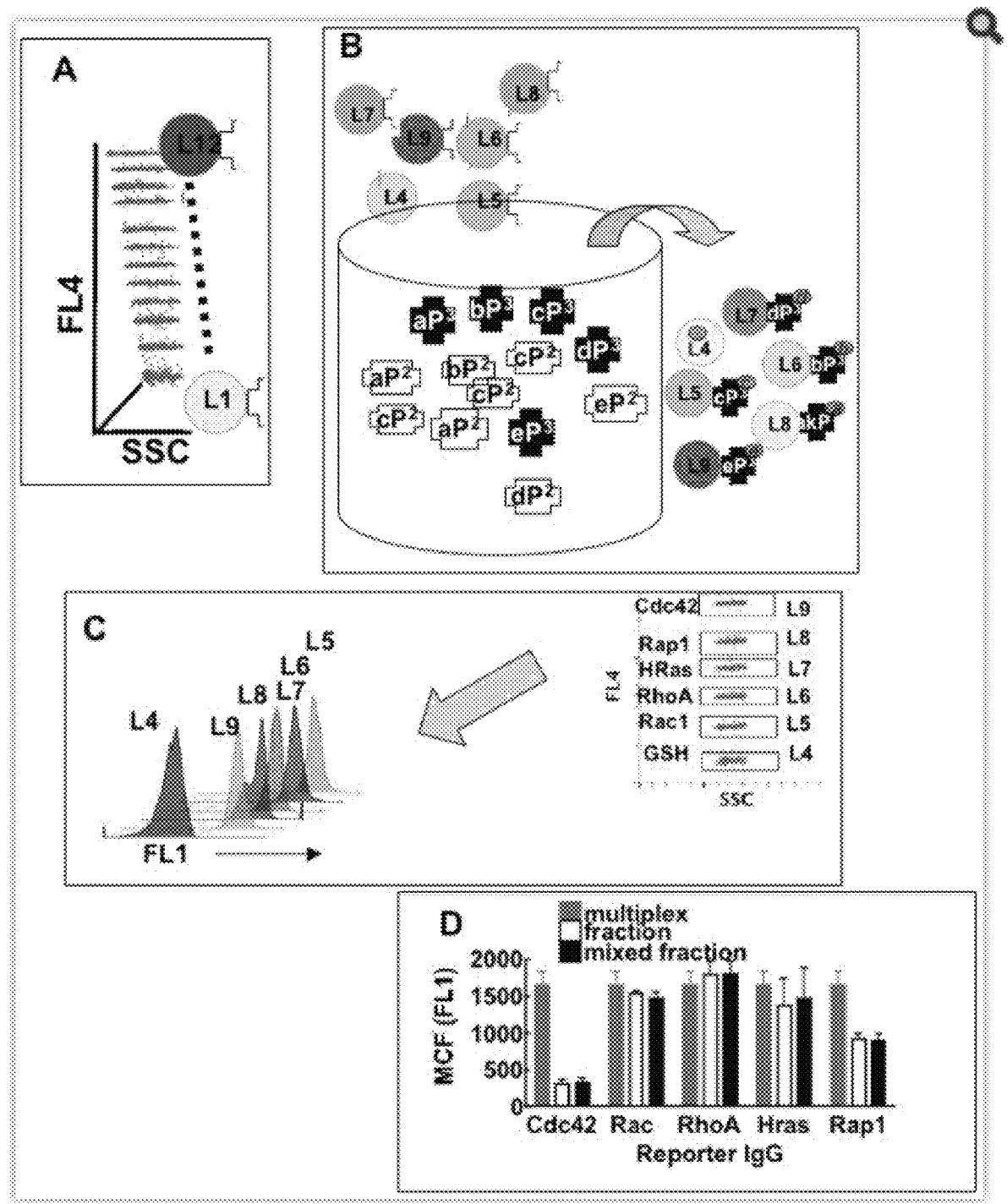

In multiplex configuration distinct effectors were immobilized on Cytoplex™ beads of graded fluorescence intensities of a fluorophore with a fixed red wavelength of 700 nm [19B] (FIG. 11). An extra set of effector free beads was used as a control for nonspecific binding (e.g. L4 in FIG. 11B. To assess the degree of nonspecific reporter antibody crosstalk during the labeling step, we measured the levels of binding to unconjugated GSH beads using a mixture of reporter antibodies for RhoA, Rac, Cdc42, H-Ras and Rap1 GTPases under the following three conditions: a) GSH beads mixed with all antibodies and measurement of the aggregate fluorescence of nonspecifically bound antibodies (multiplex in FIG. 11D), b) individual bead populations were treated with each antibody separately and measured separately (fraction in FIG. 11D), c) individual bead populations were treated with each antibody separately, then combined and measured as a single mixture (mixed fraction in FIG. 11D). For the five GTPase antibodies tested, the multiplex sample was comparable to fraction and mixed fraction samples for the Rac1, RhoA, and Rap1 antibodies but higher for Cdc42 and H-Ras antibodies. The degree of non-specific binding depends on antibody type, batch and supplier.

Figure 12:
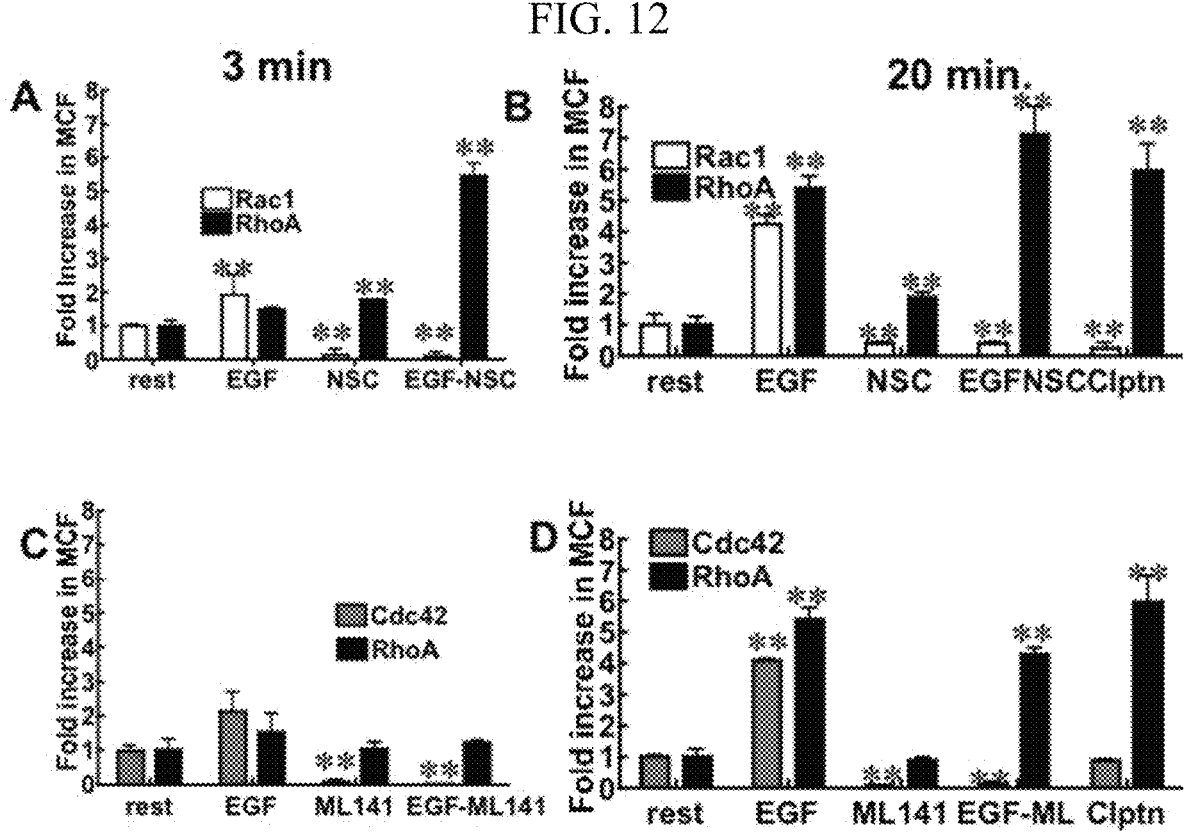

Therefore, it is important for the user to be familiar with binding characteristics of new antibody batches before using them in multiplex format. In the present application, non-specific binding values shown in FIG. 11D, were significantly lower (>5 fold to ≥30 fold) than fluorescence signals associated with resting and activated cells, depending on assay conditions (cf. FIG. 12). In these circumstances errors from non-specific binding are trivial. However, in cases were the fluorescence signals associated with specific GTPase-activity assays are of comparable order of magnitude to nonspecific background readings (e.g. NSC23766 or ML141 treated cells in FIG. 12), it is important to modify the multiplex protocol. This can be addressed by adopting the mixed fraction format, where multiplexed samples that are recovered from the lysates are partitioned into fractions that correspond to the number of target analytes, and stained separately with reporter antibodies. In the case of the example shown in FIG. 1B-D, Cdc42 and Rap1, may be stained with reporter antibodies as separate fractions, while Rac1, RhoA and HRas can be treated as a full multiplex. In summary it is important for the user to be familiar with binding characteristics of antibody batches before using them in a format of the G-trap assay that is most suitable for the prevailing conditions.

G-Trap Assay Validation

Cdc42, Rac1 and RhoA are among the most well characterized members of the Rho subfamily of GTPases. They are known for orchestrating cytoskeletal reorganization dynamics (filamentous actin and myosin 2) and crosstalk to antagonize each other's activities [25B; 26B; 27B; 28B]. The availability of specific regulators of their activity makes these GTPases a suitable platform to test the applicability of our G-trap assay. HeLa cells were treated with the following signaling regulators: 1) NSC23766, a specific inhibitor of Rac1 interaction with its two upstream GEFs Tiam1 and Trio (Trio is also identified as a RhoA target [29B; 30B]), 2) CID2950007, a novel Cdc42 specific inhibitor [6B] commercially sold as ML 141, and 3) calpeptin, an upstream activator of RhoA [31B]. Cdc42, Rac1 and RhoA were activated by adding 10 nM EGF to cells. Readings were taken at 3 min and 20 min after stimulation. The data were corrected for nonspecific binding by subtracting the fluorescent antibody binding to the GST-conjugated control beads from the antibody binding to GST-effector bearing beads. EGF-stimulated cell samples were normalized to unstimulated resting control cell samples. Data were collected 3 min (FIGS. 12A, 12C) and 20 min (FIGS. 12B and 12D) post-EGF-stimulation. RhoA data were separately paired with Rac1 and Cdc42 for ease of comparison of the putative antagonists. The activation of RhoA lagged behind both Rac1 and Cdc42 activation, at 3 min and supplanted both Cdc42 and Rac1 at 20 min. At this juncture it is not yet clear whether the time-dependent dominance in the relative amplitudes of Rac1 and RhoA are due to their mutual antagonism. Cell treatment with the Rac1-GEF inhibitor, NSC23766, suppressed Rac1 while RhoA activity was elevated relative to resting cells. Treatment of cells with EGF and NSC23766 in combination resulted in a dramatic activation of RhoA (>5-fold relative to resting cells) that was well above the activation of RhoA observed following EGF-stimulation alone. Calpeptin-mediated activation of RhoA was tested for comparison and found to be accompanied by a concomitant decrease in Rac1 activity. Collectively, these data are consistent with the known mutual antagonism of Rac1 and RhoA [25B;32B]; wherein the inhibition of Rac1 is sensed and results in amplified RhoA activity in the absense of a counteracting Rac1 effect. The targeted activity of NSC23766 against Rac1 and not RhoA suggests that Trio is not an important upstream factor for RhoA activation under our experimental conditions. Interestingly, though Rac1 and Cdc42 are believed to have partially overlapping functions in mediating the formation of actin-rich protrusions in migrating cells [2B; 33B], the total inhibition of Cdc42 had no effect on RhoA activity under our experimental conditions (FIGS. 12C and 12D) as previously shown [6B]. These results suggest that under our experimental conditions, the up or downstream effector signals associated with Cdc42 do not impinge on or regulate RhoA and vice versa. Together the data demonstrate the power of the G-trap assay in sensitively and temporally dissecting GTPase responses to stimuli and pharmacologic manipulation.

Figure 13:
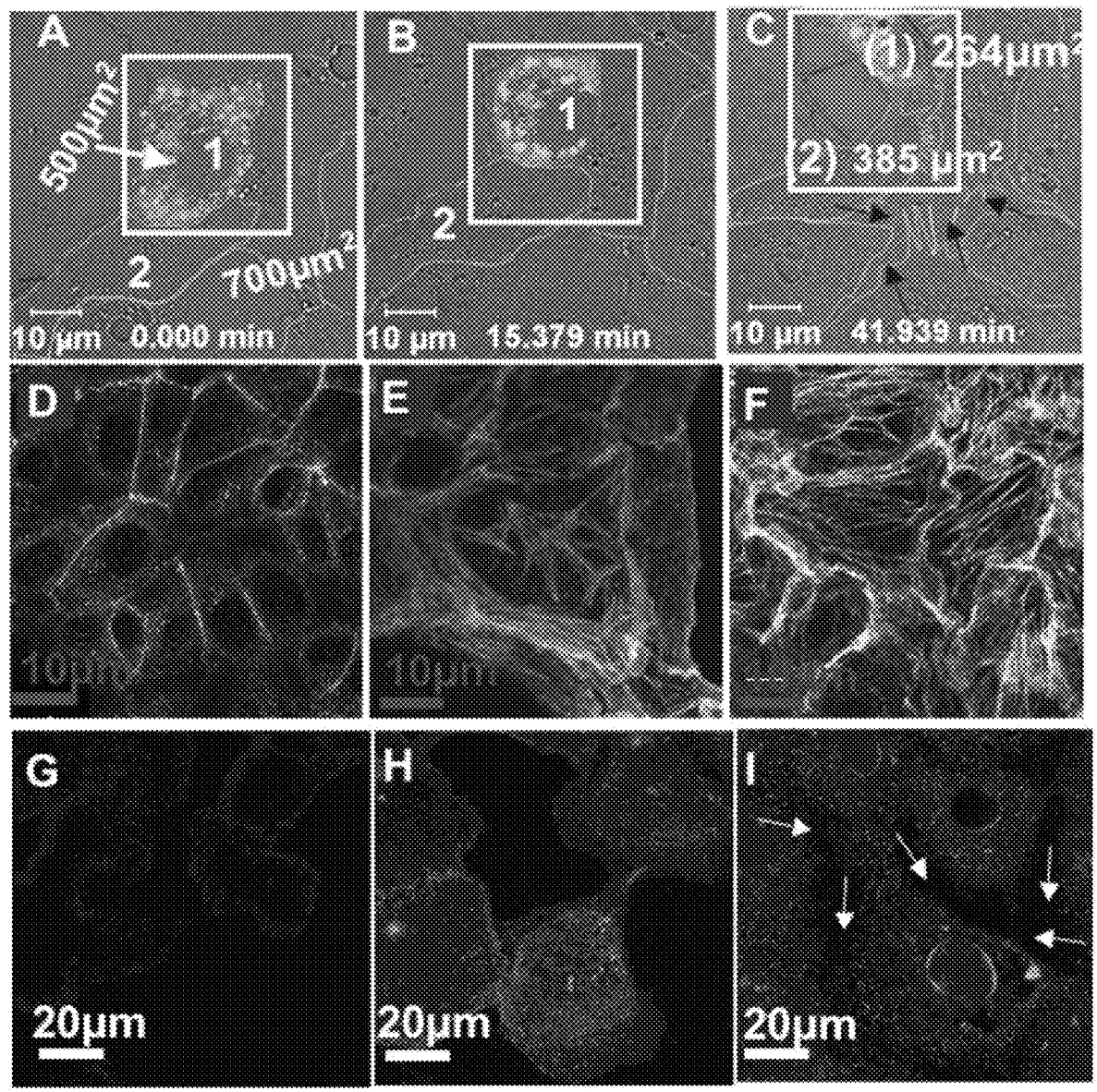
FIGS. 13. A, B, C, D, E, F, G, H, and I show UV-killed SNV$^{R18}$ induces vigorous remodeling of the actin cytoskeleton of Vero E6 cells, causing loss of cell adhesion. Confocal microscopy images of resting Vero E6 monolayers transiently transfected with the cell adhesion marker, paxillin GFP. Individual cells are outlined. A. Cells designated 1 and 2 before virus exposure are also defined by their surface area. The white square was included as size reference for cell 1. B. After 15 min exposure to 10,000 SNV$^{R18}$ particles/cell the size of reference cell/is decreased relative to the rectangular marker. C. Time lapse frame taken 42 min after cells were exposed SNV$^{R18}$ shows how cells 1 and 2 shrank in size and lost cell adhesion to each other and the coverslip. Arrows mark broken cell-cell junctions. D. Resting Vero E6 cells stained for actin with Alexa Fluor 488® phalloidin. E. RhoA induced F-actin stress fibers are shown 15 min activation with calpeptin and F. after SNV treatment. G. Resting Vero cells stained with integrin affinity sensitive AP-5 antibodies. H. Increased AP-5 staining in Mn$^{2+}$ activated cells. I. Detection of differential activation of $\beta_3$integrins at the perinuclear and peripheral regions of Vero cells using AP5 antibodies. Arrows mark broken cell-cell junctions.

Monitoring Virus-Induced GTPase Activation: Morphologic and Biochemical Assessment Exposure of Vero E6 cells to known titers of UV killed and fluorescently labeled SNV particles causes cells to contract, lose cell contacts, and form filopodia, lamellipodia and stress fibers (FIG. 13A-F). Ultimately the virus is internalized and present in Rab7 positive late endosomes. Such morphological changes and membrane trafficking events are anticipated to be associated with the changes in the activities of multiple GTPases. Actin based structure changes are associated with Cdc42 (filopodia), Rac1 (lamellipodia), and RhoA (stress fiber formation and cellular contraction) [34B]. Staining for actin with Alexa Fluor 488® phalloidin, identified RhoA induced F-actin stress fibers formed in response of treatment of resting cells with calpeptin (compare FIG. 13D vs. 13E) were similar to the stress fibers formed in response to SNV exposure (FIG. 13F). The ruffling observed in SNV-treated cells is similar to that seen in response to EGF-mediated activation of Rac1-dependent ruffling [35B-B], The loss of cell adhesion is connected to integrin affinity regulation, which is presumed to be downstream of antagonistic Rap1 and H-Ras activity [36B] [37B]. AP-5 monoclonal antibodies recognize the PSI domain of extended conformation activated $\beta_3$ integrins at the cell surface [38B] and enabled detection of the onset of cellular detachment at the cell junctions in virus treated cells; based on poor APS staining of the plasma membrane and instead a strong perinuclear substratum staining (arrows in FIG. 13I). See for comparison resting and $Mn^{2+}$ stimulated (maximal cell surface integrin activation) controls (FIG. 13G-H), All of the described morphologic indicators of changes in GTPase activity prompted us to use conventional GLISAs in comparison with our G-trap assay for monitoring the activation status of individual GTPases in SNV treated cells.

Figure 4:
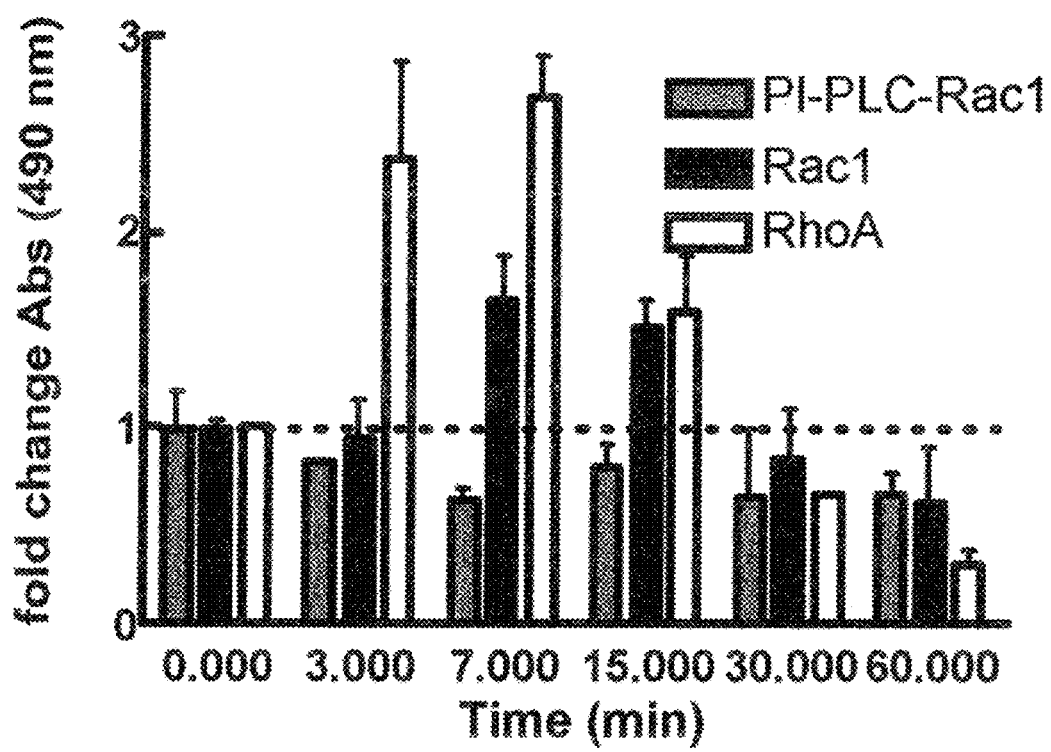
FIG. 4 shows that SNV induces upregulation of GTP bound RhoGTPases in Vero E6 cells. Bar graph shows GLISAs measuring kinetics of adhesion-dependent Rho protein (Rac all other conditions are the same as Panel A. C. Conditions as in Panel A measuring changes in active Cdc42 and RhoA. ML141 or CID2950007 served as the Cdc42 specific inhibitor. D. Conditions as in Panel B with applicable changes for Cdc42. The errors represent standard deviation of 3 independent experiments measured in duplicate each time. **P<0.001 for all data compared to resting (rest) cells.

We first used GLISA assays to measure Rho GTPase activation as a function of virus exposure time of wild-type Vero cells and cells where surface-expressed DAF was first cleaved with PI-PLC [20B] (FIG. 4). Virus treatment resulted in a robust activation of first RhoA at 3 min and subsequently Rac1 at 7 min with both falling to baseline levels by 30 min. After 60 min of virus exposure the levels of active GTP-Rho and -Rac fell below baseline levels, most likely because the expression of GTP-bound Rho GTPases is regulated by cell-cell and cell-matrix adhesion [33B] [39B]. In DAF-cleared cells, Rac1 failed to be activated across all timepoints indicating that virus engagement of a GPI anchored receptor such as DAF was required upstream of Rac1 activation. It is important to note that, the GLISA assays were performed separately on different days using different cell lysates, therefore the relative amplitudes of RhoA and Rac1 can not be accurately correlated to their temporal responses in the same way that the G-trap data shown in FIG. 12 was analyzed.

We next turned to the G-trap assay to examine the induction Rho protein activity in virus treated Vero E6 cells. Using known Rho GTPase activators and inhibitors the assay validation experiments (FIG. 12B) and results were recapitulated using permissive Vero E6 cells. In virus stimulated cell lysates (FIG. 14A) and analogous to the GLISA results, RhoA activity increased >4-fold above resting levels within 3 min post-treatment. Active Rac1 levels also increased to a lesser extent at the 3 min timepoint. At the 20 min timepoint timepoint, the activity of both GTPases decrease to baseline levels confirming the trend documented by GLISA above (compare FIG. 4 vs. FIG. 14A). The temporal overlap in the activation of RhoA and Rac1 implies that SNV binding induces signaling cascades that lie upstream of RhoA and Rac1 activation, which mirrors what has been observed in a study on Group B Coxsackievirus-activated cells [40B]. Rac1 and Rho normally mutually suppress each other's activity in response to single stimuli as affirmed in 12 and elsewhere in the literature [2B; 25B; 41B]. Their apparent co-stimulation by the virus may reflect the activation of multiple signaling cascades through sequential events with distinct spatial and temporal characteristics [32]. This notion is further supported by the simultaneous visualization of multiple GTPase biosensors during cell migration where surprisingly RhoA was activated exclusively near the cell edge connected with leading-edge advancement. In contrast, Cdc42 and Rac1 were activated away from the leading edge with a delay of ~40 seconds [25B].

The potential roles of the mutually antagonistic Rap1 and H-Ras downstream of SNV signals that lead to loss in cell adhesion were also examined by G-trap assay. Beads functionalized with effectors for Rap1 (GST RalGDS-RBD) and H-Ras (Raf-1 RBD) were used to simultaneously assay activated Rap1, and H-Ras GTPases from cell lysates of virus treated cells. An activator of Epac/Rap1, 8-Cpt-2m-cAMP, served as a specificity control. Activation of Rap1 by 8-Cpt-2m-CAMP was readily demonstrated and as expected decreased basal levels of H-Ras in the G-trap assay [42B]. The activity of Rap1 and H-Ras in virus-activated cell lysates at 3 min and 20 min post-exposure showed that the GTPase pair was activated sequentially, where active Rap 1 peaked within the first 3 min and subsequently declined at 20 min. H-Ras remained low while Rap1 was at its zenith, eventually peaking at 20 min as active Rap1 was in decline. The coincidence between high H-Ras activity and loss of cell-cell adhesion might be linked to the proclivity of H-Ras to suppress integrin activity [43B] (cf. FIG. 13F).

Figure 14:
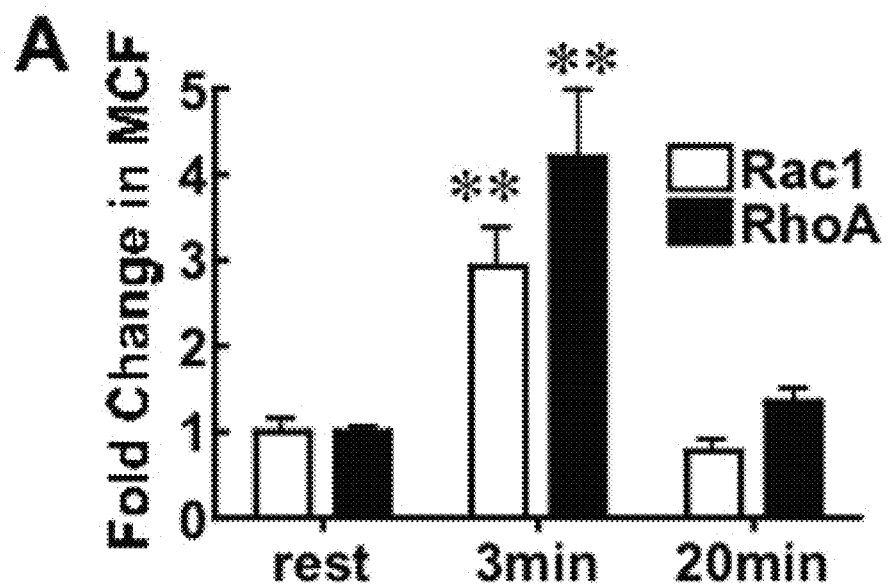
FIGS. 14. A and B show SNV induces the activity of several GTPases in Vero E6 cells. A. Vero E6 cells were serum starved for 24 h and treated with 10,000 SNV$^{R18}$/cell. Active Rac1 and RhoA were detected in cell lysates at 3 min and 20 min after virus exposure using PAK1 and Rhotekin beads, respectively. The errors represent standard deviations in 3 separate measurements. B. Rap1 and H-Ras were sequentially activated by SNV$^{R18}$ in Vero E6 cells. Vero E6 cells were serum starved for 24 h and treated with 10,000 SNV$^{R18}$/cell. Active Rap1 and H-Ras were measured on Ra1 and Raf-functionalized beads, respectively, at 3 and 20 min after virus exposure. Cells were treated with the cAMP analog 8-pCPT-2'-O-methyl-cAMP (O-Me-cAMP), which stimulates the Epac/Rap1 pathway as a specificity control. Error bars represent standard deviations 3 separate measurements.
Figure 14:
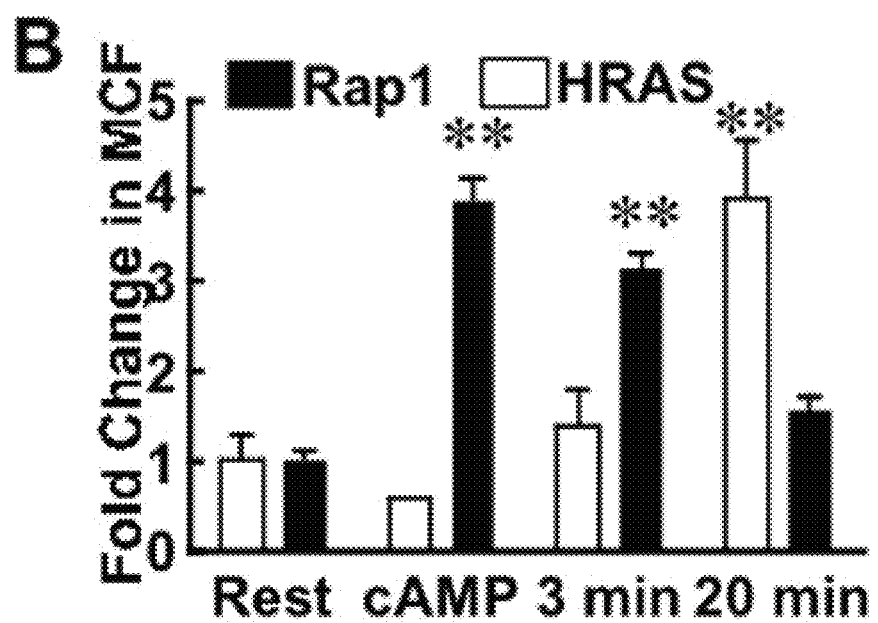

Finally, the activation status of GTPases involved in the intracellular transport of virus particles following internalization, were assessed by monitoring the levels of active Rab7, a GTPase associated with early to late endosome and lysosomal transport [14B; 44B; 45B]. Active, GTP-bound Rab7 levels peaked 15 min following virus exposure (FIG. 14B). The timing of maximal Rab7 coincides with the timing of fluorescently labeled SNV delivery to perinuclear late endosomes traced by microscopy. The time frame is also within the range reported for the delivery of other large viral cargoes to Rab7-positive late endosomes [46B; 47B].

In sum, we have devised a novel, cost effective, flow cytometry-compatible, bead-based effector-binding assay (G-trap) for rapidly monitoring the activation status of multiple members of the Ras GTPase superfamily in cell lysates. We have validated the assay through the use of known agonists and antagonists of individual GTPases. The study provides previously unknown mechanistic detail about SNV induced activation of cellular signaling to promote virus entry and transport. We have recently used a novel inhibitor to define the involvement of Cdc42 GTPase in the lifecycle of Sin Nombre virus infection [6B]. Selective pharmacological inhibitors of the active GTPases can be paired with the G-trap assay to further define the signaling pathways that are important for regulating the lifecycles of pathogens that rely on the same processes. In similar vein we have shown that Y27632, the inhibitor of RhoA kinase (ROCK), blocks the loss of cell barrier function in polarized endothelial cells and thus limits viral infection (Buranda, unpublished results). We therefore anticipate that this approach will enable investigations into the interconnection of signaling networks via GTPase cascades in normal cellular functions as compared to viral or bacterial infections or other pathogenic processes.

REFERENCES

1B. Jaffe A B, Hall A. Rho GTPases: biochemistry and biology. Annu Rev Cell Dev Biol. 2005; 21:247-69.
2B. Guilluy C, Garcia-Mata R, Burridge K. Rho protein crosstalk: another social network? Trends Cell Biol. 2011.
3B. Cherfils J, Zeghouf M. Regulation of small GTPases by GEFs, GAPs, and GDIs. Physiol Rev. 2013; 93:269-309.
4B. Schiller M R. Coupling receptor tyrosine kinases to Rho GTPases—GEFs what's the link. Cell Signal. 2006; 18:1834-43.
5B. Moon S Y, Zheng Y. Rho GTPase-activating proteins in cell regulation. Trends Cell Biol. 2003; 13:13-22.
6B. Hong L, Kenney S R, Phillips G K, Simpson D, Schroeder C E, Noth J, Romero E, Swanson S, Waller A, Strouse J J, Carter M, Chigaev A, Ursu O, Oprea T, Hjelle B, Golden J E, Aube J, Hudson L G, Buranda T, Sklar L A, Wandinger-Ness A. Characterization of a cdc42 protein inhibitor and its use as a molecular probe. J Biol Chem. 2013; 288:8531-43.
7B. Agola J O, Hong L, Surviladze Z, Ursu O, Waller A, Strouse J J, Simpson D S, Schroeder C E, Oprea T I, Golden J E, Aube J, Buranda T, Sklar L A, Wandinger-Ness A. A competitive nucleotide binding inhibitor: in vitro characterization of Rab7 GTPase inhibition. ACS Chem Biol. 2012; 7:1095-108.
8B. Friesland A, Zhao Y, Chen Y H, Wang L, Zhou H, Lu Q. Small molecule targeting Cdc42-intersectin interaction disrupts Golgi organization and suppresses cell motility. Proc Natl Acad Sci USA. 2013; 110:1261-6.
9B. Safronetz D, Ebihara H, Feldmann H, Hooper J W. The Syrian hamster model of hantavirus pulmonary syndrome. Antiviral Res. 2012; 95:282-92.
10B. Grove J, Marsh M. Host-pathogen interactions: The cell biology of receptor-mediated virus entry. J Cell Biol. 2011; 195:1071-82.
11B. Bharadwaj M, Lyons C R, Wortman I A, Hjelle B. Intramuscular inoculation of Sin Nombre hantavirus cDNAs induces cellular and humoral immune responses in BALB/c mice. Vaccine. 1999; 17:2836-43.
12B. Buranda T, Wu Y, Perez D, Jett S D, Bondu-Hawkins V, Ye C, Lopez G P, Edwards B, Hall P, Larson R S, Sklar L A, Hjelle B. Recognition of DAF and avb3 by inactivated Hantaviruses, towards the development of HITS flow cytometry assays. Anal Biochem. 2010; 402:151-160.
13B. Wittchen E S, Burridge K. Analysis of low molecular weight GTPase activity in endothelial cell cultures. Methods Enzymol. 2008; 443:285-98.
14B. Colucci A M, Spinosa M R, Bucci C. Expression, assay, and functional properties of RILP. Methods Enzymol. 2005; 403:664-75.
15B. Tessema M, Simons P C, Cimino D F, Sanchez L, Waller A, Posner R G, Wandinger-Ness A, Prossnitz E R, Sklar L A. Glutathione-S-transferase-green fluorescent protein fusion protein reveals slow dissociation from high site density beads and measures free GSH. Cytometry A. 2006; 69:326-34.
16B. Schwartz S L, Tessema M, Buranda T, Pylypenko O, Rak A, Simons P C, Surviladze Z, Sklar L A, Wandinger-Ness A. Flow cytometry for real-time measurement of guanine nucleotide binding and exchange by Ras-like GTPases. Anal Biochem. 2008; 381:258-66.
17B. Curpan R F, Simons P C, Zhai D, Young S M, Carter M B, Bologa C G, Oprea T I, Satterthwait A C, Reed J C, Edwards B S, Sklar L A. High-throughput screen for the chemical inhibitors of antiapoptotic bcl-2 family proteins by multiplex flow cytometry. Assay Drug Dev Technol. 2011; 9:465-74.
18B. Klasse P J, Moore J P. Quantitative model of antibody- and soluble CD4-mediated neutralization of primary isolates and T-cell line-adapted strains of human immunodeficiency virus type 1. J Virol. 1996; 70:3668-77.
19B. Simons P C, Young S M, Carter M B, Waller A, Zhai D, Reed J C, Edwards B S, Sklar L A. Simultaneous in vitro molecular screening of protein-peptide interactions by flow cytometry, using six Bcl-2 family proteins as examples. Nat Protoc. 2011; 6:943-52.
20B. Krautkramer E, Zeier M. Hantavirus causing hemorrhagic fever with renal syndrome enters from the apical surface and requires decay-accelerating factor (DAF/CD55) J Virol. 2008; 82:4257-64.
21B. Mold C, Walter E I, Medof M E. The influence of membrane components on regulation of alternative pathway activation by decay-accelerating factor. J Immunol. 1990; 145:3836-41.
22B. Reeder M K, Serebriiskii I G, Golemis E A, Chernoff J. Analysis of small GTPase signaling pathways using p21-activated kinase mutants that selectively couple to Cdc42. J Biol Chem. 2001; 276:40606-13.
23B. Reid T, Furuyashiki T, Ishizaki T, Watanabe G, Watanabe N, Fujisawa K, Morii N, Madaule P, Narumiya S. Rhotekin, a new putative target for Rho bearing homology to a serine/threonine kinase, PKN, and rhophilin in the rho-binding domain. J Biol Chem. 1996; 271:13556-60
24B. Chigaev A, Buranda T, Dwyer D C, Prossnitz E R, Sklar L A. FRET detection of cellular alpha 4-integrin conformational activation. Biophysical Journal. 2003; 85:3951-3962.
25B. Machacek M, Hodgson L, Welch C, Elliott H, Pertz O, Nalbant P, Abell A, Johnson G L, Hahn K M, Danuser G. Coordination of Rho GTPase activities during cell protrusion. Nature. 2009; 461:99-103.
26B. Burridge K, Wennerberg K. Rho and Rac take center stage. Cell. 2004; 116:167-79.
27B. Ridley A J, Schwartz M A, Burridge K, Firtel R A, Ginsberg M H, Borisy G, Parsons J T, Horwitz A R. Cell migration: integrating signals from front to back. Science. 2003; 302:1704-9.
28B. Ridley A J. Rho family proteins: coordinating cell responses. Trends Cell Biol. 2001; 11:471-7.
29B. Medley Q G, Serra-Pages C, Iannotti E, Seipel K, Tang M, O'Brien S P, Streuli M. The trio guanine nucleotide exchange factor is a RhoA target. Binding of RhoA to the trio immunoglobulin-like domain. J Biol Chem. 2000; 275:36116-23.
30B. Bellanger J M, Astier C, Sardet C, Ohta Y, Stossel T P, Debant A. The Rac1- and RhoG-specific GEF domain of Trio targets filamin to remodel cytoskeletal actin. Nat Cell Biol. 2000; 2:888-92.
31B. Schoenwaelder S M, Petch L A, Williamson D, Shen R, Feng G S, Burridge K. The protein tyrosine phosphatase Shp-2 regulates RhoA activity. Curr Biol. 2000; 10:1523-6.
32B. Burridge K, Doughman R. Front and back by Rho and Rac. Nat Cell Biol. 2006; 8:781-2.
33B. Parsons J T, Horwitz A R, Schwartz M A. Cell adhesion: integrating cytoskeletal dynamics and cellular tension. Nat Rev Mol Cell Biol. 2010; 11:633-43.

34B. Ridley A J, Hall A. The small GTP-binding protein rho regulates the assembly of focal adhesions and actin stress fibers in response to growth factors. Cell. 1992; 70:389-99.

35B. Kurokawa K, Itoh R E, Yoshizaki H, Nakamura Y O, Matsuda M. Coactivation of Rac1 and Cdc42 at lamellipodia and membrane ruffles induced by epidermal growth factor. Mol Biol Cell. 2004; 15:1003-10.

36B. Kinbara K, Goldfinger L E, Hansen M, Chou F L, Ginsberg M H. Ras GTPases: integrins' friends or foes? Nat Rev Mol Cell Biol. 2003; 4:767-76.

37B. Mochizuki N, Yamashita S, Kurokawa K, Ohba Y, Nagai T, Miyawaki A, Matsuda M. Spatio-temporal images of growth-factor-induced activation of Ras and Rap1. Nature. 2001; 411:1065-8.

38B. Honda S, Tomiyama Y, Pelletier A J, Annis D, Honda Y, Orchekowski R, Ruggeri Z, Kunicki T J. Topography of ligand-induced binding sites, including a novel cation-sensitive epitope (AP5) at the amino terminus, of the human integrin beta 3 subunit. J Biol Chem. 1995; 270:11947-54.

39B. del Pozo M A, Alderson N B, Kiosses W B, Chiang H H, Anderson R G, Schwartz M A. Integrins regulate Rac targeting by internalization of membrane domains. Science. 2004; 303:839-42.

40B. Coyne C B, Bergelson J M. Virus-induced Abl and Fyn kinase signals permit coxsackievirus entry through epithelial tight junctions. Cell. 2006; 124:119-31.

41B. Wojciak-Stothard B, Ridley A J. Rho GTPases and the regulation of endothelial permeability. Vascul Pharmacol. 2002; 39:187-99.

42B. Remans P H, Gringhuis S I, van Laar J M, Sanders M E, Papendrecht-van der Voort E A, Zwartkruis F J, Levarht E W, Rosas M, Coffer P J, Breedveld F C, Bos J L, Tak P P, Verweij C L, Reedquist K A. Rap1 signaling is required for suppression of Ras-generated reactive oxygen species and protection against oxidative stress in T lymphocytes. J Immunol. 2004; 173:920-31.

43B. Hughes P E, Renshaw M W, Pfaff M, Forsyth J, Keivens V M, Schwartz M A, Ginsberg M H. Suppression of integrin activation: a novel function of a Ras/Raf-initiated MAP kinase pathway. Cell. 1997; 88:521-30.

44B. Feng Y, Press B, Wandinger-Ness A. Rab 7: an important regulator of late endocytic membrane traffic. J Cell Biol. 1995; 131:1435-52.

45B. Bucci C, Parton R G, Mather I H, Stunnenberg H, Simons K, Hoflack B, Zerial M. The small GTPase rab5 functions as a regulatory factor in the early endocytic pathway. Cell. 1992; 70:715-28.

46B. Lozach P Y, Huotari J, Helenius A. Late-penetrating viruses. Curr Opin Virol. 2011; 1:35-43.

47B. Lozach P Y, Mancini R, Bitto D, Meier R, Oestereich L, Overby A K, Pettersson R F, Helenius A. Entry of bunyaviruses into mammalian cells. Cell Host Microbe. 2010; 7:488-99.

What is claimed is:

1. A method of using a multiplexed flow cytometric assay to diagnose a bacterial infection in a subject at risk for sepsis and assess the onset or progression of sepsis from said bacterial infection, the method comprising:
    (a) incubating a sample obtained from the subject with a population of fluorescent beads which have two or more sizes, which are labeled with a first fluorophore having a single wavelength and a plurality of intensity levels each of which beads is coupled to an effector protein which binds to a cognate, infection-associated-guanosine triphosphate hydrolase (GTPase), wherein said GTPase is ras-related C3 botulinum toxin substrate 1 (Rac1) or Ras related protein 1 (Rap1) and wherein said effector proteins which binds to Rac1 is selected from the group consisting of p21 activated kinase-1 rho binding domain (PAK-1 RBD), steroid receptor RNA activiator 1 (Sra1), Insulin Receptor Tyrosine Kinase Substrate p58/53 (IRSp58/53), p21 activated kinase 1 (PAK1), p21 activated kinase 2 (PAK2), p21 activated kinase 3 (PAK3) and mixtures thereof and said effector protein which binds to Rap1 is ral guanine nucleotide dissociation stimulator rho binding domain (RalGDS-RBD), wherein said fluorescent beads which are coupled to said effector proteins bind to said GTPase to form fluorescent bead-bound effector-GTPase complexes;
    (b) incubating the sample mixture of beads obtained from step (a) comprising the formed fluorescent bead-bound effector-GTPase complexes with primary antibodies which are specific for said GTPases;
    (c) incubating the fluorescent beads obtained from step (b) with secondary antibodies which are specific to said primary antibodies and which are labeled with a second fluorophore having a wavelength which is different from that of the first fluorophore; and
    (d) measuring the fluorescence intensities of the incubated beads of step (c) using flow cytometry to determine the presence and level of infection-associated-GTPases in the sample, wherein a level of infection associated GTPases which is elevated in comparison to a control or standard for a healthy control subject evidences that a bacterial infection is present in said subject;
    (e) analyzing the impairment of hemostasis and/or bacterial infection-related increase in thrombogenesis and fibrinolysis by measuring thrombin and/or plasmin levels in a blood sample obtained from the subject; and
    (f) comparing measured thrombin and/or plasmin levels in said subject to control thrombin and/or plasmin levels determined in a healthy control subject;
    wherein measured thrombin and/or plasmin levels which exceed corresponding control levels for a healthy control subject are indicative of the onset or progression of sepsis.

2. The method according to claim 1, wherein the first fluorophore is a red fluorophore and the second fluorophore is a green fluorophore.

3. The method according to claim 1 wherein said effector proteins are PAK-1 RBD and RalGDS-RBD.

4. A method of using a multiplexed flow cytometric assay to diagnose a bacterial infection in a subject at risk for sepsis and assess the onset or progression of sepsis from said bacterial infection, the method comprising:
    (a) incubating a sample obtained from the subject with a population of fluorescent beads which have two or more sizes, which are labeled with a first fluorophore having a single wavelength and a plurality of intensity levels each of which beads is coupled to an effector protein which binds to a cognate, infection-associated-guanosine triphosphate hydrolase (GTPase), wherein said GTPase is ras-related C3 botulinum toxin substrate 1 (Rac1) or Ras related protein 1 (Rap1) and wherein said effector protein which binds to Rac1 is p21 activated kinase-1 rho binding domain (PAK-1 RBD), and said effector protein which binds to Rap1 is ral guanine nucleotide dissociation stimulator rho binding domain (RalGDS-RBD), wherein said fluorescent beads which are coupled to said effector proteins bind to said GTPase to form fluorescent bead-bound effector-GT-Pase complexes;
(b) incubating the sample mixture of beads obtained from step (a) comprising the formed fluorescent bead-bound effector-GTPase complexes with primary antibodies which are specific for said GTPases;
(c) incubating the fluorescent beads obtained from step (b) with secondary antibodies which are specific to said primary antibodies and which are labeled with a second fluorophore having a wavelength which is different from that of the first fluorophore; and
(d) measuring the fluorescence intensities of the incubated beads of step (c) using flow cytometry to determine the presence and level of infection-associated-GTPases in the sample, wherein a level of infection associated GTPases which is elevated in comparison to a control or standard for a healthy control subject evidences that a bacterial infection is present in said subject;
(e) analyzing the impairment of hemostasis and/or bacterial infection-related increase in thrombogenesis and fibrinolysis by measuring thrombin and/or plasmin levels in a blood sample obtained from the subject; and
(f) comparing measured thrombin and/or plasmin levels in said subject to control thrombin and/or plasmin levels determined in a healthy control subject;
wherein measured thrombin and/or plasmin levels which exceed corresponding control levels for a healthy control subject are indicative of the onset or progression of sepsis.

5. The method according to claim 4, wherein the first fluorophore is a red fluorophore and the second fluorophore is a green fluorophore.

* * * * *